US012050256B2

United States Patent
Sofka et al.

(10) Patent No.: US 12,050,256 B2
(45) Date of Patent: *Jul. 30, 2024

(54) SYSTEMS AND METHODS FOR AUTOMATED DETECTION IN MAGNETIC RESONANCE IMAGES

(71) Applicant: Hyperfine Operations, Inc., Guilford, CT (US)

(72) Inventors: Michal Sofka, Princeton, NJ (US); Jonathan M. Rothberg, Miami Beach, FL (US); Gregory L. Charvat, Guilford, CT (US); Tyler S. Ralston, Clinton, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 892 days.

This patent is subject to a terminal disclaimer.

(21) Appl. No.: 16/925,048

(22) Filed: Jul. 9, 2020

(65) Prior Publication Data
US 2020/0341095 A1    Oct. 29, 2020

Related U.S. Application Data

(63) Continuation of application No. 15/820,182, filed on Nov. 21, 2017, now Pat. No. 10,718,842.
(Continued)

(51) Int. Cl.
*G01R 33/00*  (2006.01)
*A61B 5/00*  (2006.01)
(Continued)

(52) U.S. Cl.
CPC ........ *G01R 33/5608* (2013.01); *A61B 5/0042* (2013.01); *A61B 5/055* (2013.01);
(Continued)

(58) Field of Classification Search
CPC .................................................. G01R 33/5608
See application file for complete search history.

(56) References Cited

U.S. PATENT DOCUMENTS

| 3,622,869 A | 11/1971 | Golay |
| 3,735,306 A | 5/1973 | Kabler et al. |

(Continued)

FOREIGN PATENT DOCUMENTS

| CA | 2965437 A1 | 5/2016 |
| CN | 1269512 A | 10/2000 |

(Continued)

OTHER PUBLICATIONS

U.S. Appl. No. 15/820,073, filed Nov. 21, 2017, Sofka et al.
(Continued)

*Primary Examiner* — Joseph M Santos Rodriguez
(74) *Attorney, Agent, or Firm* — Foley & Lardner LLP

(57) ABSTRACT

Some aspects include a method of determining change in size of an abnormality in a brain of a patient positioned within a low-field magnetic resonance imaging (MRI) device. The method comprises, while the patient remains positioned within the low-field MRI device, acquiring first and second magnetic resonance (MR) image data of the patient's brain; providing the first and second MR image data as input to a trained statistical classifier to obtain corresponding first and second output; identifying, using the first output, at least one initial value of at least one feature indicative of a size of the abnormality; identifying, using the second output, at least one updated value of the at least one feature; determining the change in the size of the abnormality using the at least one initial value of the at least one feature and the at least one updated value of the at least one feature.

17 Claims, 28 Drawing Sheets

Related U.S. Application Data

(60) Provisional application No. 62/425,569, filed on Nov. 22, 2016.

(51) Int. Cl.
| | |
|---|---|
| *A61B 5/055* | (2006.01) |
| *G01R 33/38* | (2006.01) |
| *G01R 33/44* | (2006.01) |
| *G01R 33/48* | (2006.01) |
| *G01R 33/483* | (2006.01) |
| *G01R 33/56* | (2006.01) |
| *G06F 18/2411* | (2023.01) |
| *G06F 18/2413* | (2023.01) |
| *G06T 7/00* | (2017.01) |
| *G06V 10/764* | (2022.01) |
| *G06V 10/82* | (2022.01) |
| *G01R 33/383* | (2006.01) |
| *G06N 3/044* | (2023.01) |
| *G06N 3/045* | (2023.01) |

(52) U.S. Cl.
CPC .......... *A61B 5/4064* (2013.01); *A61B 5/7267* (2013.01); *G01R 33/3806* (2013.01); *G01R 33/445* (2013.01); *G01R 33/4806* (2013.01); *G01R 33/483* (2013.01); *G06F 18/2411* (2023.01); *G06F 18/24143* (2023.01); *G06T 7/0012* (2013.01); *G06T 7/0016* (2013.01); *G06V 10/764* (2022.01); *G06V 10/82* (2022.01); *A61B 2576/026* (2013.01); *G01R 33/383* (2013.01); *G06N 3/044* (2023.01); *G06N 3/045* (2023.01); *G06T 2207/10088* (2013.01); *G06T 2207/20081* (2013.01); *G06T 2207/20084* (2013.01); *G06T 2207/20092* (2013.01); *G06T 2207/20212* (2013.01); *G06T 2207/30016* (2013.01); *G06T 2207/30101* (2013.01); *G06T 2207/30172* (2013.01); *G06V 2201/031* (2022.01)

(56) References Cited

U.S. PATENT DOCUMENTS

| | | |
|---|---|---|
| 4,595,899 A | 6/1986 | Smith et al. |
| 4,621,299 A | 11/1986 | Hill |
| 4,638,252 A | 1/1987 | Bradshaw |
| 4,668,915 A | 5/1987 | Daubin et al. |
| 4,675,609 A | 6/1987 | Danby et al. |
| 4,680,545 A | 7/1987 | Gray et al. |
| 4,770,182 A | 9/1988 | Damadian et al. |
| 4,890,061 A | 12/1989 | Den Boef |
| 4,893,082 A | 1/1990 | Letcher |
| 5,038,785 A | 8/1991 | Blakeley et al. |
| 5,047,720 A | 9/1991 | Guy |
| 5,134,374 A | 7/1992 | Breneman et al. |
| 5,153,546 A | 10/1992 | Laskaris |
| 5,194,810 A | 3/1993 | Breneman et al. |
| 5,203,332 A | 4/1993 | Leunbach |
| 5,227,723 A | 7/1993 | Sepponen |
| 5,252,924 A | 10/1993 | Sakurai et al. |
| 5,291,137 A | 3/1994 | Freedman |
| 5,382,904 A | 1/1995 | Pissanetzky |
| 5,390,673 A | 2/1995 | Kikinis |
| 5,423,315 A | 6/1995 | Margosian et al. |
| 5,463,364 A | 10/1995 | Muller |
| 5,481,192 A | 1/1996 | Mehlkopf et al. |
| 5,483,158 A | 1/1996 | van Heteren et al. |
| 5,490,509 A | 2/1996 | Carlson et al. |
| 5,570,073 A | 10/1996 | Muller |
| 5,581,187 A | 12/1996 | Pausch |
| 5,659,281 A | 8/1997 | Pissanetzky et al. |
| 5,808,376 A | 9/1998 | Gordon et al. |
| 5,864,236 A | 1/1999 | Li |
| 5,877,665 A | 3/1999 | Obasih et al. |
| 6,023,165 A | 2/2000 | Damadian et al. |
| 6,029,081 A | 2/2000 | Demeester et al. |
| 6,037,850 A | 3/2000 | Honmei et al. |
| 6,075,364 A | 6/2000 | Damadian et al. |
| 6,131,690 A | 10/2000 | Galando et al. |
| 6,147,578 A | 11/2000 | Panfil et al. |
| 6,150,820 A | 11/2000 | Damadian et al. |
| 6,150,911 A | 11/2000 | Katznelson et al. |
| 6,157,278 A | 12/2000 | Katznelson et al. |
| 6,157,281 A | 12/2000 | Katznelson et al. |
| 6,163,240 A | 12/2000 | Zuk et al. |
| 6,225,805 B1 | 5/2001 | Damadian et al. |
| 6,235,409 B1 | 5/2001 | Serafin |
| 6,262,576 B1 | 7/2001 | Petropoulos |
| 6,267,830 B1 | 7/2001 | Groll |
| 6,278,274 B1 | 8/2001 | Biglieri et al. |
| 6,288,546 B1 | 9/2001 | Damadian et al. |
| 6,294,972 B1 | 9/2001 | Jesmanowicz et al. |
| 6,317,618 B1 | 11/2001 | Livni et al. |
| 6,346,814 B1 | 2/2002 | Carrozzi et al. |
| 6,362,620 B1 | 3/2002 | Debbins et al. |
| 6,373,251 B1 | 4/2002 | Damadian et al. |
| 6,377,830 B1 | 4/2002 | Carrozzi et al. |
| 6,400,156 B1 | 6/2002 | Damadian et al. |
| 6,404,197 B1 | 6/2002 | Anderson et al. |
| 6,411,187 B1 | 6/2002 | Rotem et al. |
| 6,417,797 B1 | 7/2002 | Cousins et al. |
| 6,424,154 B1 | 7/2002 | Young |
| 6,445,185 B1 | 9/2002 | Damadian et al. |
| 6,452,472 B1 | 9/2002 | Aoki et al. |
| 6,492,812 B1 | 12/2002 | Debbins et al. |
| 6,507,192 B1 | 1/2003 | Damadian et al. |
| 6,522,145 B1 | 2/2003 | Damadian et al. |
| 6,611,702 B2 | 8/2003 | Rohling et al. |
| 6,621,267 B1 | 9/2003 | Damadian et al. |
| 6,677,752 B1 | 1/2004 | Creighton et al. |
| 6,801,038 B2 | 10/2004 | Carrozzi et al. |
| 6,819,108 B2 | 11/2004 | Huang et al. |
| 6,842,002 B2 | 1/2005 | Cheng et al. |
| 6,844,732 B2 | 1/2005 | Carlini et al. |
| 6,845,262 B2 | 1/2005 | Albert et al. |
| 7,019,610 B2 | 3/2006 | Creighton et al. |
| 7,116,102 B2 | 10/2006 | Clarke et al. |
| 7,126,333 B2 | 10/2006 | Beard et al. |
| 7,215,231 B1 | 5/2007 | Morrone |
| 7,218,104 B2 | 5/2007 | Clarke et al. |
| 7,239,143 B2 | 7/2007 | McBride |
| 7,345,560 B2 | 3/2008 | Laskaris et al. |
| 7,414,401 B1 | 8/2008 | Lvovsky |
| 7,417,426 B2 | 8/2008 | Race et al. |
| 7,423,431 B2 | 9/2008 | Amm et al. |
| 7,504,825 B2 | 3/2009 | Pittaluga et al. |
| 7,529,575 B2 | 5/2009 | Rezzonico et al. |
| 7,538,553 B2 | 5/2009 | Trequattrini et al. |
| 7,548,061 B2 | 6/2009 | Dewdney et al. |
| 7,659,719 B2 | 2/2010 | Vaughan et al. |
| 7,671,587 B2 | 3/2010 | Penanen et al. |
| 7,734,324 B2 | 6/2010 | Biglieri et al. |
| 7,759,938 B2 | 7/2010 | Prado et al. |
| 7,821,402 B2 | 10/2010 | Yang et al. |
| 7,834,270 B2 | 11/2010 | Zhu et al. |
| 7,869,857 B2 | 1/2011 | Satragno et al. |
| 7,966,059 B2 | 6/2011 | Creighton et al. |
| 8,008,914 B2 | 8/2011 | Penanen et al. |
| 8,049,504 B2 | 11/2011 | Findekelee |
| 8,120,358 B2 | 2/2012 | Du |
| 8,203,341 B2 | 6/2012 | Teklemariam et al. |
| 8,232,799 B2 | 7/2012 | Hajian et al. |
| 8,253,415 B2 | 8/2012 | Umeda |
| 8,322,024 B2 | 12/2012 | Aoki et al. |
| 8,335,359 B2 | 12/2012 | Fidrich et al. |
| 8,368,402 B2 | 2/2013 | Lee et al. |
| 8,378,682 B2 | 2/2013 | Subbarao |
| 8,409,807 B2 | 4/2013 | Neely et al. |
| 8,427,148 B2 | 4/2013 | O'Connor |
| 8,451,004 B2 | 5/2013 | Walsh |
| 8,487,623 B2 | 7/2013 | Penanen et al. |
| 8,514,043 B2 | 8/2013 | Wang et al. |

(56) References Cited

U.S. PATENT DOCUMENTS

| | | |
|---|---|---|
| 8,519,708 B2 | 8/2013 | Prado et al. |
| 8,563,298 B2 | 10/2013 | Lowery, Jr. et al. |
| 8,570,035 B2 | 10/2013 | Wemmer et al. |
| 8,570,042 B2 | 10/2013 | Pines et al. |
| 8,614,575 B2 | 12/2013 | Demas et al. |
| 8,618,799 B1 | 12/2013 | Radparvar et al. |
| 8,626,266 B1 | 1/2014 | Frank et al. |
| 8,634,616 B2 | 1/2014 | Den Harder et al. |
| 8,699,199 B2 | 4/2014 | Blakes |
| 8,791,698 B2 | 7/2014 | Umeda |
| 8,816,684 B2 | 8/2014 | Walsh |
| 8,850,338 B2 | 9/2014 | Baumgart |
| 8,852,162 B2 | 10/2014 | Williams et al. |
| 8,901,928 B2 | 12/2014 | Alexiuk et al. |
| 8,970,217 B1 | 3/2015 | Kadin |
| 8,993,898 B2 | 3/2015 | Weibler et al. |
| 9,165,360 B1 | 10/2015 | Bates et al. |
| 9,222,998 B2 | 12/2015 | Teklemariam et al. |
| 9,244,139 B2 | 1/2016 | Brown et al. |
| 9,255,978 B2 | 2/2016 | Fallone et al. |
| 9,412,163 B2 | 8/2016 | Peng et al. |
| 9,500,727 B2 | 11/2016 | Sohn et al. |
| 9,500,731 B2 | 11/2016 | Castillo |
| 9,541,616 B2 | 1/2017 | Rothberg et al. |
| 9,547,057 B2 | 1/2017 | Rearick et al. |
| 9,581,668 B2 | 2/2017 | Waddell |
| 9,613,416 B1 | 4/2017 | Bates et al. |
| 9,625,543 B2 | 4/2017 | Rearick et al. |
| 9,625,544 B2 | 4/2017 | Poole et al. |
| 9,638,773 B2 | 5/2017 | Poole et al. |
| 9,645,210 B2 | 5/2017 | McNulty et al. |
| 9,678,183 B2 | 6/2017 | Bulumulla et al. |
| 9,797,971 B2 | 10/2017 | Rearick et al. |
| 9,814,390 B2 | 11/2017 | Piron et al. |
| 9,817,093 B2 | 11/2017 | Rothberg et al. |
| 9,897,668 B2 | 2/2018 | Piron et al. |
| 9,910,115 B2 | 3/2018 | Wald et al. |
| 10,139,464 B2 | 11/2018 | Rearick et al. |
| 10,145,913 B2 | 12/2018 | Hugon et al. |
| 10,145,922 B2 | 12/2018 | Rothberg et al. |
| 10,162,026 B2 | 12/2018 | Walsh |
| 10,222,434 B2 | 3/2019 | Poole et al. |
| 10,222,435 B2 | 3/2019 | Mileski et al. |
| 10,241,177 B2 | 3/2019 | Poole et al. |
| 10,274,561 B2 | 4/2019 | Poole et al. |
| 10,281,540 B2 | 5/2019 | Mileski et al. |
| 10,281,541 B2 | 5/2019 | Poole et al. |
| 10,295,628 B2 | 5/2019 | Mileski et al. |
| 10,310,037 B2 | 6/2019 | McNulty et al. |
| 10,317,502 B2 | 6/2019 | Harvey et al. |
| 10,324,147 B2 | 6/2019 | McNulty et al. |
| 10,330,755 B2 | 6/2019 | Poole et al. |
| 10,353,030 B2 | 7/2019 | Poole et al. |
| 10,371,733 B2 | 8/2019 | Pal et al. |
| 10,371,773 B2 | 8/2019 | Poole et al. |
| 10,379,186 B2 | 8/2019 | Rothberg et al. |
| 10,416,264 B2 | 9/2019 | Sofka et al. |
| 10,444,310 B2 | 10/2019 | Poole et al. |
| 10,466,327 B2 | 11/2019 | Rothberg et al. |
| 10,488,482 B2 | 11/2019 | Rearick et al. |
| 10,495,712 B2 | 12/2019 | Rothberg et al. |
| 10,520,566 B2 | 12/2019 | Poole et al. |
| 10,527,692 B2 | 1/2020 | McNulty et al. |
| 10,534,058 B2 | 1/2020 | Sofka et al. |
| 10,539,637 B2 | 1/2020 | Poole et al. |
| 10,545,207 B2 | 1/2020 | Poole et al. |
| 10,551,452 B2 | 2/2020 | Rearick et al. |
| 10,564,239 B2 | 2/2020 | Poole et al. |
| 10,585,153 B2 | 3/2020 | McNulty et al. |
| 10,585,156 B2 | 3/2020 | Sofka et al. |
| 10,591,561 B2 | 3/2020 | Sacolick et al. |
| 10,591,564 B2 | 3/2020 | Rothberg et al. |
| 10,613,181 B2 | 4/2020 | Rothberg et al. |
| 10,627,464 B2 | 4/2020 | Dyvorne et al. |
| 10,641,852 B2 | 5/2020 | Poole et al. |
| 10,649,050 B2 | 5/2020 | Poole et al. |
| 10,684,335 B2 | 6/2020 | Poole et al. |
| 10,698,050 B2 | 6/2020 | Poole et al. |
| 10,709,387 B2 | 7/2020 | Poole et al. |
| 10,718,835 B2 | 7/2020 | Poole et al. |
| 10,720,230 B2 | 7/2020 | Frenkel et al. |
| 10,816,629 B2 | 10/2020 | Sofka et al. |
| 10,921,404 B2 | 2/2021 | Poole et al. |
| 10,955,504 B2 | 3/2021 | Sofka et al. |
| 11,215,685 B2 | 1/2022 | Poole et al. |
| 11,221,386 B2 | 1/2022 | Rearick et al. |
| 11,510,588 B2 | 11/2022 | Sacolick et al. |
| 2001/0000727 A1 | 5/2001 | Driehuys et al. |
| 2002/0000806 A1 | 1/2002 | Nakamura et al. |
| 2002/0050895 A1 | 5/2002 | Zuk et al. |
| 2002/0057088 A1 | 5/2002 | Carrozzi et al. |
| 2002/0084782 A1 | 7/2002 | Guthrie |
| 2002/0087063 A1 | 7/2002 | Lou |
| 2002/0175792 A1 | 11/2002 | Laskaris et al. |
| 2002/0192707 A1 | 12/2002 | Stockman |
| 2003/0001575 A1 | 1/2003 | Cheng et al. |
| 2003/0011451 A1 | 1/2003 | Katznelson et al. |
| 2003/0094947 A1 | 5/2003 | Akgun |
| 2003/0160622 A1 | 8/2003 | Duensing et al. |
| 2003/0214296 A1 | 11/2003 | Carlini et al. |
| 2004/0002645 A1 | 1/2004 | Ewing et al. |
| 2004/0097802 A1 | 5/2004 | Cohen |
| 2004/0164739 A1 | 8/2004 | Peterson et al. |
| 2004/0189301 A1 | 9/2004 | Biglieri et al. |
| 2004/0251901 A1 | 12/2004 | Tsuda et al. |
| 2005/0021019 A1 | 1/2005 | Hashimshony et al. |
| 2005/0049491 A1 | 3/2005 | Rezzonico et al. |
| 2005/0218896 A1 | 10/2005 | Gortler |
| 2005/0240099 A1 | 10/2005 | Sun et al. |
| 2005/0245810 A1 | 11/2005 | Khamene et al. |
| 2006/0052687 A1 | 3/2006 | Ruohonen |
| 2006/0071661 A1 | 4/2006 | Ong |
| 2006/0073101 A1 | 4/2006 | Oldfield et al. |
| 2006/0077027 A1 | 4/2006 | Aoki |
| 2006/0089544 A1 | 4/2006 | Williams et al. |
| 2006/0091881 A1 | 5/2006 | Clarke et al. |
| 2006/0186884 A1 | 8/2006 | Mallett et al. |
| 2006/0238196 A1 | 10/2006 | Havens et al. |
| 2006/0241333 A1 | 10/2006 | Hunter |
| 2006/0253020 A1 | 11/2006 | Ehman et al. |
| 2006/0255938 A1 | 11/2006 | Van Den Brink |
| 2007/0078334 A1 | 4/2007 | Scully et al. |
| 2007/0120631 A1 | 5/2007 | Hobbs et al. |
| 2007/0216413 A1 | 9/2007 | Legall et al. |
| 2007/0244385 A1 | 10/2007 | Satragno et al. |
| 2007/0252595 A1 | 11/2007 | Volegov et al. |
| 2007/0257800 A1 | 11/2007 | Yang et al. |
| 2007/0285197 A1 | 12/2007 | Shi et al. |
| 2007/0293753 A1 | 12/2007 | El-Sharkawy et al. |
| 2008/0027306 A1 | 1/2008 | Washburn et al. |
| 2008/0048658 A1 | 2/2008 | Hushek et al. |
| 2008/0084209 A1 | 4/2008 | Seeber et al. |
| 2008/0139896 A1 | 6/2008 | Baumgart et al. |
| 2008/0197845 A1 | 8/2008 | Trequattrini et al. |
| 2008/0258728 A1 | 10/2008 | Vernickel et al. |
| 2009/0012387 A1 | 1/2009 | Hanson et al. |
| 2009/0072828 A1 | 3/2009 | Penanen |
| 2009/0076377 A1 | 3/2009 | Findekelee |
| 2009/0099444 A1 | 4/2009 | Bogdanov |
| 2009/0136104 A1 | 5/2009 | Hajian et al. |
| 2009/0138058 A1 | 5/2009 | Cooke et al. |
| 2009/0167304 A1 | 7/2009 | Prado et al. |
| 2009/0224761 A1 | 9/2009 | Umeda |
| 2009/0309598 A1 | 12/2009 | Zhu et al. |
| 2010/0000780 A1 | 1/2010 | Zhu et al. |
| 2010/0033185 A1 | 2/2010 | Saha et al. |
| 2010/0056897 A1 | 3/2010 | Zhang |
| 2010/0160817 A1 | 6/2010 | Parihar et al. |
| 2010/0175792 A1 | 7/2010 | Dietsche et al. |
| 2010/0181845 A1 | 7/2010 | Fiorello et al. |
| 2010/0188083 A1 | 7/2010 | Cao et al. |
| 2010/0219833 A1 | 9/2010 | McGinley et al. |
| 2010/0302701 A1 | 12/2010 | Olliges |
| 2010/0312095 A1 | 12/2010 | Jenkins et al. |

(56) References Cited

U.S. PATENT DOCUMENTS

| | | |
|---|---|---|
| 2011/0007445 A1 | 1/2011 | Blakes |
| 2011/0025332 A1 | 2/2011 | Abele |
| 2011/0037467 A1 | 2/2011 | Tsuda |
| 2011/0060210 A1 | 3/2011 | Ehman |
| 2011/0088940 A1 | 4/2011 | Nordling et al. |
| 2011/0109311 A1 | 5/2011 | Walsh |
| 2011/0115485 A1 | 5/2011 | Subbarao |
| 2011/0118588 A1 | 5/2011 | Komblau et al. |
| 2011/0142316 A1 | 6/2011 | Wang et al. |
| 2011/0175694 A1 | 7/2011 | Fallone et al. |
| 2011/0199086 A1 | 8/2011 | Tsuda et al. |
| 2011/0210731 A1 | 9/2011 | Walsh |
| 2011/0210734 A1 | 9/2011 | Darrow et al. |
| 2011/0210739 A1 | 9/2011 | Ham |
| 2011/0248715 A1 | 10/2011 | Teklemariam et al. |
| 2011/0316537 A1 | 12/2011 | Umeda |
| 2012/0003160 A1 | 1/2012 | Wolf et al. |
| 2012/0032767 A1 | 2/2012 | Iwasaki et al. |
| 2012/0092009 A1 | 4/2012 | Zhang et al. |
| 2012/0112747 A1 | 5/2012 | Alexiuk et al. |
| 2012/0165652 A1 | 6/2012 | Dempsey |
| 2012/0184840 A1 | 7/2012 | Najarian et al. |
| 2012/0196753 A1 | 8/2012 | Laskaris et al. |
| 2012/0223705 A1 | 9/2012 | Lowery et al. |
| 2012/0240385 A1 | 9/2012 | Teklemariam et al. |
| 2012/0268117 A1 | 10/2012 | Romano et al. |
| 2012/0280683 A1 | 11/2012 | Sacolick et al. |
| 2012/0296195 A1 | 11/2012 | Abbott et al. |
| 2012/0296197 A1 | 11/2012 | Vahala et al. |
| 2012/0323110 A1 | 12/2012 | Blake et al. |
| 2013/0035587 A1 | 2/2013 | Lagendijk et al. |
| 2013/0072780 A1 | 3/2013 | Espy et al. |
| 2013/0116544 A1 | 5/2013 | Rey et al. |
| 2013/0204115 A1 | 8/2013 | Dam et al. |
| 2013/0214612 A1 | 8/2013 | Bae |
| 2013/0271142 A1 | 10/2013 | Penanen et al. |
| 2013/0278255 A1 | 10/2013 | Khalighi et al. |
| 2013/0279784 A1 | 10/2013 | Gill et al. |
| 2013/0285659 A1 | 10/2013 | Sohn et al. |
| 2013/0296660 A1 | 11/2013 | Tsien et al. |
| 2014/0011217 A1 | 1/2014 | Weissleder et al. |
| 2014/0066739 A1 | 3/2014 | He et al. |
| 2014/0111202 A1 | 4/2014 | Wald et al. |
| 2014/0128722 A1 | 5/2014 | Schweitzer et al. |
| 2014/0155732 A1 | 6/2014 | Patz et al. |
| 2014/0164739 A1 | 6/2014 | Gschwind et al. |
| 2014/0226890 A1 | 8/2014 | O'Brien et al. |
| 2014/0229141 A1 | 8/2014 | Fallone et al. |
| 2014/0232402 A1 | 8/2014 | Tsuda |
| 2014/0275953 A1 | 9/2014 | Gregerson et al. |
| 2014/0275970 A1 | 9/2014 | Brown et al. |
| 2014/0341456 A1 | 11/2014 | Rodriguez et al. |
| 2014/0347053 A1 | 11/2014 | Dempsey et al. |
| 2014/0354277 A1 | 12/2014 | Dewdney et al. |
| 2014/0364720 A1 | 12/2014 | Darrow et al. |
| 2015/0087957 A1 | 3/2015 | Liu et al. |
| 2015/0141799 A1 | 5/2015 | Rapoport et al. |
| 2015/0177343 A1 | 6/2015 | Wald et al. |
| 2015/0198684 A1 | 7/2015 | Basha et al. |
| 2015/0230810 A1 | 8/2015 | Creighton et al. |
| 2015/0253401 A1 | 9/2015 | Rapoport |
| 2015/0285882 A1 | 10/2015 | Mezrich et al. |
| 2015/0301134 A1 | 10/2015 | Hoshino et al. |
| 2015/0342177 A1 | 12/2015 | Hassanein et al. |
| 2015/0366527 A1 | 12/2015 | Yu et al. |
| 2015/0374395 A1 | 12/2015 | Creighton |
| 2016/0005183 A1 | 1/2016 | Thiagarajan et al. |
| 2016/0011290 A1 | 1/2016 | Iannello |
| 2016/0025832 A1 | 1/2016 | Piron et al. |
| 2016/0035091 A1 | 2/2016 | Kubassova |
| 2016/0035093 A1* | 2/2016 | Kateb ............... G02B 21/0012 382/131 |
| 2016/0066856 A1 | 3/2016 | Liang et al. |
| 2016/0069968 A1 | 3/2016 | Rothberg et al. |
| 2016/0069970 A1 | 3/2016 | Rearick et al. |
| 2016/0069971 A1 | 3/2016 | McNulty et al. |
| 2016/0069972 A1 | 3/2016 | Poole et al. |
| 2016/0069975 A1 | 3/2016 | Rothberg et al. |
| 2016/0110904 A1 | 4/2016 | Jeon et al. |
| 2016/0128592 A1 | 5/2016 | Rosen et al. |
| 2016/0131727 A1 | 5/2016 | Sacolick et al. |
| 2016/0139224 A1 | 5/2016 | Assif |
| 2016/0140435 A1 | 5/2016 | Bengio et al. |
| 2016/0169992 A1 | 6/2016 | Rothberg et al. |
| 2016/0169993 A1 | 6/2016 | Rearick et al. |
| 2016/0187436 A1 | 6/2016 | Piron et al. |
| 2016/0223631 A1 | 8/2016 | Poole et al. |
| 2016/0231399 A1 | 8/2016 | Rothberg et al. |
| 2016/0231402 A1 | 8/2016 | Rothberg et al. |
| 2016/0231403 A1 | 8/2016 | Rothberg et al. |
| 2016/0231404 A1 | 8/2016 | Rothberg et al. |
| 2016/0232690 A1 | 8/2016 | Ahmad et al. |
| 2016/0299203 A1 | 10/2016 | Mileski et al. |
| 2016/0334479 A1 | 11/2016 | Poole et al. |
| 2016/0354058 A1 | 12/2016 | Schlosser et al. |
| 2016/0356869 A1 | 12/2016 | Dempsey et al. |
| 2017/0007148 A1 | 1/2017 | Kaditz et al. |
| 2017/0011255 A1 | 1/2017 | Kaditz et al. |
| 2017/0038451 A1 | 2/2017 | Ristic et al. |
| 2017/0102443 A1 | 4/2017 | Rearick et al. |
| 2017/0103525 A1 | 4/2017 | Hu et al. |
| 2017/0108569 A1 | 4/2017 | Harvey et al. |
| 2017/0140551 A1 | 5/2017 | Bauer et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2017/0285122 A1 | 10/2017 | Kaditz et al. |
| 2017/0360401 A1 | 12/2017 | Rothberg et al. |
| 2017/0363700 A1 | 12/2017 | Gall et al. |
| 2018/0024208 A1 | 1/2018 | Rothberg et al. |
| 2018/0038931 A1 | 2/2018 | Rearick et al. |
| 2018/0068438 A1 | 3/2018 | DeVries |
| 2018/0070852 A1 | 3/2018 | Azulay et al. |
| 2018/0074140 A1 | 3/2018 | Yang et al. |
| 2018/0088193 A1 | 3/2018 | Rearick et al. |
| 2018/0136292 A1 | 5/2018 | Piron et al. |
| 2018/0143272 A1 | 5/2018 | Liu |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0210047 A1 | 7/2018 | Poole et al. |
| 2018/0224512 A1 | 8/2018 | Poole et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2018/0288118 A1 | 10/2018 | Bae et al. |
| 2018/0365824 A1 | 12/2018 | Yuh et al. |
| 2019/0004130 A1 | 1/2019 | Poole et al. |
| 2019/0011510 A1 | 1/2019 | Hugon et al. |
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNnulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0086497 A1 | 3/2019 | Rearick et al. |
| 2019/0101607 A1 | 4/2019 | Rothberg et al. |
| 2019/0162806 A1 | 5/2019 | Poole et al. |
| 2019/0178962 A1 | 6/2019 | Poole et al. |
| 2019/0178963 A1 | 6/2019 | Poole et al. |
| 2019/0227136 A1 | 7/2019 | Mileski et al. |
| 2019/0227137 A1 | 7/2019 | Mileski et al. |
| 2019/0250227 A1 | 8/2019 | McNulty et al. |

(56) References Cited

U.S. PATENT DOCUMENTS

| | | | |
|---|---|---|---|
| 2019/0250228 | A1 | 8/2019 | McNulty et al. |
| 2019/0257903 | A1 | 8/2019 | Poole et al. |
| 2019/0324098 | A1 | 10/2019 | McNulty et al. |
| 2019/0353720 | A1 | 11/2019 | Dyvorne et al. |
| 2019/0353723 | A1 | 11/2019 | Dyvorne et al. |
| 2019/0353726 | A1 | 11/2019 | Poole et al. |
| 2019/0353727 | A1 | 11/2019 | Dyvorne et al. |
| 2020/0003854 | A1 | 1/2020 | Okamoto |
| 2020/0011952 | A1 | 1/2020 | Rothberg et al. |
| 2020/0018806 | A1 | 1/2020 | Rothberg et al. |
| 2020/0022611 | A1 | 1/2020 | Nelson et al. |
| 2020/0022612 | A1 | 1/2020 | McNulty et al. |
| 2020/0022613 | A1 | 1/2020 | Nelson et al. |
| 2020/0025846 | A1 | 1/2020 | Nelson et al. |
| 2020/0025851 | A1 | 1/2020 | Rearick et al. |
| 2020/0033431 | A1 | 1/2020 | Schlemper et al. |
| 2020/0034998 | A1 | 1/2020 | Schlemper et al. |
| 2020/0041588 | A1 | 2/2020 | O'Halloran et al. |
| 2020/0045112 | A1 | 2/2020 | Sacolick et al. |
| 2020/0058106 | A1 | 2/2020 | Lazarus et al. |
| 2020/0081084 | A1 | 3/2020 | Poole et al. |
| 2020/0088817 | A1 | 3/2020 | Poole et al. |
| 2020/0150202 | A1 | 5/2020 | Hugon et al. |
| 2020/0150204 | A1 | 5/2020 | Poole et al. |
| 2020/0200844 | A1 | 6/2020 | Boskamp et al. |
| 2020/0209334 | A1 | 7/2020 | O'Halloran et al. |
| 2020/0233049 | A1 | 7/2020 | Poole et al. |
| 2020/0289019 | A1 | 9/2020 | Schlemper et al. |
| 2020/0289022 | A1 | 9/2020 | Coumans et al. |
| 2020/0294229 | A1 | 9/2020 | Schlemper et al. |
| 2020/0294282 | A1 | 9/2020 | Schlemper et al. |
| 2020/0294287 | A1 | 9/2020 | Schlemper et al. |
| 2020/0337587 | A1 | 10/2020 | Sacolick et al. |
| 2020/0355765 | A1 | 11/2020 | Chen et al. |
| 2021/0048498 | A1 | 2/2021 | Dyvorne et al. |
| 2021/0153765 | A1 | 5/2021 | Sacolick et al. |
| 2022/0091211 | A1 | 3/2022 | Rearick et al. |

FOREIGN PATENT DOCUMENTS

| | | |
|---|---|---|
| CN | 1394550 A | 2/2003 |
| CN | 1977766 A | 6/2007 |
| CN | 101162637 A | 4/2008 |
| CN | 101606208 A | 12/2009 |
| CN | 101903790 A | 12/2010 |
| CN | 101919696 A | 12/2010 |
| CN | 102713465 A | 10/2012 |
| CN | 102800057 A | 11/2012 |
| CN | 103747726 A | 4/2014 |
| CN | 103892831 A | 7/2014 |
| CN | 103892834 A | 7/2014 |
| CN | 106164694 A | 11/2016 |
| DE | 69931325 T2 | 4/2007 |
| EP | 0 921 537 A2 | 6/1999 |
| EP | 0 995 397 A2 | 4/2000 |
| EP | 0 995 397 A3 | 4/2000 |
| EP | 0 995 397 B1 | 4/2000 |
| EP | 1 004 269 A1 | 5/2000 |
| EP | 1 004 269 B1 | 5/2000 |
| EP | 1 262 786 A2 | 12/2002 |
| EP | 1 262 786 A3 | 12/2002 |
| EP | 2 418 516 A2 | 2/2012 |
| EP | 3 161 790 A1 | 5/2017 |
| ES | 2260874 T3 | 11/2006 |
| ES | 2359543 T3 | 5/2011 |
| JP | S60-063972 A | 4/1985 |
| JP | S61-097806 A | 5/1986 |
| JP | 63-311945 A | 12/1988 |
| JP | S64-064637 A | 3/1989 |
| JP | H164637 U | 4/1989 |
| JP | H01-242057 A | 9/1989 |
| JP | H03-188831 A | 8/1991 |
| JP | H05-182821 A | 7/1993 |
| JP | H05-344960 A | 12/1993 |
| JP | H08-168470 A | 7/1996 |
| JP | S63-065848 A | 3/1998 |
| JP | H10-127604 A | 5/1998 |
| JP | 2000-157510 A | 6/2000 |
| JP | 2000-201902 A | 7/2000 |
| JP | 2000-237164 A | 9/2000 |
| JP | 2001-137212 A | 5/2001 |
| JP | 2001-511597 A | 8/2001 |
| JP | 2001-517510 A | 10/2001 |
| JP | 2002-143124 A | 5/2002 |
| JP | 2004-065398 A | 3/2004 |
| JP | 2004-081264 A | 3/2004 |
| JP | 2004-187945 A | 7/2004 |
| JP | 2004-255189 A | 9/2004 |
| JP | 2004-536367 A | 12/2004 |
| JP | 2005-118098 A2 | 5/2005 |
| JP | 2005-237501 A | 9/2005 |
| JP | 2005-344960 A | 12/2005 |
| JP | 2007-167634 A | 7/2007 |
| JP | H08-031635 A | 2/2008 |
| JP | 2008-168470 A | 7/2008 |
| JP | 2009-082465 A | 4/2009 |
| JP | 2012-029999 A | 2/2012 |
| JP | 2013-526992 A | 6/2013 |
| JP | 2014-523795 A | 9/2014 |
| JP | 2015-519175 A | 7/2015 |
| JP | 2016-016205 A | 2/2016 |
| JP | 2017-516992 A | 6/2017 |
| KR | 10-2014-0063649 A | 5/2014 |
| TW | 389688 B | 5/2000 |
| TW | 570771 B | 1/2004 |
| TW | 201712357 A | 4/2017 |
| WO | WO-99/05531 A2 | 2/1999 |
| WO | WO-2008/008447 A2 | 1/2008 |
| WO | WO-2009/042131 A1 | 4/2009 |
| WO | WO-2010/029725 A1 | 3/2010 |
| WO | WO-2010/073923 A1 | 7/2010 |
| WO | WO 2010/117573 A2 | 10/2010 |
| WO | WO-2013/016639 A1 | 1/2013 |
| WO | WO-2013/111072 A1 | 8/2013 |
| WO | WO-2013/187924 A1 | 12/2013 |
| WO | WO-2014/013257 A1 | 1/2014 |
| WO | WO-2014/076808 A1 | 5/2014 |
| WO | WO-2014/102215 A1 | 7/2014 |
| WO | WO 2015/138939 A1 | 9/2015 |
| WO | WO-2015/150236 A1 | 10/2015 |
| WO | WO 2015/177268 A1 | 11/2015 |
| WO | WO-2015/189786 A1 | 12/2015 |
| WO | WO 2016/001825 A1 | 1/2016 |
| WO | WO-2016/037030 A1 | 3/2016 |
| WO | WO-2016/077417 A1 | 5/2016 |
| WO | WO-2016/183284 A1 | 11/2016 |
| WO | WO 2017/106645 A1 | 6/2017 |
| WO | WO-2019/068687 A2 | 4/2019 |

OTHER PUBLICATIONS

U.S. Appl. No. 15/820,182, filed Nov. 21, 2017, Sofka et al.
U.S. Appl. No. 15/820,219, filed Nov. 21, 2017, Sofka et al.
U.S. Appl. No. 16/116,301, filed Aug. 29, 2018, Sofka et al.
U.S. Appl. No. 16/116,389, filed Aug. 29, 2018, Sofka et al.
U.S. Appl. No. 16/116,476, filed Aug. 29, 2018, Sofka et al.
EP 17872998.4, Apr. 24, 2020, Extended European Search Report.
PCT/US2017/62763, Feb. 5, 2018, Invitation to Pay Additional Fees.
PCT/US2017/62763, Apr. 5, 2018, International Search Report and Written Opinion.
Extended European Search Report for European Application No. EP 21205232.8 dated Jan. 25, 2022.
Arenivas et al., Three approaches to investigating functional compromise to the default mode network after traumatic axonal injury. Brain imaging and behavior. Sep. 2014;8(3):407-19.
Chen et al., Automated ventricular systems segmentation in brain CT images by combining low-level segmentation and high-level template matching. BMC medical informatics and decision making. Dec. 2009;9(1):1-4.
U.S. Appl. No. 16/275,396, filed Feb. 14, 2019, Yeon Doo et al.

(56) References Cited

OTHER PUBLICATIONS

Acar et al., Effects of Forward Model Errors on EEG Source Localization. Brain Topogr.2013;23:378-96.
Blanco et al., Interventional and intraoperative MRI at low field scanner—a review. European Journal of Radiology, Elsevier Science. 2005;56(2): 130-42.
Blumich et al., NMR at low magnetic fields. Chemical Physics Letters. 2009;477(4-6):231-40.
Communication pursuant to Article 94(3) EPC dated Aug. 19, 2021 in connection with European Application No. 15838773.8.
Danieli et al., Mobile sensor for high resolution NMR spectroscopy and imaging. Journal of Magnetic Resonance, Academic Press. 2009; 198(1):80-7.
Extended European Search Report for European Application No. 15837569.1 dated Apr. 6, 2018.
Extended European Search Report for European Application No. 15838192.1 dated Apr. 4, 2018.
Extended European Search Report for European Application No. 15838773.8 dated Apr. 6, 2018.
Extended European Search Report for European Application No. EP 17874895.0 dated May 18, 2020.
Hidalgo-Tobon, Theory of gradient coil design methods for magnetic resonance imaging. Concepts in Magnetic Resonance Part A. Jul. 2010;36(4):223-42.
Holbrook et al., Interactive Interventional Applications for the MRI Scan Room. Proceedings of the International Society forMae.netic Resonance in Medicine. 2012:2954.
Http://www.Mifan.Org: "JM-BT20 MRI System", Apr. 12, 2016, XP055692541, Retrieved from the Internet: URL:http://www.joymedtech.com/products/76-JM-BT20-MRISystem.html [retrieved on May 7, 2020].
International Preliminary Report on Patentability for International Application No. PCT/US2017/063000 mailed Jun. 6, 2019.
International Preliminary Report on Patentability for International Application No. PCT/US2020/061281 mailed Jun. 9, 2022.
International Search Report and Written Opinion for International Application No. PCT/US2015/048470 mailed Dec. 10, 2015.
International Search Report and Written Opinion for International Application No. PCT/US2015/048479 dated Dec. 8, 2015.
International Search Report and Written Opinion for International Application No. PCT/US2015/048484 mailed Dec. 4, 2015.
International Search Report and Written Opinion for International Application No. PCT/US2015/048515 mailed Dec. 8, 2015.
International Search Report and Written Opinion for International Application No. PCT/US2017/063000 mailed Apr. 9, 2018.
International Search Report and Written Opinion for International Application No. PCT/US2019/33090 mailed Aug. 6, 2019.
International Search Report and Written Opinion for International Application No. PCT/US2020/061281 mailed Mar. 4, 2021.
International Search Report and Written Opinion for International Application No. PCT/US2015/060079 mailed Jan. 12, 2016.
Issadore et al., Miniature magnetic resonance system for point-of-care diagnostics. Lab on a Chip. 2011;11(13):2282-7.
Jwo et al., Windowing Design and Performance Assessment for Mitigation of Spectrum Leakage. E3S Web of Conferences, EDP Sciences. Jan. 1, 2019 ;94: 1-8.
Mair et al., 3He Lung Imaging in an Open Access, Very-Low-Field Human MRI System. Magnetic Resonance in Medicine as a Communication. Dec. 16, 2004. 19 pages.
Makeig, Mind Monitoring via Mobile Brain-body Imaging. HCI. 2009;16:749-59.
Non-Final Rejection for U.S. Appl. No. 16/417,345 dated Apr. 12, 2021.
Ruset et al., A System for Open-Access 3He Human Lung Imaging at Very Low Field. Concepts Magn Reson Part B Magn Reson Eng. 2006;29(4):210-21. doi:10.1002/cmr.b.20075. [Author Manuscript] 22 pages.
Tokuda et al., Smartphone Interface for Interactive MRI. CARS congress 2012. Jun. 1, 2012:4 pages.
Tsai et al., An open-access, very-low-field MRI system for posture-dependent 3He human lung imaging. J Magn Reson. Aug. 2008;193(2):274-285. doi:10.1016/j.jmr.2008.05.016.
EP 21205232.8, Jan. 25, 2022, Extended European Search Report.
Extended European Search Report for European Application No. EP 17872998.4 dated Apr. 24, 2020.
International Search Report and Written Opinion for International Application No. PCT/US2017/62763 dated Apr. 5, 2018.
Invitation to Pay Additional Fees for International Application No. PCT/US2017/62763 dated Feb. 5, 2018.
Adnan et al., Intracerebral haemorrhage. The Lancet. 2009;373(9675):1632-44.
Albayrak et al., Intra-operative magnetic resonance imaging in neurosurgery. Acta Neurochirurgica. 2004;146(6):543-57.
Bosc et al., Automatic change detection in multimodal serial MRI: application to multiple sclerosis lesion evolution. NeuroImage. Oct. 1, 2003;20(2):643-56.
Chalela et al., Magnetic resonance imaging and computed tomography in emergency assessment of patients with suspected acute stroke: a prospective comparison. The Lancet. 2007;369(9558):293-8.
Chen et al., Automated Midline Shift and Intracranial Pressure Estimation based on Brain CT Images. J Vis Exp. 2013;74(3871):1-8.
Elliott et al., The Acute Management of Intracerebral Hemorrhage: A Clinical Review. 2010;110(5):1419-27.
Ganiler et al., A subtraction pipeline for automatic detection of new appearing multiple sclerosis lesions in longitudinal studies. Diagnostic Neuroradiology. Mar. 4, 2014;56(5):363-74.
Kidwell et al., Comparison of MRI and CT for Detection of Acute Intracerebral Hemorrhage. JAMA. 2004;292(15):1823-1830. doi:10.1001/jama.292.15.1823.
Kidwell et al., Imaging of intracranial haemorrhage. The Lancet. 2008;7(3):256-7.
Kothari et al., The ABCs of measuring intracerebral hemorrhage volumes. Stroke. Aug. 1996;27(8):1304-5.
Liu et al., Automatic detection and quantification of brain midline shift using anatomical marker model. Computerized Medical Imaging and Graphics. 2014;38(1):1-14.
Llado et al., Segmentation of multiple sclerosis lesions in brain MRI: a review of automated approaches. Information Sciences. Mar. 1, 2012;186(1):164-85.
Qi et al., Automated Analysis of CT Slices for Detection of Ideal Midline from Brain CT Scans. ICCGI 2013: The Eighth International Multi-Conference on Computing in the Global Information Technology. 2013:117-21.
Sofka et al., Fully Convolutional Regression Network for Accurate Detection of Measurement Points. Springer International. 2017:258-66.

\* cited by examiner

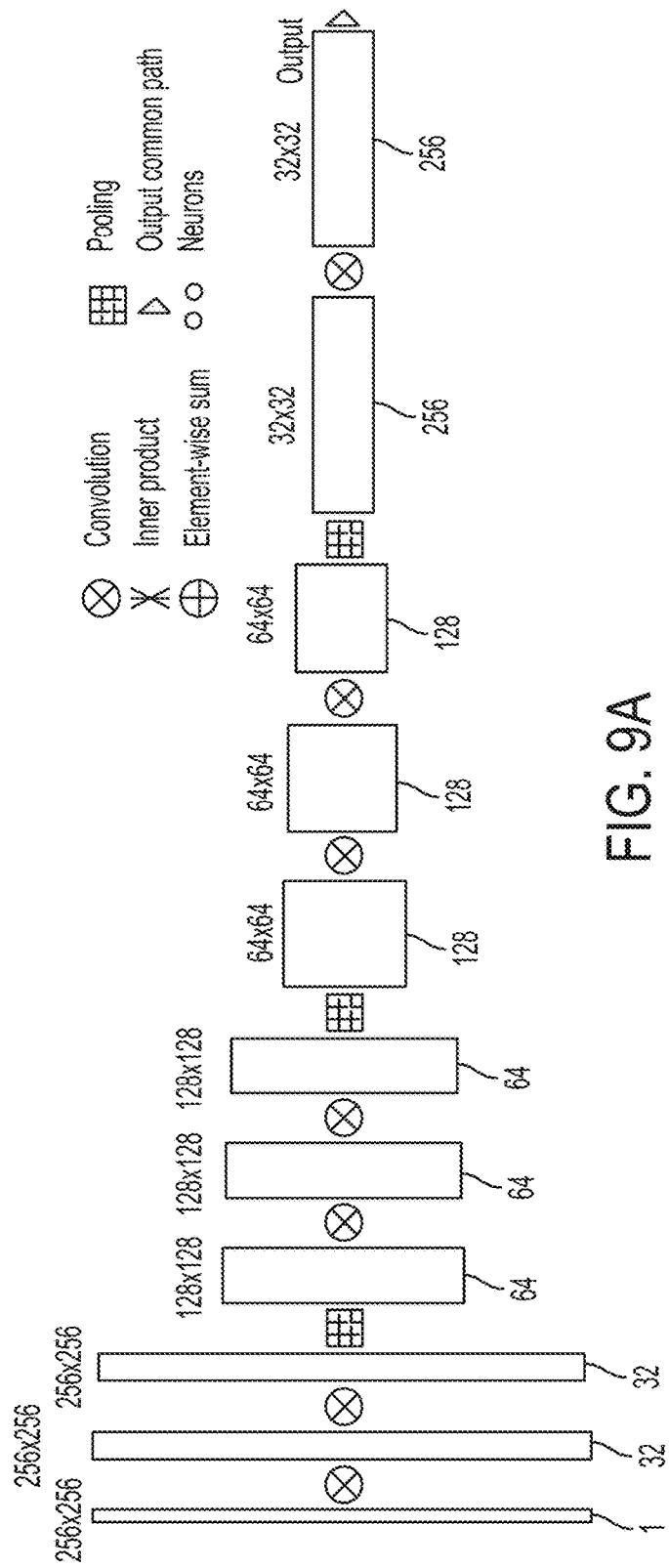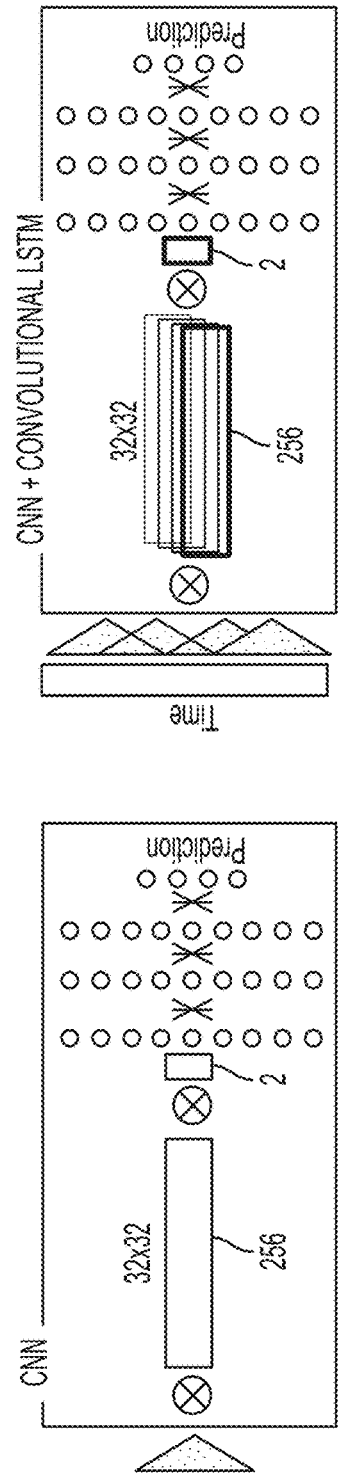
FIG. 9A
FIG. 9B
FIG. 9C

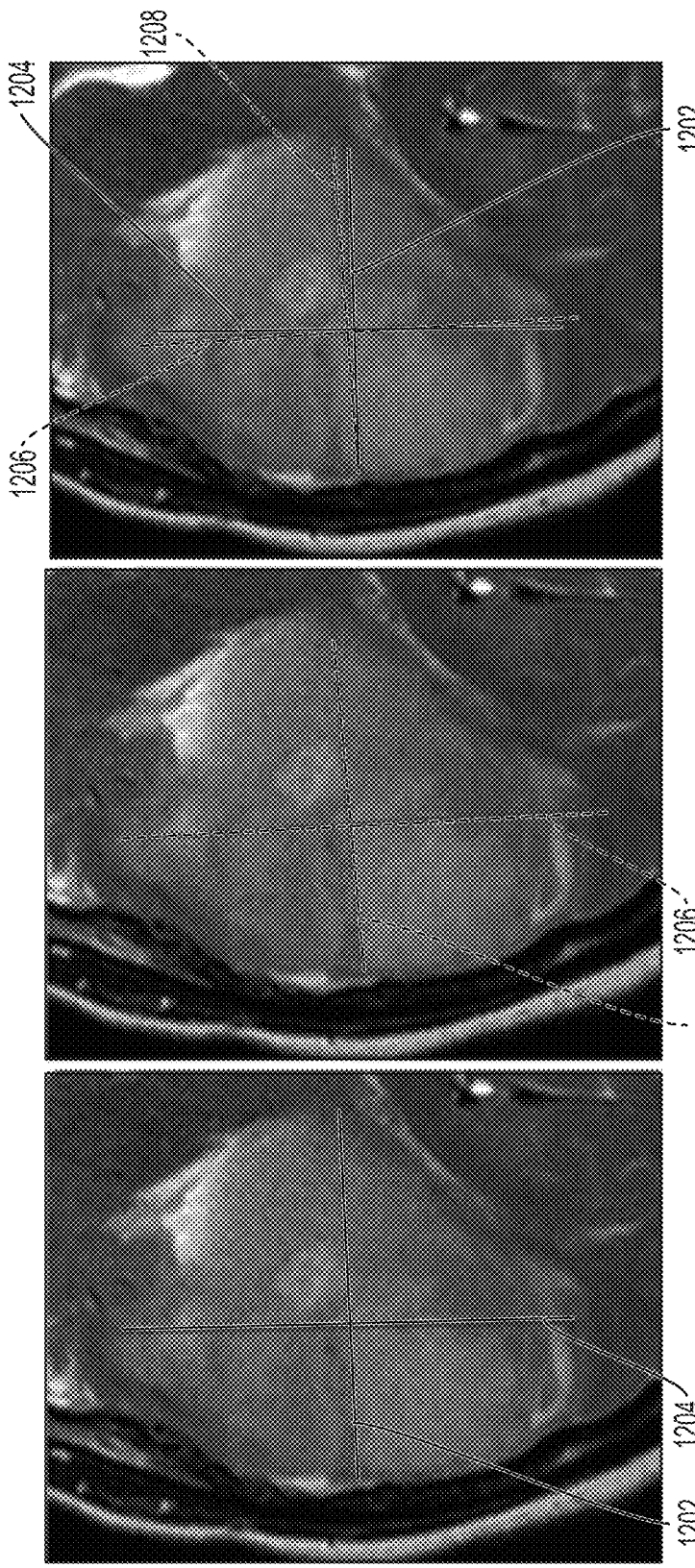

SYSTEMS AND METHODS FOR AUTOMATED DETECTION IN MAGNETIC RESONANCE IMAGES

CROSS REFERENCE TO RELATED APPLICATIONS

This application claims the benefit under 35 U.S.C. § 120 and is a continuation of U.S patent application Ser. No. 15/820,182, titled "SYSTEMS AND METHODS FOR AUTOMATED DETECTION IN MAGNETIC RESONANCE IMAGES", filed Nov. 21, 2017, which claims the benefit under 35 U.S.C. § 119(e) of U.S. Provisional Application Ser. No. 62/425,569, titled "CHANGE DETECTION METHODS AND APPARATUS", filed on Nov. 22, 2016, which is incorporated by reference in its entirety.

BACKGROUND

Magnetic resonance imaging (MRI) provides an important imaging modality for numerous applications and is widely utilized in clinical and research settings to produce images of the inside of the human body. MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to its ability to produce non-invasive images having relatively high resolution and contrast without the safety concerns of other modalities (e.g., without needing to expose the subject to ionizing radiation, such as x-rays, or introducing radioactive material into the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to conventional MRI techniques that, for a given imaging application, may include the relatively high cost of the equipment, limited availability (e.g., difficulty and expense in gaining access to clinical MRI scanners), the length of the image acquisition process, etc.

The trend in clinical MRI has been to increase the field strength of MRI scanners to improve one or more of scan time, image resolution, and image contrast, which in turn drives up costs of MRI imaging. The vast majority of installed MRI scanners operate using at least at 1.5 or 3 tesla (T), which refers to the field strength of the main magnetic field B0 of the scanner. A rough cost estimate for a clinical MRI scanner is on the order of one million dollars per tesla, which does not even factor in the substantial operation, service, and maintenance costs involved in operating such MRI scanners.

Additionally, conventional high-field MRI systems typically require large superconducting magnets and associated electronics to generate a strong uniform static magnetic field (B0) in which a subject (e.g., a patient) is imaged. Superconducting magnets further require cryogenic equipment to keep the conductors in a superconducting state. The size of such systems is considerable with a typical MRI installment including multiple rooms for the magnetic components, electronics, thermal management system, and control console areas, including a specially shielded room to isolate the magnetic components of the MRI system. The size and expense of MRI systems generally limits their usage to facilities, such as hospitals and academic research centers, which have sufficient space and resources to purchase and maintain them. The high cost and substantial space requirements of high-field MRI systems results in limited availability of MRI scanners. As such, there are frequently clinical situations in which an MRI scan would be beneficial, but is impractical or impossible due to the above-described limitations and as discussed in further detail below.

SUMMARY

Some embodiments are directed to a method of detecting change in degree of midline shift in a brain of a patient positioned within a low-field magnetic resonance imaging (MRI) device, the method comprising: while the patient remains positioned within the low-field MRI device: acquiring first magnetic resonance (MR) image data of the patient's brain; providing the first MR data as input to a trained statistical classifier to obtain corresponding first output; identifying, from the first output, at least one initial location of at least one landmark associated with at least one midline structure of the patient's brain; acquiring second MR image data of the patient's brain subsequent to acquiring the first MR image data; providing the second MR image data as input to the trained statistical classifier to obtain corresponding second output; identifying, from the second output, at least one updated location of the at least one landmark associated with the at least one midline structure of the patient's brain; and determining a degree of change in the midline shift using the at least one initial location of the at least one landmark and the at least one updated location of the at least one landmark.

Some embodiments are directed to a low-field magnetic resonance imaging device configured to detect change in degree of midline shift in a brain of a patient positioned within a low-field magnetic resonance imaging (MRI) device, the low-field MRI device comprising: a plurality of magnetic components, including: a B0 magnet configured to produce, at least in part, a B0 magnetic field; at least one gradient magnet configured to spatially encode magnetic resonance data; and at least one radio frequency coil configured to stimulate a magnetic resonance response and detect magnetic components configured to, when operated, acquire magnetic resonance image data; and at least one controller configured to operate the plurality of magnet components to, while the patient remains positioned within the low-field magnetic resonance device, acquire first magnetic resonance (MR) image data of the patient's brain, and acquire second MR image data of the patient's brain subsequent to acquiring the first MR image data, wherein the at least one controller further configured to perform: providing the first and second MR data as input to a trained statistical classifier to obtain corresponding first output and second output; identifying, from the first output, at least one initial location of at least one landmark associated with at least one midline structure of the patient's brain; identifying, from the second output, at least one updated location of the at least one landmark associated with the at least one midline structure of the patient's brain; and determining a degree of change in the midline shift using the at least one initial location of the at least one landmark and the at least one updated location of the at least one landmark.

Some embodiments are directed to at least one non-transitory computer-readable storage medium storing processor-executable instructions that, when executed by at least one computer hardware processor, cause the at least one computer hardware processor to perform a method of detecting change in degree of midline shift in a brain of a patient positioned within a low-field magnetic resonance imaging (MRI) device. The method comprises, while the patient remains positioned within the low-field MRI device, acquiring first magnetic resonance (MR) image data of the patient's brain; providing the first MR data as input to a trained statistical classifier to obtain corresponding first output; identifying, from the first output, at least one initial location of at least one landmark associated with at least one midline structure of the patient's brain; acquiring second MR image data of the patient's brain subsequent to acquiring the first MR image data; providing the second MR image data as input to the trained statistical classifier to obtain corresponding second output; identifying, from the second output, at least one updated location of the at least one landmark associated with the at least one midline structure of the patient's brain; and determining a degree of change in the midline shift using the at least one initial location of the at least one landmark and the at least one updated location of the at least one landmark.

Some embodiments are directed to a system comprising: at least one computer hardware processor; and at least one non-transitory computer-readable storage medium storing processor-executable instructions that, when executed by the at least one computer hardware processor, cause the at least one computer hardware processor to perform a method of detecting change in degree of midline shift in a brain of a patient positioned within a low-field magnetic resonance imaging (MRI) device. The method comprises, while the patient remains positioned within the low-field MRI device, acquiring first magnetic resonance (MR) image data of the patient's brain; providing the first MR data as input to a trained statistical classifier to obtain corresponding first output; identifying, from the first output, at least one initial location of at least one landmark associated with at least one midline structure of the patient's brain; acquiring second MR image data of the patient's brain subsequent to acquiring the first MR image data; providing the second MR image data as input to the trained statistical classifier to obtain corresponding second output; identifying, from the second output, at least one updated location of the at least one landmark associated with the at least one midline structure of the patient's brain; and determining a degree of change in the midline shift using the at least one initial location of the at least one landmark and the at least one updated location of the at least one landmark.

Some embodiments are directed to a method of determining change in size of an abnormality in a brain of a patient positioned within a low-field magnetic resonance imaging (MRI) device, the method comprising: while the patient remains positioned within the low-field MRI device: acquiring first magnetic resonance (MR) image data of the patient's brain; providing the first MR image data as input to a trained statistical classifier to obtain corresponding first output; identifying, using the first output, at least one initial value of at least one feature indicative of a size of an abnormality in the patient's brain; acquiring second MR image data of the patient's brain subsequent to acquiring the first MR image data; providing the second MR image data as input to the trained statistical classifier to obtain corresponding second output; identifying, using the second output, at least one updated value of the at least one feature indicative of the size of the abnormality in the patient's brain; determining the change in the size of the abnormality using the at least one initial value of the at least one feature and the at least one updated value of the at least one feature.

Some embodiments are directed to a low-field magnetic resonance imaging (MRI) device configured to determine change in size of an abnormality in a brain of a patient, the low-field MRI device comprising: a plurality of magnetic components, including: a B0 magnet configured to produce, at least in part, a B0 magnetic field; at least one gradient magnet configured to spatially encode magnetic resonance data; and at least one radio frequency coil configured to stimulate a magnetic resonance response and detect magnetic components configured to, when operated, acquire magnetic resonance image data; and at least one controller configured to operate the plurality of magnet components to, while the patient remains positioned within the low-field magnetic resonance device, acquire first magnetic resonance (MR) image data of the patient's brain, and acquire second MR image data of the patient's brain subsequent to acquiring the first MR image data, wherein the at least one controller further configured to perform: providing the first and second MR image data as input to a trained statistical classifier to obtain corresponding first output and second output; identifying, using the first output, at least one initial value of at least one feature indicative of a size of an abnormality in the patient's brain; acquiring second MR image data for the portion of the patient's brain subsequent to acquiring the first MR image data; identifying, using the second output, at least one updated value of the at least one feature indicative of the size of the abnormality in the patient's brain; determining the change in the size of the abnormality using the at least one initial value of the at least one feature and the at least one updated value of the at least one feature.

Some embodiments are directed to at least one non-transitory computer-readable storage medium storing processor-executable instructions that, when executed by at least one computer hardware processor, cause the at least one computer hardware processor, to perform method of determining change in size of an abnormality in a brain of a patient positioned within a low-field magnetic resonance imaging (MRI) device, the method comprising: while the patient remains positioned within the low-field MRI device: acquiring first magnetic resonance (MR) image data of the patient's brain; providing the first MR image data as input to a trained statistical classifier to obtain corresponding first output; identifying, using the first output, at least one initial value of at least one feature indicative of a size of an abnormality in the patient's brain; acquiring second MR image data of the patient's brain subsequent to acquiring the first MR image data; providing the second MR image data as input to the trained statistical classifier to obtain corresponding second output; identifying, using the second output, at least one updated value of the at least one feature indicative of the size of the abnormality in the patient's brain; determining the change in the size of the abnormality using the at least one initial value of the at least one feature and the at least one updated value of the at least one feature.

Some embodiments are directed to a system, comprising: at least one computer hardware processor; at least one non-transitory computer-readable storage medium storing processor-executable instructions that, when executed by the at least one computer hardware processor, cause the at least one computer hardware processor, to perform method of determining change in size of an abnormality in a brain of a patient positioned within a low-field magnetic resonance imaging (MRI) device. The method comprises, while the patient remains positioned within the low-field MRI device, acquiring first magnetic resonance (MR) image data of the patient's brain; providing the first MR image data as input to a trained statistical classifier to obtain corresponding first output; identifying, using the first output, at least one initial value of at least one feature indicative of a size of an abnormality in the patient's brain; acquiring second MR image data of the patient's brain subsequent to acquiring the first MR image data; providing the second MR image data as input to the trained statistical classifier to obtain corresponding second output; identifying, using the second output, at least one updated value of the at least one feature indicative of the size of the abnormality in the patient's brain; and determining the change in the size of the abnormality using the at least one initial value of the at least one feature and the at least one updated value of the at least one feature.

Some embodiments are directed to a method of detecting change in biological subject matter of a patient positioned within a low-field magnetic resonance imaging (MRI) device, the method comprising: while the patient remains positioned within the low-field MRI device: acquiring first magnetic resonance image data of a portion of the patient; acquiring second magnetic resonance image data of the portion of the patient subsequent to acquiring the first magnetic resonance image data; aligning the first magnetic resonance image data and the second magnetic resonance image data; and comparing the aligned first magnetic resonance image data and second magnetic resonance image data to detect at least one change in the biological subject matter of the portion of the patient.

Some embodiments are directed to a low-field magnetic resonance imaging device configured to detecting change in biological subject matter of a patient positioned with the low-field magnetic resonance imaging device, comprising: a plurality of magnetic components, including: a B0 magnet configured to produce, at least in part, a B0 magnetic field; at least one gradient magnet configured to spatially encode magnetic resonance data; and at least one radio frequency coil configured to stimulate a magnetic resonance response and detect magnetic components configured to, when operated, acquire magnetic resonance image data; and at least one controller configured to operate the plurality of magnet components to, while the patient remains positioned within the low-field magnetic resonance device, acquire first magnetic resonance image data of a portion of the patient, and acquire second magnetic resonance image data of the portion of the patient subsequent to acquiring the first magnetic resonance image data, the at least one controller further configured to align the first magnetic resonance image data and the second magnetic resonance image data, and compare the aligned first magnetic resonance image data and second magnetic resonance image data to detect at least one change in the biological subject matter of the portion of the patient.

Some embodiments are directed to at least one non-transitory computer-readable storage medium storing processor-executable instructions that, when executed by at least one computer hardware processor, cause the at least one computer hardware processor to perform a method of detecting change in biological subject matter of a patient positioned within a low-field magnetic resonance imaging (MRI) device, the method comprising: while the patient remains positioned within the low-field MRI device: acquiring first magnetic resonance image data of a portion of the patient; acquiring second magnetic resonance image data of the portion of the patient subsequent to acquiring the first magnetic resonance image data; aligning the first magnetic resonance image data and the second magnetic resonance image data; and comparing the aligned first magnetic resonance image data and second magnetic resonance image data to detect at least one change in the biological subject matter of the portion of the patient.

Some embodiments are directed to a system, comprising: at least one computer hardware processor; and at least one non-transitory computer-readable storage medium storing processor-executable instructions that, when executed by the at least one computer hardware processor, cause the at least one computer hardware processor to perform a method of detecting change in biological subject matter of a patient positioned within a low-field magnetic resonance imaging (MRI) device, the method comprising: while the patient remains positioned within the low-field MRI device: acquiring first magnetic resonance image data of a portion of the patient; acquiring second magnetic resonance image data of the portion of the patient subsequent to acquiring the first magnetic resonance image data; aligning the first magnetic resonance image data and the second magnetic resonance image data; and comparing the aligned first magnetic resonance image data and second magnetic resonance image data to detect at least one change in the biological subject matter of the portion of the patient.

BRIEF DESCRIPTION OF THE DRAWINGS

Various aspects and embodiments of the disclosed technology will be described with reference to the following figures. It should be appreciated that the figures are not necessarily drawn to scale.

FIGS. 9A-C illustrate a convolutional neural network architectures for making midline shift measurements, in accordance with some embodiments of the technology described herein.

FIGS. 12A-C illustrate measurements that may be used to determine a change in the size of a hemorrhage of a patient, in accordance with some embodiments of the technology described herein.

DETAILED DESCRIPTION

Figure 1:
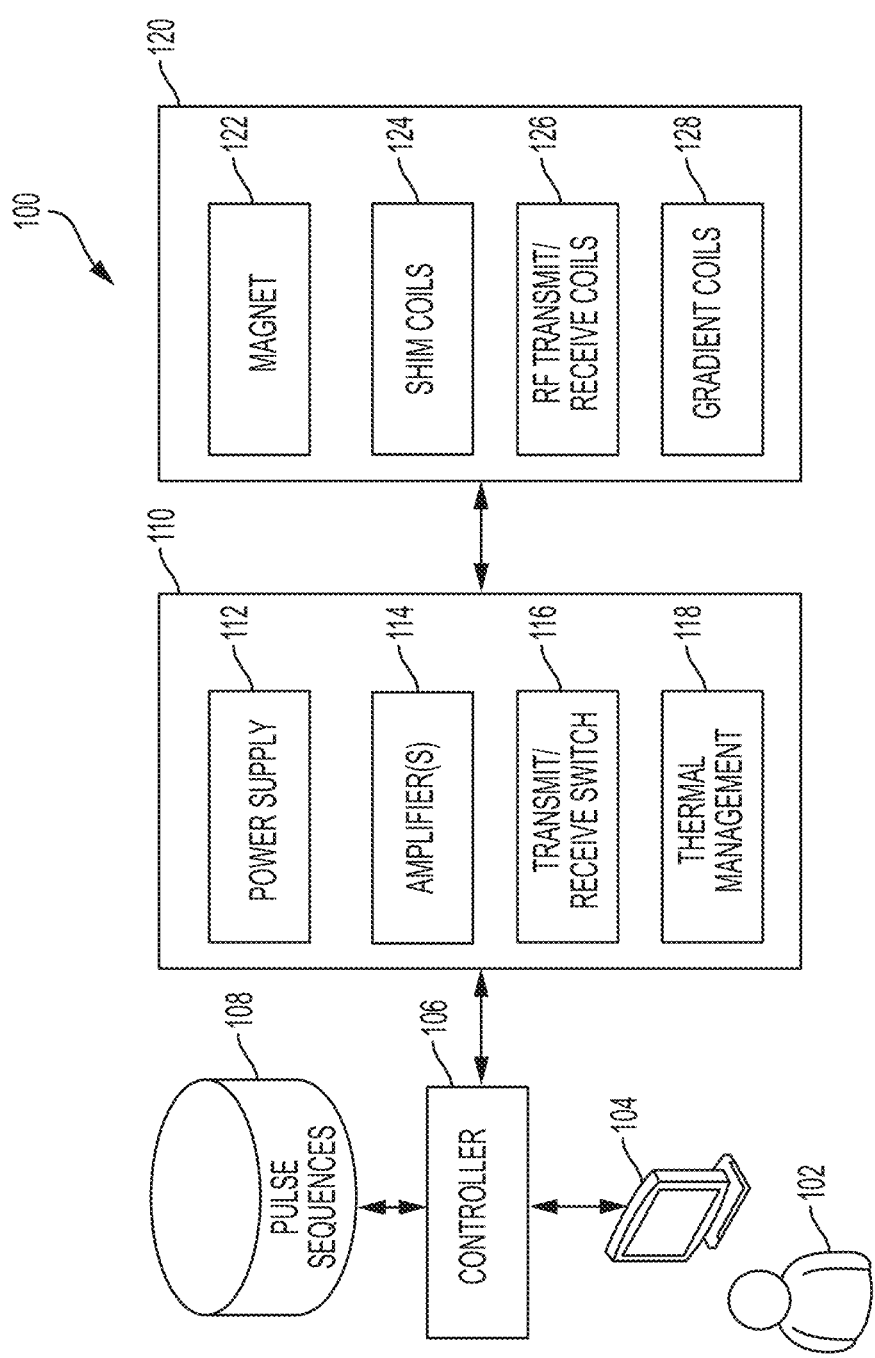
FIG. 1 is a schematic illustration of a low-field MRI system, in accordance with some embodiments of the technology described herein.

The MRI scanner market is overwhelmingly dominated by high-field systems, and particularly for medical or clinical MRI applications. As discussed above, the general trend in medical imaging has been to produce MRI scanners with increasingly greater field strengths, with the vast majority of clinical MRI scanners operating at 1.5 T or 3 T, with higher field strengths of 7 T and 9 T used in research settings. As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1 T have also been characterized as mid-field. By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI systems operating with a $B_0$ field of less than 0.1 T are referred to herein as "very low-field" and low-field MRI systems operating with a $B_0$ field of less than 10 mT are referred to herein as "ultra-low field."

As discussed above, conventional MRI systems require specialized facilities. An electromagnetically shielded room is required for the MRI system to operate and the floor of the room must be structurally reinforced. Additional rooms must be provided for the high-power electronics and the scan technician's control area. Secure access to the site must also be provided. In addition, a dedicated three-phase electrical connection must be installed to provide the power for the electronics that, in turn, are cooled by a chilled water supply. Additional HVAC capacity typically must also be provided. These site requirements are not only costly, but significantly limit the locations where MRI systems can be deployed. Conventional clinical MRI scanners also require substantial expertise to both operate and maintain. These highly trained technicians and service engineers add large on-going operational costs to operating an MRI system. Conventional MRI, as a result, is frequently cost prohibitive and is severely limited in accessibility, preventing MRI from being a widely available diagnostic tool capable of delivering a wide range of clinical imaging solutions wherever and whenever needed. Typically, patient must visit one of a limited number of facilities at a time and place scheduled in advance, preventing MRI from being used in numerous medical applications for which it is uniquely efficacious in assisting with diagnosis, surgery, patient monitoring and the like.

As discussed above, high-field MRI systems require specially adapted facilities to accommodate the size, weight, power consumption and shielding requirements of these systems. For example, a 1.5 T MRI system typically weighs between 4-10 tons and a 3 T MRI system typically weighs between 8-20 tons. In addition, high-field MRI systems generally require significant amounts of heavy and expensive shielding. Many mid-field scanners are even heavier, weighing between 10-20 tons due, in part, to the use of very large permanent magnets and/or yokes. Commercially available low-field MRI systems (e.g., operating with a $B_0$ magnetic field of 0.2 T) are also typically in the range of 10 tons or more due the large of amounts of ferromagnetic material used to generate the $B_0$ field, with additional tonnage in shielding. To accommodate this heavy equipment, rooms (which typically have a minimum size of 30-50 square meters) have to be built with reinforced flooring (e.g., concrete flooring), and must be specially shielded to prevent electromagnetic radiation from interfering with operation of the MRI system. Thus, available clinical MRI systems are immobile and require the significant expense of a large, dedicated space within a hospital or facility, and in addition to the considerable costs of preparing the space for operation, require further additional on-going costs in expertise in operating and maintaining the system.

In addition, currently available MRI systems typically consume large amounts of power. For example, common 1.5 T and 3 T MRI systems typically consume between 20-40 kW of power during operation, while available 0.5 T and 0.2 T MRI systems commonly consume between 5-20 kW, each using dedicated and specialized power sources. Unless otherwise specified, power consumption is referenced as average power consumed over an interval of interest. For example, the 20-40 kW referred to above indicates the average power consumed by conventional MRI systems during the course of image acquisition, which may include relatively short periods of peak power consumption that significantly exceeds the average power consumption (e.g., when the gradient coils and/or RF coils are pulsed over relatively short periods of the pulse sequence). Intervals of peak (or large) power consumption are typically addressed via power storage elements (e.g., capacitors) of the MRI system itself. Thus, the average power consumption is the more relevant number as it generally determines the type of power connection needed to operate the device. As discussed above, available clinical MRI systems must have dedicated power sources, typically requiring a dedicated three-phase connection to the grid to power the components of the MRI system. Additional electronics are then needed to convert the three-phase power into single-phase power utilized by the MRI system. The many physical requirements of deploying conventional clinical MRI systems creates a significant problem of availability and severely restricts the clinical applications for which MRI can be utilized.

Accordingly, the many requirements of high-field MRI render installations prohibitive in many situations, limiting their deployment to large institutional hospitals or specialized facilities and generally restricting their use to tightly scheduled appointments, requiring the patient to visit dedicated facilities at times scheduled in advance. Thus, the many restrictions on high field MRI prevent MRI from being fully utilized as an imaging modality. Despite the drawbacks of high-field MRI mentioned above, the appeal of the significant increase in SNR at higher fields continues to drive the industry to higher and higher field strengths for use in clinical and medical MRI applications, further increasing the cost and complexity of MRI scanners, and further limiting their availability and preventing their use as a general-purpose and/or generally-available imaging solution.

The inventors have developed techniques for producing improved quality, portable and/or lower-cost low-field MRI systems that can improve the wide-scale deployability of MRI technology in a variety of environments beyond the large MRI installments at hospitals and research facilities. The inventors have appreciated that the accessibility and availability of such low-field MRI systems (e.g., due to the relatively low cost, transportability, etc.) enables imaging applications not available or not practicable with other imaging modalities. For example, generally transportable low-field MRI systems may be brought to a patient to facilitate monitoring the patient over an extended period of time by acquiring a series of images and detecting changes occurring over the period of time. Such a monitoring procedure is not realistic with high-field MRI. In particular, as discussed above, high-field MRI installments are generally located in special facilities and require advanced scheduling at significant cost. Many patients (e.g., an unconscious Neural ICU patient) cannot be taken to an available facility and, even if a high-field MRI installment can be made available, the cost of an extended MRI analysis over the course of multiple hours is going to be prohibitively expensive.

Furthermore, while CT scanners are generally more available and accessible than high-field MRI systems, these systems still may not be available for relatively long monitoring applications to detect or monitor changes that the patient is undergoing over an extended period. Moreover, an extended CT examination subjects the patient to a significant dose of X-ray radiation, which may be unacceptable in many, if not most, circumstances. Finally, CT is limited in its ability to differentiate soft tissue and may be incapable of detecting the type of changes that may be of interest to a physician. The inventors have recognized that low-field MRI facilitates performing monitoring tasks in circumstances where current imaging modalities cannot do so.

The inventors have recognized that the transportability, accessibility and availability of low-field MRI systems permits monitoring applications that are not available using existing imaging modalities. For example, low-field MRI systems can be used to continuously and/or regularly image a portion of anatomy of interest to detect changes occurring therein. For example, in the neuro-intensive care unit (NICU), patients are often under general anesthesia for a significant amount of time while the patient is being assessed or during a procedure. Because of the need for a specialized facility, conventional clinical MRI systems are not available for these and many other circumstances. In addition, physicians may only have limited access to a computed tomography (CT) device for a patient (e.g., once a day). Moreover, even when such systems are available, it is inconvenient and sometimes impossible to image patients that are, for example, unconscious or otherwise not able to be transported to the MRI facility. Thus, conventional MRI is not typically used as a monitoring tool.

The inventors have recognized that low-field MRI can be used to monitor a patient by acquiring magnetic resonance (MR) image data over a period of time and detecting changes that occur. For example, a transportable low-field MRI system can be brought to a patient that can be positioned within the system while a sequence of images of the patient's brain is acquired. The acquired images can be aligned and differences between images can be detected to monitor any changes taking place. Image acquisition may be performed substantially continuously (e.g., with one acquisition immediately performed after another), regularly (e.g., with prescribed pauses in between acquisitions), or periodically according to a given acquisition schedule. As a result, a physician may obtain temporal information concerning physiology of interest. For example, the techniques described herein may be used to monitor a patient's brain to detect change in the degree of midline shift in the brain. As another example, the techniques described herein may be used to monitor a patient's brain to detect change in the size of an abnormality (e.g., a hemorrhage in the brain).

Accordingly, the inventors have developed low-field MRI techniques for monitoring a patient's brain for changes related to a brain injury, abnormality, etc. For example, the low-field MRI techniques described herein may be used to determine whether there is a change in a degree of midline shift for a patient. Midline shift refers to an amount of displacement of the brain's midline from its normal symmetric position due to trauma (e.g., stroke, hemorrhage, or other injury) and is an important indicator for clinicians of the severity of the brain trauma.

In some embodiments, low-field MRI monitoring techniques may be combined with machine learning techniques to continuously monitor the amount of midline displacement in a patient (if any) and detect a change in the degree of the midline shift over time. In such embodiments, low-field MRI monitoring allows for obtaining a sequence of images of a patient's brain and the machine learning techniques (e.g., deep learning techniques such as convolutional neural networks) may be used to determine, from the sequence of images, a corresponding sequence of locations of the brain's midline and/or a corresponding sequence of the midline's displacements from its normal position. For example, in some embodiments, deep learning techniques may be used to identify locations of the points where the falx cerebri is attached to the inner table of the patient's skull and a location of a measurement point in the septum pellucidum. These locations may in turn be used to obtain a midline shift measurement.

It should be appreciated, however, that although in some embodiments the midline is detected by detecting locations of the attachment points of the falx cerebri, there are other ways of detecting the midline. For example, in some embodiments, the midline may be detected by segmenting the left and right brain and the top and bottom part of the brain (as defined by the measurement plane).

In some embodiments, midline shift monitoring involves, while the patient remains positioned within a low-field MRI device: (1) acquiring first magnetic resonance (MR) image data for a portion of the patient's brain; (2) providing the first MR data as input to a trained statistical classifier (e.g., a convolutional neural network) to obtain corresponding first output; (3) identifying, from the first output, at least one initial location of at least one landmark associated with at least one midline structure of the patient's brain; (4) acquiring second MR image data for the portion of the patient's brain subsequent (e.g., within one hour) to acquiring the first MR image data; (5) providing the second MR image data as input to the trained statistical classifier to obtain corresponding second output; (6) identifying, from the second output, at least one updated location of the at least one landmark associated with the at least one midline structure of the patient's brain; and (7) determining a degree of change in the midline shift using the at least one initial location of the at least one landmark and the at least one updated location of the at least one landmark.

In some embodiments, the at least one landmark associated with the at last one midline structure of the patient's brain may include an anterior attachment point of the falx cerebri (to the interior table of the patient's skull), a posterior attachment point of the falx cerebri, a point on the septum pellucidum. In other embodiments, the at least one landmark may indicate results of segmentation of the left and right sides of brain and/or the top and bottom portions of the brain.

In some embodiments, identifying, from the first output of the trained statistical classifier, the at least one initial location of the at least one landmark associated with the at least one midline structure of the patient's brain includes: (1) identifying an initial location of an anterior attachment point of the falx cerebri; (2) identifying an initial location of a posterior attachment point of the falx cerebri; and (3) identifying an initial location of a measurement point on a septum pellucidum. Identifying, from the second output of the trained statistical classifier, the at least one updated location of the at least one landmark associated with the at least one midline structure of the patient's brain includes: (1) identifying an updated location of the anterior attachment point of the falx cerebri; (2) identifying an updated location of the posterior attachment point of the falx cerebri; and (3) identifying an updated location of the measurement point on the septum pellucidum. In turn, the degree of change in the midline shift may be performed using the identified initial and updated locations of the anterior attachment point of the falx cerebri, the posterior attachment point of the falx cerebri, and the measurement point on the septum pellucidum.

In some embodiments, determining the degree of change in the midline shift comprises: determining an initial amount of midline shift using the identified initial locations of the anterior attachment point of the falx cerebri, the posterior attachment point of the falx cerebri, and the measurement point on the septum pellucidum; determining an updated amount of midline shift using the identified updated locations of the anterior attachment point of the falx cerebri, the posterior attachment point of the falx cerebri, and the measurement point on the septum pellucidum; and determining the degree of change in the midline shift using the determined initial and updated amounts of midline shift.

In some embodiments, the trained statistical classifier may be a multi-layer neural network. For example, the multi-layer neural network may be a convolutional neural network (e.g., one having convolutional layers, pooling layers, and a fully connected layer) or a fully convolutional neural network (e.g., a convolutional neural network without a fully connected layer). As another example, the multi-layer neural network may include a convolutional and a recurrent (e.g., long short-term memory) neural network.

The inventors have also developed low-field MRI techniques for determining whether there is a change in the size of an abnormality (e.g., hemorrhage, a lesion, an edema, a stroke core, a stroke penumbra, and/or swelling) in a patient's brain. In some embodiments, low-field MRI monitoring techniques may be combined with machine learning techniques to continuously monitor the size of the abnormality and detect a change in its size over time. In such embodiments, low-field MRI monitoring allows for obtaining a sequence of images of a patient's brain and the machine learning techniques (e.g., deep learning techniques such as convolutional neural networks) may be used to determine, from the sequence of images, a corresponding sequence of sizes of the abnormality. For example, the deep learning techniques developed by the inventors may be used to segment the abnormality in MRI images, identify points that specify major axes of a 2D or 3D bounding region (e.g., box), identify maximum diameter of the abnormality and a maximum orthogonal diameter of the abnormality that is orthogonal to the maximum diameter, and/or perform any other processing in furtherance of identifying the size of the abnormality.

Accordingly, in some embodiments, abnormality size monitoring involves, while a patient is positioned within a low-field MRI device: (1) acquiring first magnetic resonance (MR) image data for a portion of the patient's brain; (2) providing the first MR image data as input to a trained statistical classifier (e.g., a multi-layer neural network, a convolutional neural network, a fully convolutional neural network) to obtain corresponding first output; (3) identifying, using the first output, at least one initial value of at least one feature indicative of a size of an abnormality in the patient's brain; (4) acquiring second MR image data for the portion of the patient's brain subsequent to acquiring the first MR image data; (5) providing the second MR image data as input to the trained statistical classifier to obtain corresponding second output; (5) identifying, using the second output, at least one updated value of the at least one feature indicative of the size of the abnormality in the patient's brain; (6) determining the change in the size of the abnormality using the at least one initial value of the at least one feature and the at least one updated value of the at least one feature.

Figures 11A, 11B:
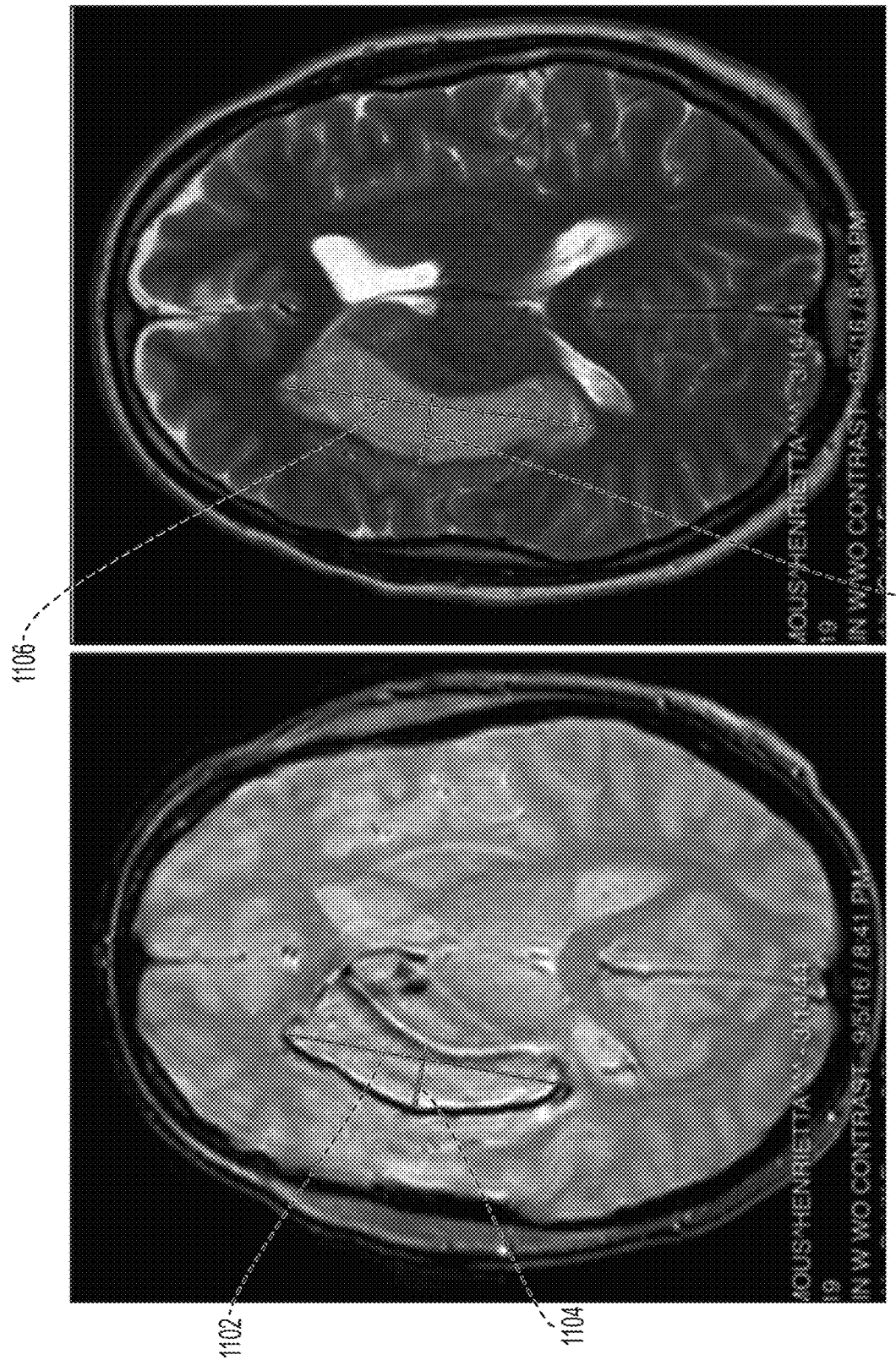
FIGS. 11A-11F illustrate measurements that may be used to determine the size of a hemorrhage of a patient, in accordance with some embodiments of the technology described herein.

In some embodiments, the at least one initial value of the at least one feature indicative of the size of the abnormality may include multiple values specifying a region surrounding the abnormality (e.g., values specifying a bounding region, values specifying the perimeter of the abnormality, etc.). In some embodiments, the at least one initial value of the at least one feature may include values specifying one or more diameters of the abnormality (e.g., diameters 1102 and diameter 1104 orthogonal to diameter 1102, as shown in FIG. 11A).

In some embodiments, determining the change in the size of the abnormality involves: (1) determining an initial size of the abnormality using the at least one value of the at least one feature; (2) determining an updated size of the abnormality using the at least one updated value of the at least one feature; and (3) determining the change in the size of the abnormality using the determined initial and updated sizes of the abnormality.

Following below are more detailed descriptions of various concepts related to, and embodiments of, methods and apparatus for performing monitoring using low-field magnetic resonance applications including low-field MRI. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 is a block diagram of exemplary components of a MRI system 100. In the illustrative example of FIG. 1, MRI system 100 comprises workstation 104, controller 106, pulse sequences store 108, power management system 110, and magnetic components 120. It should be appreciated that system 100 is illustrative and that a MRI system may have one or more other components of any suitable type in addition to or instead of the components illustrated in FIG. 1.

As illustrated in FIG. 1, magnetic components 120 comprises $B_0$ magnet 122, shim coils 124, RF transmit and receive coils 126, and gradient coils 128. $B_0$ magnet 122 may be used to generate, at least in part, the main magnetic field $B_0$. $B_0$ magnet 122 may be any suitable type of magnet that can generate a main magnetic field (e.g., a low-field strength of approximately 0.2 T or less), and may include one or more $B_0$ coils, correction coils, etc. Shim coils 124 may be used to contribute magnetic field(s) to improve the homogeneity of the $B_0$ field generated by magnet 122. Gradient coils 128 may be arranged to provide gradient fields and, for example, may be arranged to generate gradients in the magnetic field in three substantially orthogonal directions (X, Y, Z) to localize where MR signals are induced.

RF transmit and receive coils 126 may comprise one or more transmit coils that may be used to generate RF pulses to induce a magnetic field $B_1$. The transmit/receive coil(s) may be configured to generate any suitable type of RF pulses configured to excite an MR response in a subject and detect the resulting MR signals emitted. RF transmit and receive coils 126 may include one or multiple transmit coils and one or multiple receive coils. The configuration of the transmit/receive coils varies with implementation and may include a single coil for both transmitting and receiving, separate coils for transmitting and receiving, multiple coils for transmitting and/or receiving, or any combination to achieve single channel or parallel MRI systems. Thus, the transmit/receive magnetic component is often referred to as Tx/Rx or Tx/Rx coils to generically refer to the various configurations for the transmit and receive component of an MRI system. Each of magnetics components 120 may be constructed in any suitable way. For example, in some embodiments, one or more of magnetics components 120 may be fabricated using the laminate techniques described in the above incorporated co-filed applications.

Power management system 110 includes electronics to provide operating power to one or more components of the low-field MRI system 100. For example, power management system 110 may include one or more power supplies, gradient power amplifiers, transmit coil amplifiers, and/or any other suitable power electronics needed to provide suitable operating power to energize and operate components of the low-field MRI system 100.

As illustrated in FIG. 1, power management system 110 comprises power supply 112, amplifier(s) 114, transmit/receive switch 116, and thermal management components 118. Power supply 112 includes electronics to provide operating power to magnetic components 120 of the low-field MRI system 100. For example, power supply 112 may include electronics to provide operating power to one or more $B_0$ coils (e.g., $B_0$ magnet 122) to produce the main magnetic field for the low-field MRI system. In some embodiments, power supply 112 may be a unipolar, continuous wave (CW) power supply, however, any suitable power supply may be used. Transmit/receive switch 116 may be used to select whether RF transmit coils or RF receive coils are being operated.

Amplifier(s) 114 may include one or more RF receive (Rx) pre-amplifiers that amplify MR signals detected by one or more RF receive coils (e.g., coils 124), one or more RF transmit (Tx) amplifiers configured to provide power to one or more RF transmit coils (e.g., coils 126), one or more gradient power amplifiers configured to provide power to one or more gradient coils (e.g., gradient coils 128), shim amplifiers configured to provide power to one or more shim coils (e.g., shim coils 124).

Thermal management components 118 provide cooling for components of low-field MRI system 100 and may be configured to do so by facilitating the transfer of thermal energy generated by one or more components of the low-field MRI system 100 away from those components. Thermal management components 118 may include, without limitation, components to perform water-based or air-based cooling, which may be integrated with or arranged in close proximity to MRI components that generate heat including, but not limited to, $B_0$ coils, gradient coils, shim coils, and/or transmit/receive coils. Thermal management components 118 may include any suitable heat transfer medium including, but not limited to, air and water, to transfer heat away from components of the low-field MRI system 100.

As illustrated in FIG. 1, low-field MRI system 100 includes controller 106 (also referred to as a console) having control electronics to send instructions to and receive information from power management system 110. Controller 106 may be configured to implement one or more pulse sequences, which are used to determine the instructions sent to power management system 110 to operate the magnetic components 120 in a desired sequence. For example, controller 106 may be configured to control power management system 110 to operate the magnetic components 120 in accordance with a balance steady-state free precession (bSSFP) pulse sequence, a low-field gradient echo pulse sequence, a low-field spin echo pulse sequence, a low-field inversion recovery pulse sequence, arterial spin labeling, diffusion weighted imaging (DWI), and/or any other suitable pulse sequence. Controller 106 may be implemented as hardware, software, or any suitable combination of hardware and software, as aspects of the disclosure provided herein are not limited in this respect.

In some embodiments, controller 106 may be configured to implement a pulse sequence by obtaining information about the pulse sequence from pulse sequences repository 108, which stores information for each of one or more pulse sequences. Information stored by pulse sequences repository 108 for a particular pulse sequence may be any suitable information that allows controller 106 to implement the particular pulse sequence. For example, information stored in pulse sequences repository 108 for a pulse sequence may include one or more parameters for operating magnetics components 120 in accordance with the pulse sequence (e.g., parameters for operating the RF transmit and receive coils 126, parameters for operating gradient coils 128, etc.), one or more parameters for operating power management system 110 in accordance with the pulse sequence, one or more programs comprising instructions that, when executed by controller 106, cause controller 106 to control system 100 to operate in accordance with the pulse sequence, and/or any other suitable information. Information stored in pulse sequences repository 108 may be stored on one or more non-transitory storage media.

As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information.

Computing device 104 may be any electronic device that may process acquired MR data and generate one or more images of the subject being imaged. In some embodiments, computing device 104 may be a fixed electronic device such as a desktop computer, a server, a rack-mounted computer, or any other suitable fixed electronic device that may be configured to process MR data and generate one or more images of the subject being imaged. Alternatively, computing device 104 may be a portable device such as a smart phone, a personal digital assistant, a laptop computer, a tablet computer, or any other portable device that may be configured to process MR data and generate one or images of the subject being imaged. In some embodiments, computing device 104 may comprise multiple computing devices of any suitable type, as the aspects are not limited in this respect. A user 102 may interact with workstation 104 to control aspects of the low-field MR system 100 (e.g., program the system 100 to operate in accordance with a particular pulse sequence, adjust one or more parameters of the system 100, etc.) and/or view images obtained by the low-field MR system 100. According to some embodiments, computing device 104 and controller 106 form a single controller, while in other embodiments, computing device 104 and controller 106 each comprise one or more controllers. It should be appreciated that the functionality performed by computing device 104 and controller 106 may be distributed in any way over any combination of one or more controllers, as the aspects are not limited for use with any particular implementation or architecture.

Figure 2A:
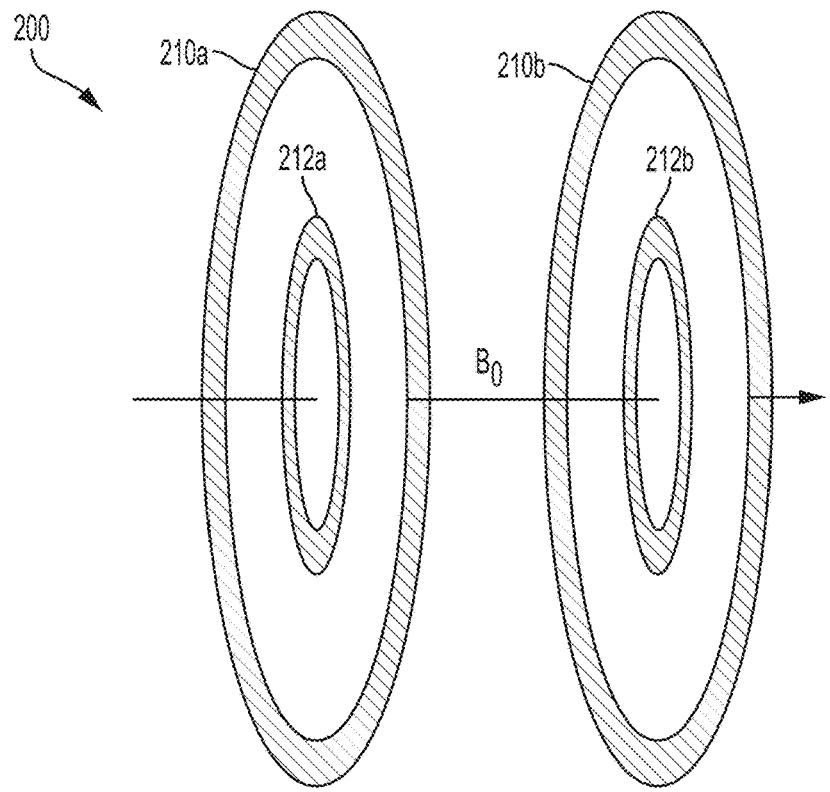
FIGS. 2A and 2B illustrate bi-planar magnet configurations for a $B_0$ magnet, in accordance with some embodiments of the technology described herein.
Figure 2B:
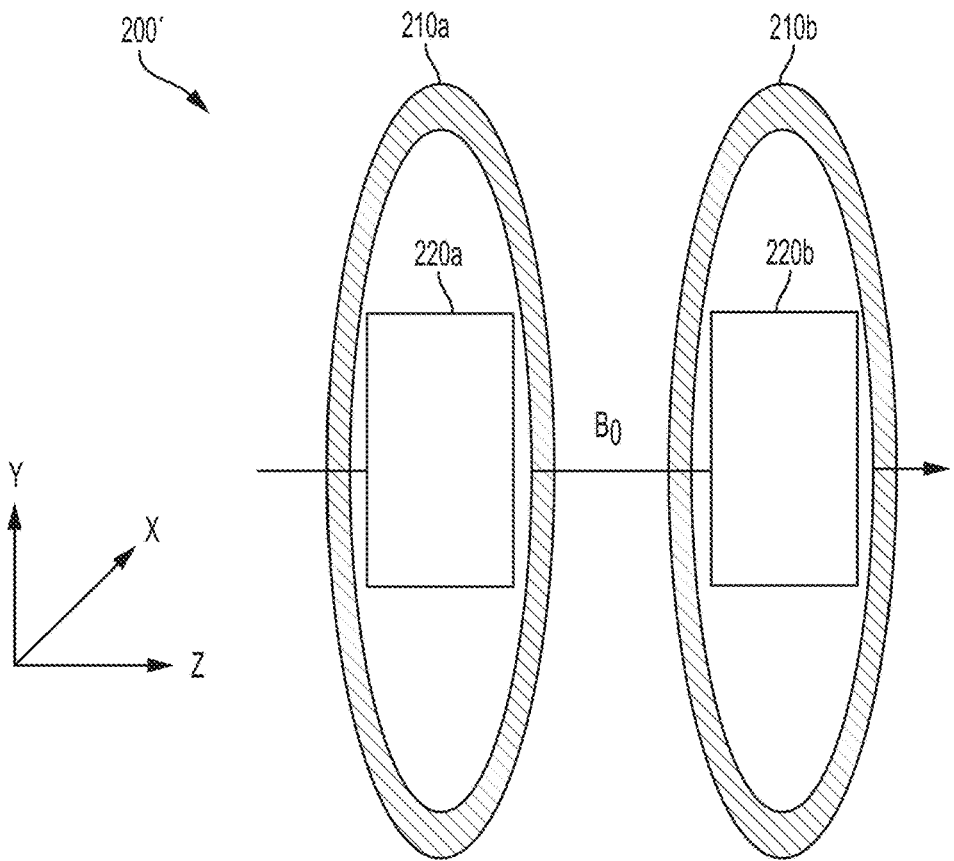

FIGS. 2A and 2B illustrate bi-planar magnetic configurations that may be used in a low-field MRI system suitable for use with the change detection techniques described herein. FIG. 2A schematically illustrates a bi-planar magnet configured to produce, at least in part, a portion of a $B_0$ field suitable for low-field MRI. Bi-planar magnet 200 comprises two outer coils 210a and 210b and two inner coils 212a and 212b. When appropriate current is applied to the coils, a magnetic field is generated in the direction indicated by the arrow to produce a $B_0$ field having a field of view between the coils that, when designed and constructed appropriately, may be suitable for low-field MRI. The term "coil" is used herein to refer to any conductor or combination of conductors of any geometry having at least one "turn" that conducts current to produce a magnetic field, thereby forming an electromagnet.

It should be appreciated that the bi-planar geometry illustrated in FIG. 2A is generally unsuitable for high-field MRI due to the difficulty in obtaining a $B_0$ field of sufficient homogeneity at high-field strengths. High-field MRI systems typically utilize solenoid geometries (and superconducting wires) to achieve the high field strengths of sufficient homogeneity for high-field MRI. The bi-planar $B_0$ magnet illustrated in FIG. 2A provides a generally open geometry, facilitating its use with patients who suffer from claustrophobia and may refuse to be imaged with conventional high-field solenoid coil geometries. Furthermore, the bi-planar design may facilitate use with larger patients as a result of its open design and, in some instances, a generally larger field of view possible at low-field strengths and homogeneity requirements. Moreover, the generally open design facilitates access to the patient being imaged and may improve the ability to position a patient within the field of view, for example, an unconscious, sedated or anesthetized patient, as discussed in further detail below. The bi-planar geometry in FIG. 2A is merely exemplary, as more or fewer coils may be arranged as needed, as the aspects are not limited in this respect.

FIG. 2B illustrates a hybrid bi-planar magnet using laminate techniques to fabricate a $B_0$ magnet or portion thereof and/or to fabricate one or more other magnetic components for use in low-field MRI. For example, in the exemplary bi-planar magnet 200' illustrated in FIG. 2B, laminate panels 220a and 220b replace inner coils 212a and 212b to produce a hybrid magnet. Laminate panels 220a and 220b may include any number of laminate layers having fabricated thereon one or more $B_0$ coils, gradient coils, correction coils and/or shim coils, etc. or portions thereof to facilitate production of the magnetic fields used in low-field MRI. Suitable hybrid magnets using laminate techniques are described in U.S. patent application Ser. No. 14/845,652 ('652 application), filed Sep. 4, 2015 and titled "Low Field Magnetic Resonance Imaging Methods and Apparatus," which is herein incorporated by reference in its entirety. In other embodiments, laminate techniques can be used to implement the $B_0$ magnet in its entirety (e.g., replacing coils 210a and 210b).

Exemplary laminate panels 220a and 220b may, additionally or alternatively, have fabricated thereon one or more gradient coils, or portions thereof, to encode the spatial location of received MR signals as a function of frequency or phase. According to some embodiments, a laminate panel comprises at least one conductive layer patterned to form one or more gradient coils, or a portion of one or more gradient coils, capable of producing or contributing to magnetic fields suitable for providing spatial encoding of detected MR signals when operated in a low-field MRI system. For example, laminate panel 220a and/or laminate panel 220b may comprise a first gradient coil configured to selectively vary the $B_0$ field in a first (X) direction to perform frequency encoding in that direction, a second gradient coil configured to selectively vary the $B_0$ field in a second (Y) direction substantially orthogonal to the first direction to perform phase encoding, and/or a third gradient coil configured to selectively vary the $B_0$ field in a third (Z) direction substantially orthogonal to the first and second directions to enable slice selection for volumetric imaging applications.

Exemplary laminate panels 220a and 220b may, additionally or alternatively, include additional magnetic components such as one or more shim coils arranged to generate magnetic fields in support of the system to, for example, increase the strength and/or improve the homogeneity of the $B_0$ field, counteract deleterious field effects such as those created by operation of the gradient coils, loading effects of the object being imaged, or to otherwise support the magnetics of the low field MRI system. The bi-planar magnet illustrated in FIGS. 2A and 2B, may be produced using conventional coils, laminate techniques, or a combination of both, and may be used to provide magnetic components for a low-field MRI system adapted to perform change detection techniques, as discussed in further detail below.

The inventors have recognized that the low-field context allows for $B_0$ magnet designs not feasible in the high-field regime. For example, due at least in part to the lower field strengths, superconducting material and the corresponding cryogenic cooling systems can be eliminated. Due in part to the low-field strengths, $B_0$ electromagnets constructed using non-superconducting material (e.g., copper) may be employed in the low-field regime. However, such electromagnets still may consume relatively large amounts of power during operation. For example, operating an electromagnet using a copper conductor to generate a magnetic field of 0.2 T or more requires a dedicated or specialized power connection (e.g., a dedicated three-phase power connection). The inventors have developed MRI systems that can be operated using mains electricity (i.e., standard wall power), allowing the MRI system to be powered at any location having common power connection, such as a standard wall outlet (e.g., 120V/20 A connection in the U.S.) or common large appliance outlets (e.g., 220-240V/30 A). Thus, a low-power MRI system facilitates portability and availability, allowing an MRI system to be operated at locations where it is needed (e.g., the MRI system can be brought to the patient instead of vice versa), examples of which are discussed in further detail below. In addition, operating from standard wall power eliminates the electronics conventionally needed to convert three-phase power to single-phase power and to smooth out the power provided directly from the grid. Instead, wall power can be directly converted to DC and distributed to power the components of the MRI system.

Figure 2C:
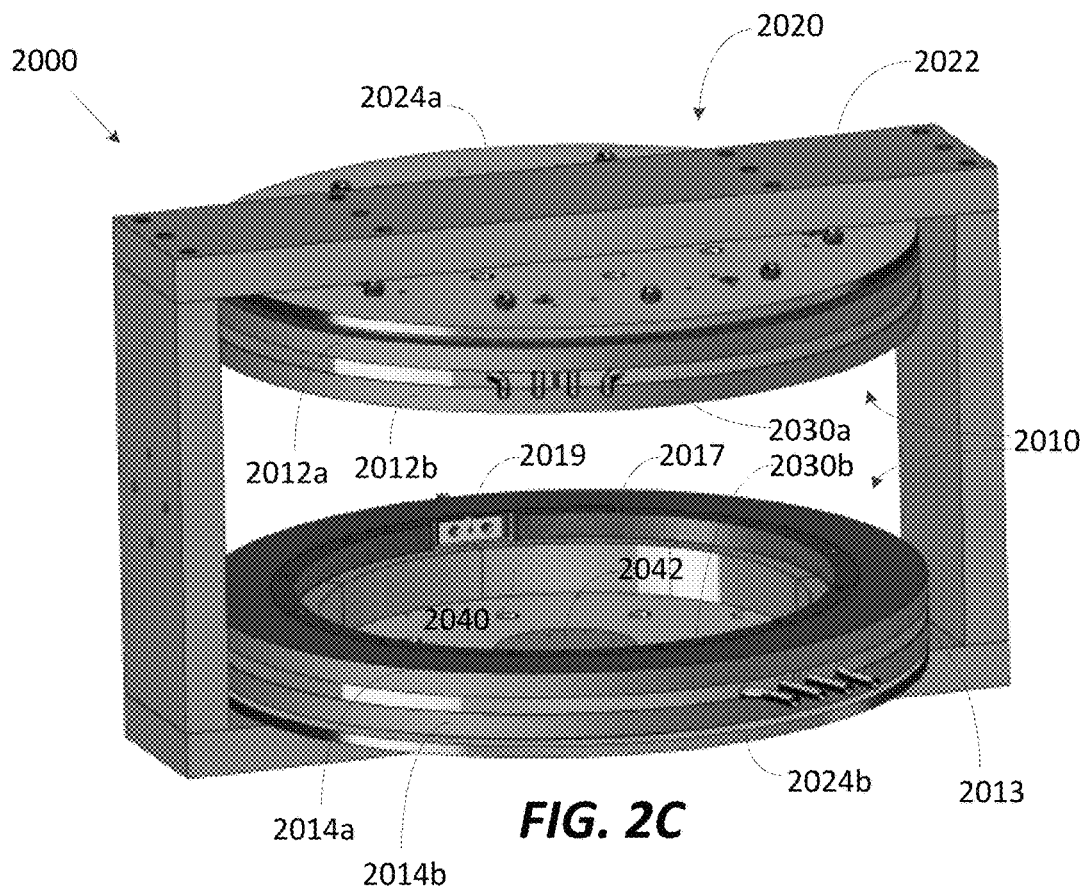
FIGS. 2C and 2D illustrate a bi-planar electromagnet configuration for a $B_0$ magnet, in accordance with some embodiments of the technology described herein.
Figure 2D:
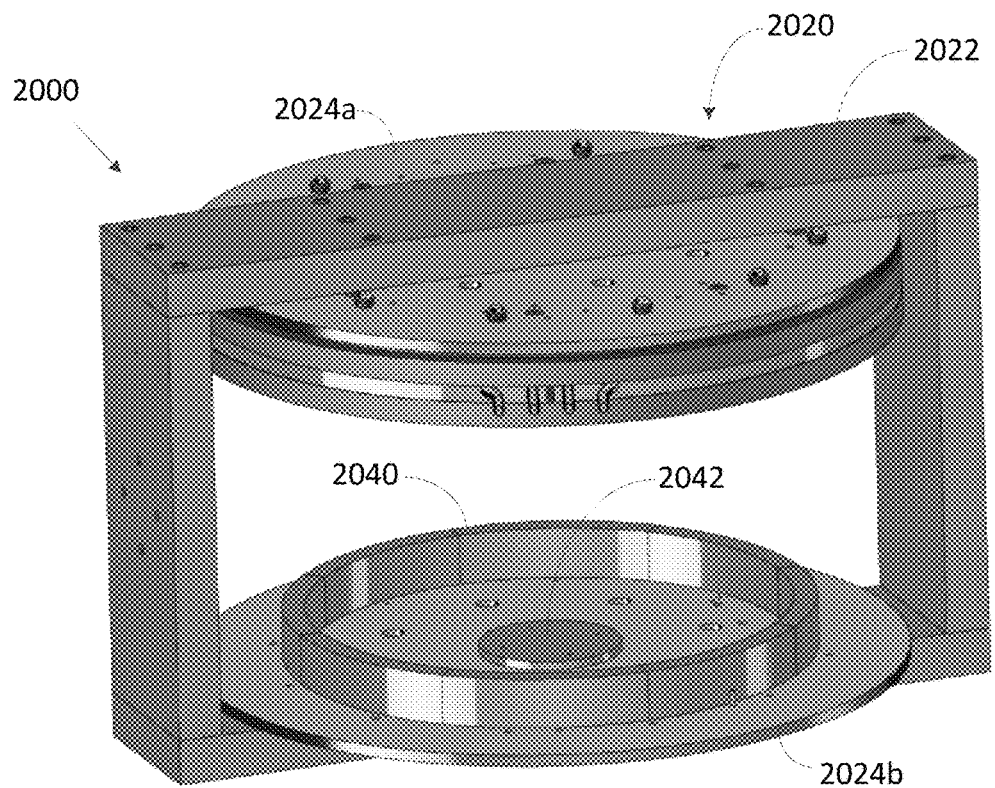

FIGS. 2C and 2D illustrate a $B_0$ magnet formed using an electromagnet and a ferromagnetic yoke. In particular, $B_0$ magnet 2000 is formed in part by an electromagnet 2010 arranged in a bi-planar geometry comprising electromagnetic coils 2012a and 2012b on an upper side and electromagnetic coils 2014a and 2014b on a lower side of $B_0$ magnet 2000. According to some embodiments, the coils forming electromagnet 2010 may be formed from a number of turns of a copper wire or copper ribbon, or any other conductive material suitable for producing a magnetic field when operated (e.g., when electrical current is driven through the conductor windings). While the exemplary electromagnet illustrated in FIGS. 2C and 2D comprises two pairs of coils, an electromagnet may be formed using any number of coils in any configuration, as the aspects are not limited in this respect. The electromagnetic coils forming electromagnet 2010 may be formed, for example, by winding a conductor 2013 (e.g., a copper ribbon, wire, paint, etc.) about a fiberglass ring 2017. For example, conductor 2013 may be a suitable insulated copper wire, or alternatively, conductor 2013 may be a copper ribbon wound in conjunction with an insulating layer (e.g., a Mylar layer) to electrically isolate the multiple windings of the coil. A connector 2019 may be provided to allow for a power connection to provide current to operate coils 2014a and 2014b in series. A similar connector on the upper side of the electromagnet (not visible in FIGS. 2C and 2D) may be provided to operate coils 2012a and 2012b.

It should be appreciated that the electromagnetic coils may be formed from any suitable material and dimensioned in any suitable way so as to produce or contribute to a desired $B_0$ magnetic field, as the aspects are not limited for use with any particular type of electromagnet. As one non-limiting example that may be suitable to form, in part, an electromagnet (e.g., electromagnet 2010), an electromagnetic coil may be constructed using copper ribbon and mylar insulator having 155 turns to form an inner diameter of approximately 23-27 inches (e.g., approximately 25 inches), an outer diameter of approximately 30-35 inches (e.g., 32 inches). However, different material and/or different dimensions may be used to construct an electromagnetic coil having desired characteristics, as the aspects are not limited in this respect. The upper and lower coil(s) may be positioned to provide a distance of approximately 10-15 inches (e.g., approximately 12.5 inches) between the lower coil on the upper side and the upper coil on the lower side. It should be appreciated that the dimensions will differ depending on the desired characteristics including, for example, field strength, field of view, etc.

In the exemplary $B_0$ magnet illustrated in FIGS. 2C and 2D, each coil pair 2012 and 2014 is separated by thermal management components 2030a and 2030b, respectively, to transfer heat produced by the electromagnetic coils and gradient coils (not illustrated in FIGS. 2C and 2D) away from the magnets to provide thermal management for the MRI device. In particular, thermal management components 2030a and 2030b may comprise a cooling plate having conduits that allow coolant to be circulated through the cooling plate to transfer heat away from the magnets. The cooling plate 2030a, 2030b may be constructed to reduce or eliminate eddy currents induced by operating the gradient coils that can produce electromagnetic fields that disrupt the $B_0$ magnetic field produced by the $B_0$ magnet 2000. For example, thermal management components 2030a and 2030b may be the same or similar to any of the thermal management components described in U.S. application Ser. No. 14/846,042 entitled "Thermal Management Methods and Apparatus," filed on Sep. 4, 2015, which is incorporated by reference herein in its entirety. According to some embodiments, thermal management components may be eliminated, as discussed in further detail below.

$B_0$ magnet 2000 further comprises a yoke 2020 that is magnetically coupled to the electromagnet to capture magnetic flux that, in the absence of yoke 2020, would be lost and not contribute to the flux density in the region of interest between the upper and lower electromagnetic coils. In particular, yoke 2020 forms a "magnetic circuit" connecting the coils on the upper and lower side of the electromagnet so as to increase the flux density in the region between the coils, thus increasing the field strength within the imaging region (also referred to as the field of view) of the $B_0$ magnet. The imaging region or field of view defines the volume in which the $B_0$ magnetic field produced by a given B0 magnet is suitable for imaging. More particularly, the imaging region or field of view corresponds to the region for which the $B_0$ magnetic field is sufficiently homogeneous at a desired field strength that detectable MR signals are emitted by an object positioned therein in response to application of radio frequency excitation (e.g., a suitable radio frequency pulse sequence). Yoke 2020 comprises frame 2022 and plates 2024a, 2024b, which may be formed using any suitable ferromagnetic material (e.g., iron, steel, etc.). Plates 2024a, 2024b collect magnetic flux generated by the coil pairs of electromagnet 2010 and directs it to frame 2022 which, in turn, returns the flux back to the opposing coil pair, thereby increasing, by up to a factor of two, the magnetic flux density in the imaging region between the coil pairs (e.g., coil pair 2012a, 2012b and coil pair 2014a, 2014b) for the same amount of operating current provided to the coils. Thus, yoke 2020 can be used to produce a higher $B_0$ field (resulting in higher SNR) without a corresponding increase in power requirements, or yoke 2020 can be used to lower the power requirements of $B_0$ magnet 2000 for a given $B_0$ field.

According to some embodiments, the material used for portions of yoke 2020 (i.e., frame 2022 and/or plates 2024a, 2024b) is steel, for example, a low-carbon steel, silicon steel, cobalt steel, etc. According to some embodiments, gradient coils (not shown in FIGS. 2C, 2D) of the MRI system are arranged in relatively close proximity to plates 2024a, 2024b inducing eddy currents in the plates. To mitigate, plates 2024a, 2024b and/or frame 2022 may be constructed of silicon steel, which is generally more resistant to eddy current production than, for example, low-carbon steel. It should be appreciated that yoke 2020 may be constructed using any ferromagnetic material with sufficient magnetic permeability and the individual parts (e.g., frame 2022 and plates 2024a, 2024b) may be constructed of the same or different ferromagnetic material, as the techniques of increasing flux density is not limited for use with any particular type of material or combination of materials. Furthermore, it should be appreciated that yoke 2020 can be formed using different geometries and arrangements.

It should be appreciated that the yoke 2020 may be made of any suitable material and may be dimensioned to provide desired magnetic flux capture while satisfying other design constraints such as weight, cost, magnetic properties, etc. As an example, the frame of the yoke (e.g., frame 2022) may be formed of a low-carbon steel of less than 0.2% carbon or silicon steel, with the long beam(s) having a length of approximately 38 inches, a width of approximately 8 inches, and a thickness (depth) of approximately 2 inches, and the short beam(s) having a length of approximately 19 inches, a width of approximately 8 inches and a thickness (depth) of approximately 2 inches. The plates (e.g., plates 2024a and 2024b) may be formed from a low-carbon steel of less than 0.2% carbon or silicon steel and have a diameter of approximately 30-35 inches (e.g., approximately 32 inches). However, the above provided dimensions and materials are merely exemplary of a suitable embodiment of a yoke that can be used to capture magnetic flux generated by an electromagnet.

As an example of the improvement achieved via the use of yoke 2020, operating electromagnet 2010 to produce a $B_0$ magnetic field of approximately 20 mT without yoke 2020 consumes about 5 kW, while producing the same 20 mT $B_0$ magnetic field with yoke 2020 consumes about 750 W of power. Operating electromagnet 2010 with the yoke 2020, a $B_0$ magnetic field of approximately 40 mT may be produced using 2 kW of power and a $B_0$ magnetic field of approximately 50 mT may be produced using approximately 3 kW of power. Thus, the power requirements can be significantly reduced by use of yoke 220 allowing for operation of a $B_0$ magnet without a dedicated three-phase power connection. For example, mains electrical power in the United States and most of North America is provided at 120V and 60 Hz and rated at 15 or 20 amps, permitting utilization for devices operating below 1800 and 2400 W, respectively. Many facilities also have 220-240 VAC outlets with 30 amp ratings, permitting devices operating up to 7200 W to be powered from such outlets. According to some embodiments, a low-field MRI system utilizing a $B_0$ magnet comprising an electromagnet and a yoke (e.g., $B_0$ magnet 2000) is configured to be powered via a standard wall outlet, as discussed in further detail below. According to some embodiments, a low-field MRI system utilizing a $B_0$ magnet comprising an electromagnet and a yoke (e.g., $B_0$ magnet 2000) is configured to be powered via a 220-240 VAC outlet, as also discussed in further detail below.

Referring again to FIGS. 2C and 2D, exemplary $B_0$ magnet 2010 further comprises shim rings 2040a, 2040b and shim disks 2042a, 2042b configured to augment the generated $B_0$ magnetic field to improve homogeneity in the field of view (e.g., in the region between the upper and lower coils of the electromagnet where the $B_0$ field is suitable for sufficient MR signal production), as best seen in FIG. 2D in which the lower coils have been removed. In particular, shim rings 2040 and shim disk 2042 are dimensioned and arranged to increase the uniformity of the magnetic field generated by the electromagnet at least within the field of view of the $B_0$ magnet. In particular, the height, thickness and material of shim rings 2040a, 2040b and the diameter, thickness and material of shim disks 2042a, 2042b may be chosen so as to achieve a $B_0$ field of suitable homogeneity. For example, the shim disk may be provided with a diameter of approximately 5-6 inches and a width of approximately 0.3-0.4 inches. A shim ring may be formed from a plurality of circular arc segments (e.g., 8 circular arc segments) each having a height of approximately 20-22 inches, and a width of approximately 2 inches to form a ring having an inner diameter of approximately between 21-22 inches and approximately between 23-24 inches.

The weight of the $B_0$ magnet is a significant portion of the overall weight of the MRI system which, in turn, impacts the portability of the MRI system. In embodiments that primarily use low carbon and/or silicon steel for the yoke and shimming components, an exemplary $B_0$ magnet 2000 dimensioned similar to that described in the foregoing may weigh approximately 550 kilograms. According to some embodiments, cobalt steel (CoFe) may be used as the primary material for the yoke (and possibly the shim components), potentially reducing the weight of $B_0$ magnet 2000 to approximately 450 Kilograms. However, CoFe is generally more expensive than, for example, low carbon steel, driving up the cost of the system. Accordingly, in some embodiments, select components may be formed using CoFe to balance the tradeoff between cost and weight arising from its use. Using such exemplary $B_0$ magnets a portable, cartable or otherwise transportable MRI system may be constructed, for example, by integrating the $B_0$ magnet within a housing, frame or other body to which castors, wheels or other means of locomotion can be attached to allow the MRI system to be transported to desired locations (e.g., by manually pushing the MRI system and/or including motorized assistance). As a result, an MRI system can be brought to the location in which it is needed, increasing its availability and use as a clinical instrument and making available MRI applications that were previously not possible.

The primary contributor to the overall power consumption of a low-field MRI system employing a $B_0$ magnet such as $B_0$ magnet 2000 is the electromagnet (e.g., electromagnet 2010). For example, in some embodiments, the electromagnet may consume 80% or more of the power of the overall MRI system. To significantly reduce the power requirements of the MRI system, the inventors have developed $B_0$ magnets that utilize permanent magnets to produce and/or contribute to the $B_0$ electromagnetic field. According to some embodiments, $B_0$ electromagnets are replaced with permanent magnets as the main source of the $B_0$ electromagnetic field. A permanent magnet refers to any object or material that maintains its own persistent magnetic field once magnetized. Materials that can be magnetized to produce a permanent magnet are referred to herein as ferromagnetic and include, as non-limiting examples, iron, nickel, cobalt, neodymium (NdFeB) alloys, samarium cobalt (SmCo) alloys, alnico (AlNiCo) alloys, strontium ferrite, barium ferrite, etc. Permanent magnet material (e.g., magnetizable material that has been driven to saturation by a magnetizing field) retains its magnetic field when the driving field is removed. The amount of magnetization retained by a particular material is referred to as the material's remanence. Thus, once magnetized, a permanent magnet generates a magnetic field corresponding to its remanence, eliminating the need for a power source to produce the magnetic field.

Figure 2E:
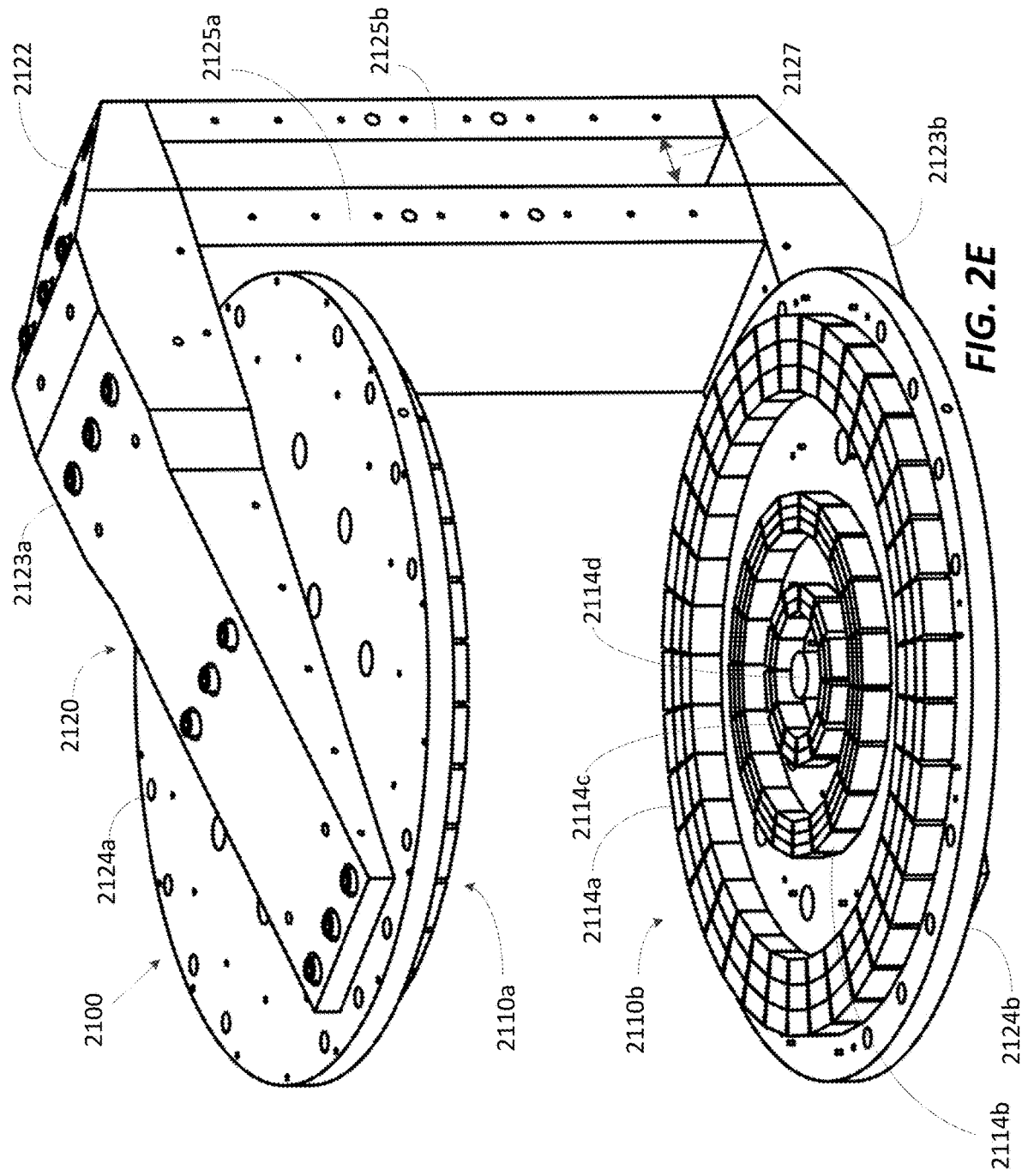
FIGS. 2E and 2F illustrate bi-planar permanent magnet configurations for a $B_0$ magnet, in accordance with some embodiments of the technology described herein.

FIG. 2E illustrates a permanent $B_0$ magnet, in accordance with some embodiments. In particular, $B_0$ magnet 2100 is formed by permanent magnets 2110a and 2110b arranged in a bi-planar geometry and a yoke 2120 that captures electromagnetic flux produced by the permanent magnets and transfers the flux to the opposing permanent magnet to increase the flux density between permanent magnets 2110a and 2110b. Each of permanent magnets 2110a and 2110b are formed from a plurality of concentric permanent magnets. In particular, as visible in FIG. 2E, permanent magnetic 2110b comprises an outer ring of permanent magnets 2114a, a middle ring of permanent magnets 2114b, an inner ring of permanent magnets 2114c, and a permanent magnet disk 2114d at the center. Permanent magnet 2110a may comprise the same set of permanent magnet elements as permanent magnet 2110b.

The permanent magnet material used may be selected depending on the design requirements of the system. For example, according to some embodiments, the permanent magnets (or some portion thereof) may be made of NdFeB, which produces a magnetic field with a relatively high magnetic field per unit volume of material once magnetized. According to some embodiments, SmCo material is used to form the permanent magnets, or some portion thereof. While NdFeB produces higher field strengths (and in general is less expensive than SmCo), SmCo exhibits less thermal drift and thus provides a more stable magnetic field in the face of temperature fluctuations. Other types of permanent magnet material(s) may be used as well, as the aspects are not limited in this respect. In general, the type or types of permanent magnet material utilized will depend, at least in part, on the field strength, temperature stability, weight, cost and/or ease of use requirements of a given $B_0$ magnet implementation.

The permanent magnet rings are sized and arranged to produce a homogenous field of a desired strength in the central region (field of view) between permanent magnets 2110a and 2110b. In the exemplary embodiment illustrated in FIG. 2E, each permanent magnet ring comprises a plurality segments, each segment formed using a plurality of blocks that are stacked in the radial direction and positioned adjacent to one another about the periphery to form the respective ring. The inventors have appreciated that by varying the width (in the direction tangent to the ring) of each permanent magnet, less waste of useful space may be achieved while using less material. For example, the space between stacks that does not produce useful magnetic fields can be reduced by varying the width of the blocks, for example, as function of the radial position of the block, allowing for a closer fit to reduce wasted space and maximize the amount of magnetic field that can be generated in a given space. The dimensions of the blocks may also be varied in any desired way to facilitate the production of a magnetic field of desired strength and homogeneity, as discussed in further detail below.

$B_0$ magnet 2100 further comprises yoke 2120 configured and arranged to capture magnetic flux generated by permanent magnets 2110a and 2110b and direct it to the opposing side of the $B_0$ magnet to increase the flux density in between permanent magnets 2110a and 2110b, increasing the field strength within the field of view of the $B_0$ magnet. By capturing magnetic flux and directing it to the region between permanent magnets 2110a and 2110b, less permanent magnet material can be used to achieve a desired field strength, thus reducing the size, weight and cost of the $B_0$ magnet. Alternatively, for given permanent magnets, the field strength can be increased, thus improving the SNR of the system without having to use increased amounts of permanent magnet material. For exemplary $B_0$ magnet 2100, yoke 2120 comprises a frame 2122 and plates 2124a and 2124b. In a manner similar to that described above in connection with yoke 2020, plates 2124a and 2124b capture magnetic flux generated by permanent magnets 2110a and 2110b and direct it to frame 2122 to be circulated via the magnetic return path of the yoke to increase the flux density in the field of view of the $B_0$ magnet. Yoke 2120 may be constructed of any desired ferromagnetic material, for example, low carbon steel, CoFe and/or silicon steel, etc. to provide the desired magnetic properties for the yoke. According to some embodiments, plates 2124a and 2124b (and/or frame 2122 or portions thereof) may be constructed of silicon steel or the like in areas where the gradient coils could most prevalently induce eddy currents.

Exemplary frame 2122 comprises arms 2123a and 2123b that attach to plates 2124a and 2124b, respectively, and supports 2125a and 2125b providing the magnetic return path for the flux generated by the permanent magnets. The arms are generally designed to reduce the amount of material needed to support the permanent magnets while providing sufficient cross-section for the return path for the magnetic flux generated by the permanent magnets. Arms 2123a has two supports within a magnetic return path for the $B_0$ field produced by the $B_0$ magnet. Supports 2125a and 2125b are produced with a gap 2127 formed between, providing a measure of stability to the frame and/or lightness to the structure while providing sufficient cross-section for the magnetic flux generated by the permanent magnets. For example, the cross-section needed for the return path of the magnetic flux can be divided between the two support structures, thus providing a sufficient return path while increasing the structural integrity of the frame. It should be appreciated that additional supports may be added to the structure, as the technique is not limited for use with only two supports and any particular number of multiple support structures.

As discussed above, exemplary permanent magnets 2110a and 2110b comprise a plurality of rings of permanent magnetic material concentrically arranged with a permanent magnet disk at the center. Each ring may comprise a plurality of stacks of ferromagnetic material to form the respective ring, and each stack may include one or more blocks, which may have any number (including a single block in some embodiments and/or in some of the rings). The blocks forming each ring may be dimensioned and arranged to produce a desired magnetic field. The inventors have recognized that the blocks may be dimensioned in a number of ways to decrease cost, reduce weight and/or improve the homogeneity of the magnetic field produced, as discussed in further detail in connection with the exemplary rings that together form permanent magnets of a $B_0$ magnet, in accordance with some embodiments.

Figure 2F:
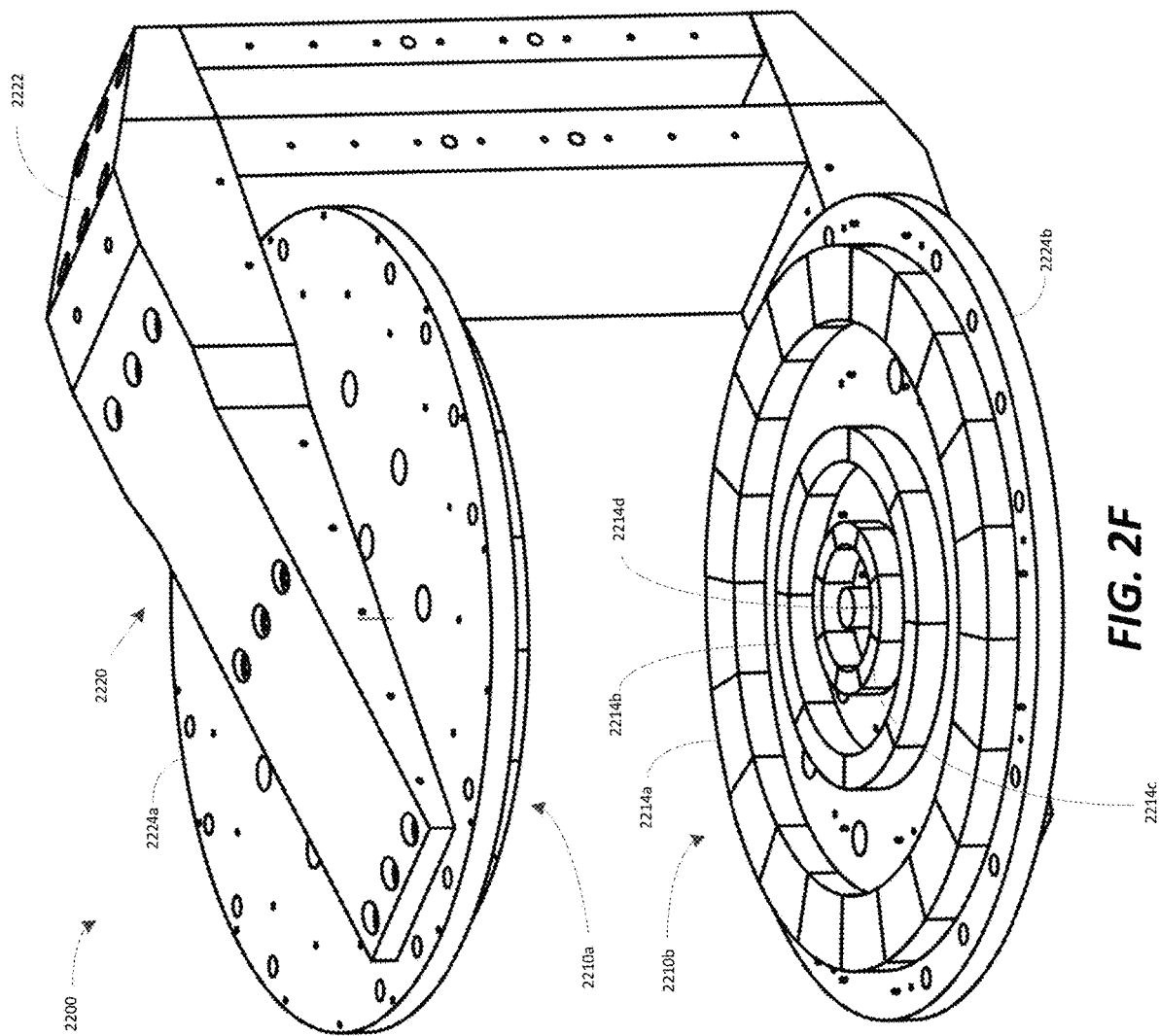

FIG. 2F illustrates a $B_0$ magnet 2200, in accordance with some embodiments. $B_0$ magnet 2200 may share design components with $B_0$ magnet 2100 illustrated in FIG. 2E. In particular, $B_0$ magnet 2200 is formed by permanent magnets 2210a and 2210b arranged in a bi-planar geometry with a yoke 2220 coupled thereto to capture electromagnetic flux produced by the permanent magnets and transfer the flux to the opposing permanent magnet to increase the flux density between permanent magnets 2210a and 2210b. Each of permanent magnets 2210a and 2210b are formed from a plurality of concentric permanent magnets, as shown by permanent magnet 2210b comprising an outer ring of permanent magnets 2214a, a middle ring of permanent magnets 2214b, an inner ring of permanent magnets 2214c, and a permanent magnet disk 2214d at the center. Permanent magnet 2210a may comprise the same set of permanent magnet elements as permanent magnet 2210b. The permanent magnet material used may be selected depending on the design requirements of the system (e.g., NdFeB, SmCo, etc. depending on the properties desired).

The permanent magnet rings are sized and arranged to produce a homogenous field of a desired strength in the central region (field of view) between permanent magnets 2210a and 2210b. In particular, in the exemplary embodiment illustrated in FIG. 2F, each permanent magnet ring comprises a plurality of circular arc segments sized and positioned to produce a desired $B_0$ magnetic field, as discussed in further detail below. In a similar manner to yoke 2120 illustrated in FIG. 2E, yoke 2220 is configured and arranged to capture magnetic flux generated by permanent magnets 2210a and 2210b and direct it to the opposing side of the $B_0$ magnet to increase the flux density in between permanent magnets 2210a and 2210b. Yoke 2220 thereby increases the field strength within the field of view of the $B_0$ magnet with less permanent magnet material, reducing the size, weight and cost of the $B_0$ magnet. Yoke 2220 also comprises a frame 2222 and plates 2224a and 2224b that, in a manner similar to that described above in connection with yoke 2220, captures and circulates magnetic flux generated by the permanent magnets 2210a and via the magnetic return path of the yoke to increase the flux density in the field of view of the $B_0$ magnet. The structure of yoke 2220 may be similar to that described above to provide sufficient material to accommodate the magnetic flux generated by the permanent magnets and providing sufficient stability, while minimizing the amount of material used to, for example, reduce the cost and weight of the $B_0$ magnet.

Because a permanent $B_0$ magnet, once magnetized, will produce its own persistent magnetic field, power is not required to operate the permanent $B_0$ magnet to generate its magnetic field. As a result, a significant (often dominant) contributor to the overall power consumption of an MRI system can be eliminated, facilitating the development of an MRI system that can be powered using mains electricity (e.g., via a standard wall outlet or common large household appliance outlets). As discussed above, the inventors have developed low power, portable low-field MRI systems that can be deployed in virtually any environment and that can be brought to the patient who will undergo an imaging procedure. In this way, patients in emergency rooms, intensive care units, operating rooms and a host of other locations can benefit from MRI in circumstances where MRI is conventionally unavailable.

Figure 3A:
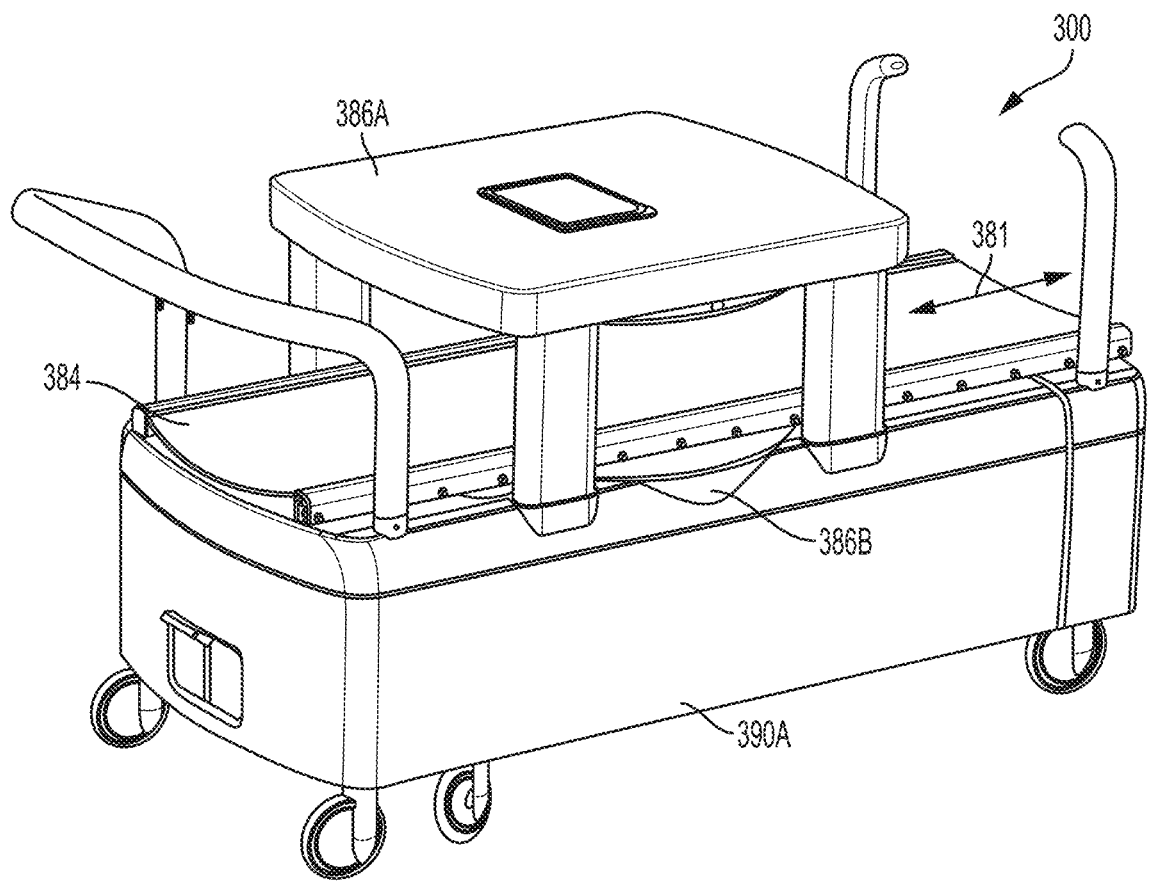
FIGS. 3A and 3B illustrate a transportable low-field MRI system suitable for use with change detection techniques described herein, in accordance with some embodiments of the technology described herein.
Figure 3B:
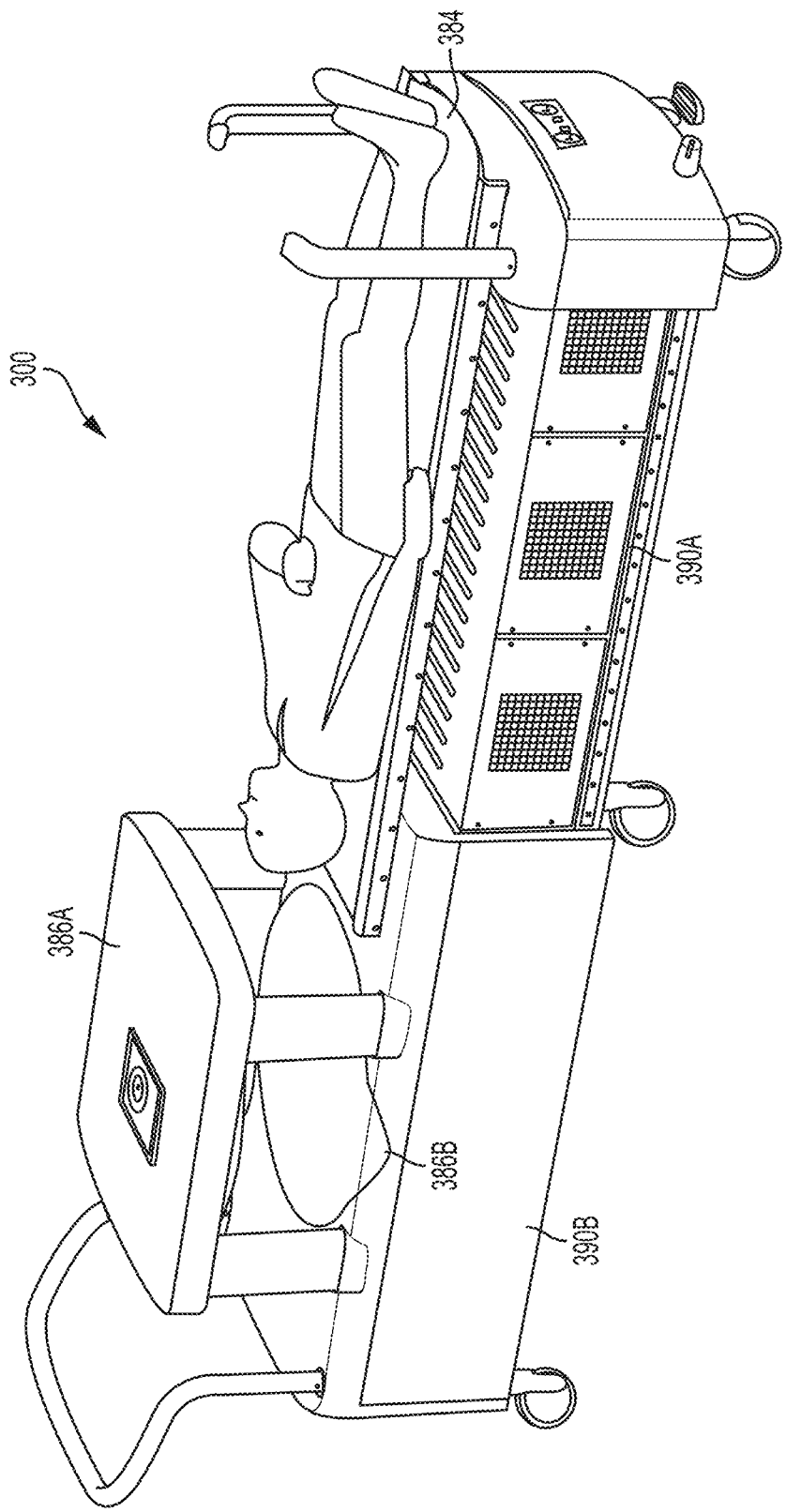

FIGS. 3A-3B illustrate a portable or cartable low-field MRI system 300 suitable for use in performing change detection techniques described herein, in accordance with some embodiments. System 300 may include magnetic and power components, and potentially other components (e.g., thermal management, console, etc.), arranged together on a single generally transportable and transformable structure. System 300 may be designed to have at least two configurations; a configuration adapted for transport and storage, and a configuration adapted for operation. FIG. 3A shows system 300 when secured for transport and/or storage and FIG. 3B shows system 300 when transformed for operation. System 300 comprises a portion 390A that can be slid into and retracted from a portion 390B when transforming the system from its transport configuration to its operation configuration, as indicated by the arrows shown in FIG. 3B. Portion 390A may house power electronics, console (which may comprise an interface device such as a touch panel display) and thermal management. Portion 390A may also include other components used to operate system 300 as needed.

Portion 390B comprises magnetic components of low-field MRI system 300, including laminate panels on which magnetic components are integrated in any of the combinations discussed herein. When transformed to the configuration adapted for operating the system to perform MRI (as shown in FIG. 3B), supporting surfaces of portions 390A and 390B provide a surface on which the patient can lie. A slide-able bed or surface 384 may be provided to facilitate sliding the patient into position so that a portion of the patient to be imaged is within the field of view of the low-field MRI magnetic components. System 300 provides for a portable compact configuration of a low-field MRI system that facilitates access to MRI imaging in circumstances where it conventionally is not available (e.g., in the NICU).

FIGS. 3A-3B illustrate an example of a convertible low-field MRI system that utilizes a bi-planar magnet forming and imaging region between housings 386A and 386B. Housings 386A and 386B house magnetic components for the convertible system 300. According to some embodiments, the magnetic components may be produced, manufactured and arranged using exclusively laminate techniques, exclusively traditional techniques, or using a combination of both (e.g., using hybrid techniques). The convertible low-field MRI system 300 allows the system to be brought to the patient to facilitate monitoring of target anatomy of the patient. For example, convertible low-field MRI system 300 may be brought to a patient in the NICU and the unconscious patient may be placed on the slide-able bed and positioned within the field of view of the system. The patient may then be monitored by obtaining continuous, periodic and/or regular MRI images over an extended period of time (e.g., over the course of one or multiple hours) to evaluate changes taking places using any of the various change detection techniques described herein.

Figure 3D:
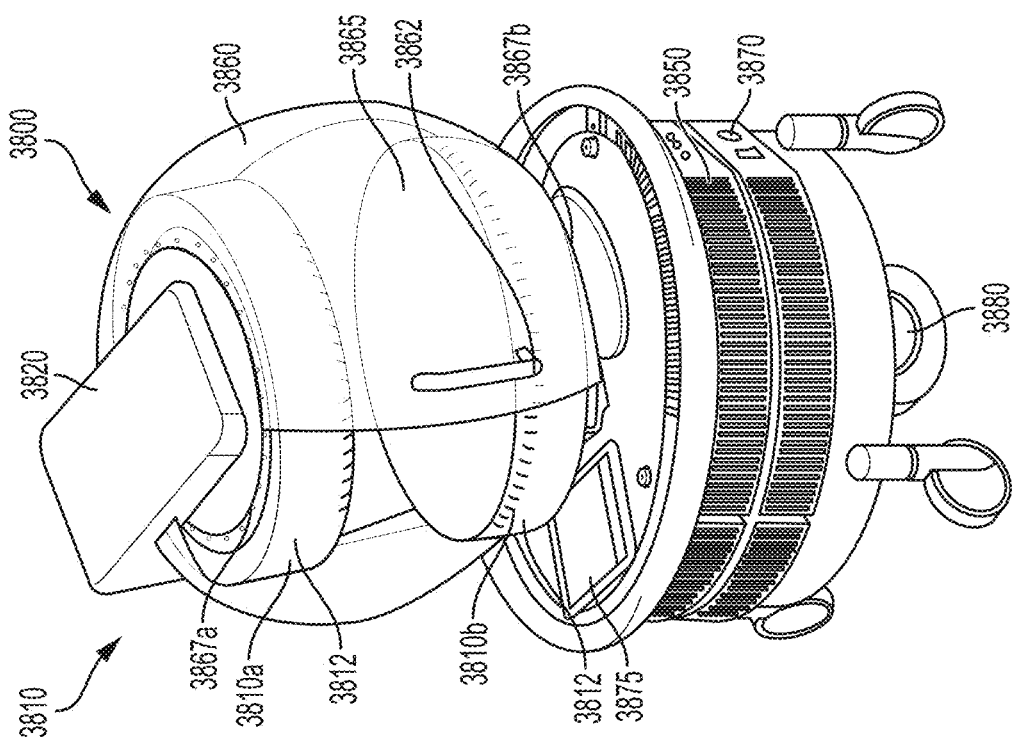
FIGS. 3C and 3D illustrate views of a portable MRI system, in accordance with some embodiments of the technology described herein.
Figure 3C:
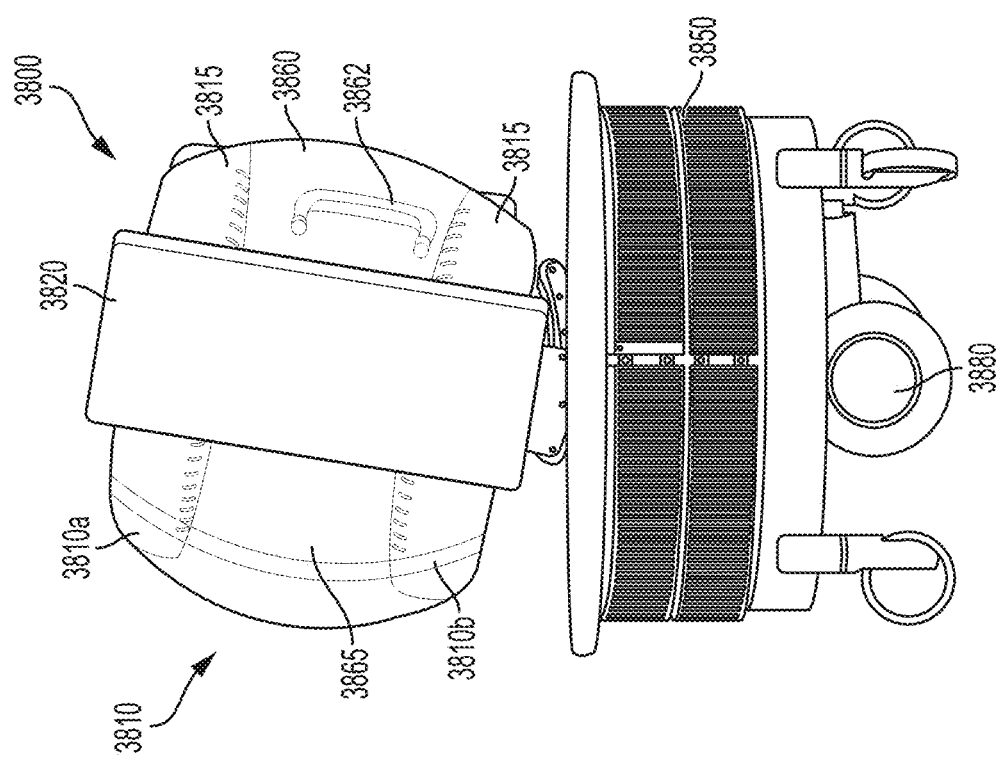

FIGS. 3C and 3D illustrate views of another portable MRI system 3800, which may be used to implement various change detection techniques, in accordance with some embodiments of the technology described herein. Portable MRI system 3800 comprises a $B_0$ magnet 3810 formed in part by an upper magnet 3810a and a lower magnet 3810b having a yoke 3820 coupled thereto to increase the flux density within the imaging region. The $B_0$ magnet 3810 may be housed in magnet housing 3812 along with gradient coils 3815 (e.g., any of the gradient coils described in U.S. application Ser. No. 14/845,652, titled "Low Field Magnetic Resonance Imaging Methods and Apparatus" and filed on Sep. 4, 2015, which is herein incorporated by reference in its entirety). According to some embodiments, $B_0$ magnet 3810 comprises an electromagnet. According to some embodiments, $B_0$ magnet 3810 comprises a permanent magnet (e.g., any permanent magnet described in U.S. application Ser. No. 15/640,369, titled "LOW-FIELD MAGNETIC RESONANCE IMAGING METHODS AND APPARATUS," filed on Jun. 30, 2017, which is incorporated by reference herein in its entirety).

Portable MRI system 3800 further comprises a base 3850 housing the electronics needed to operate the MRI system. For example, base 3850 may house electronics including, but not limited to, one or more gradient power amplifiers, an on-system computer, a power distribution unit (PDU), one or more power supplies, and/or any other power components configured to operate the MRI system using mains electricity (e.g., via a connection to a standard wall outlet and/or a large appliance outlet). For example, base 3870 may house low power components, such as those described herein, enabling at least in part the portable MRI system to be powered from readily available wall outlets. Accordingly, portable MRI system 3800 can be brought to the patient and plugged into a wall outlet in the vicinity.

Portable MRI system 3800 further comprises moveable slides 3860 that can be opened and closed and positioned in a variety of configurations. Slides 3860 include electromagnetic shielding 3865, which can be made from any suitable conductive or magnetic material, to form a moveable shield to attenuate electromagnetic noise in the operating environment of the portable MRI system to shield the imaging region from at least some electromagnetic noise. As used herein, the term electromagnetic shielding refers to conductive or magnetic material configured to attenuate the electromagnetic field in a spectrum of interest and positioned or arranged to shield a space, object and/or component of interest. In the context of an MRI system, electromagnetic shielding may be used to shield electronic components (e.g., power components, cables, etc.) of the MRI system, to shield the imaging region (e.g., the field of view) of the MRI system, or both.

The degree of attenuation achieved from electromagnetic shielding depends on a number of factors including the type material used, the material thickness, the frequency spectrum for which electromagnetic shielding is desired or required, the size and shape of apertures in the electromagnetic shielding (e.g., the size of the spaces in a conductive mesh, the size of unshielded portions or gaps in the shielding, etc.) and/or the orientation of apertures relative to an incident electromagnetic field. Thus, electromagnetic shielding refers generally to any conductive or magnetic barrier that acts to attenuate at least some electromagnetic radiation and that is positioned to at least partially shield a given space, object or component by attenuating the at least some electromagnetic radiation.

It should be appreciated that the frequency spectrum for which shielding (attenuation of an electromagnetic field) is desired may differ depending on what is being shielded. For example, electromagnetic shielding for certain electronic components may be configured to attenuate different frequencies than electromagnetic shielding for the imaging region of the MRI system. Regarding the imaging region, the spectrum of interest includes frequencies which influence, impact and/or degrade the ability of the MRI system to excite and detect an MR response. In general, the spectrum of interest for the imaging region of an MRI system correspond to the frequencies about the nominal operating frequency (i.e., the Larmor frequency) at a given $B_0$ magnetic field strength for which the receive system is configured to or capable of detecting. This spectrum is referred to herein as the operating spectrum for the MRI system. Thus, electromagnetic shielding that provides shielding for the operating spectrum refers to conductive or magnetic material arranged or positioned to attenuate frequencies at least within the operating spectrum for at least a portion of an imaging region of the MRI system.

In portable MRI system 3800 illustrated in FIGS. 3C and 3D, the moveable shields are thus configurable to provide shielding in different arrangements, which can be adjusted as needed to accommodate a patient, provide access to a patient, and/or in accordance with a given imaging protocol. For example, for the imaging procedure illustrated in FIG. 3E (e.g., a brain scan), once the patient has been positioned, slides 3960 can be closed, for example, using handle 3862 to provide electromagnetic shielding 3965 around the imaging region except for the opening that accommodates the patient's upper torso. In the imaging procedure illustrated in FIG. 3F (e.g., a scan of the knee), slides 3960 may be arranged to have openings on both sides to accommodate the patient's legs. Accordingly, moveable shields allow the shielding to be configured in arrangements suitable for the imaging procedure and to facilitate positioning the patient appropriately within the imaging region.

Figure 3E:
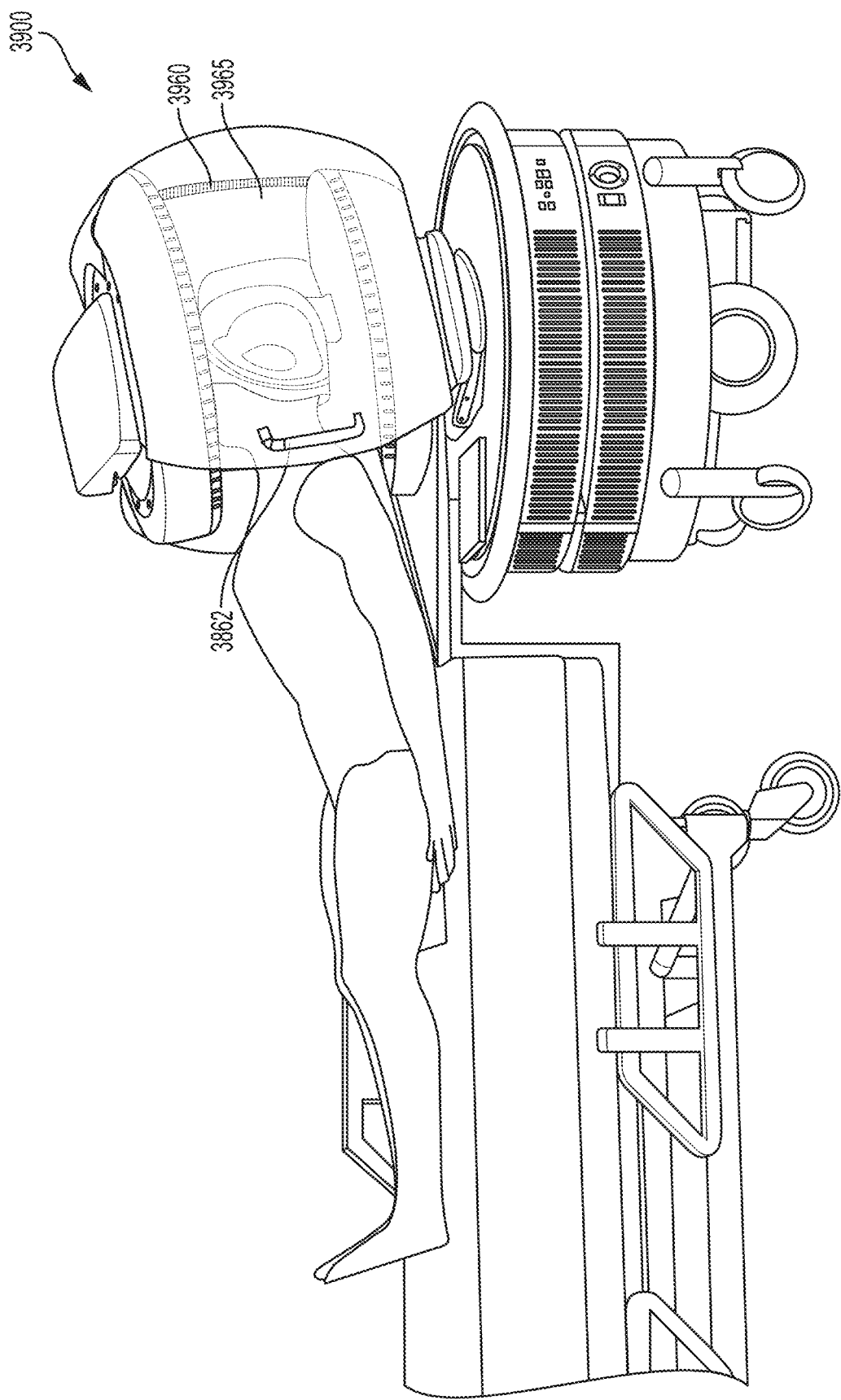
FIG. 3E illustrates a portable MRI system performing a scan of the head, in accordance with some embodiments of the technology described herein.
Figure 3F:
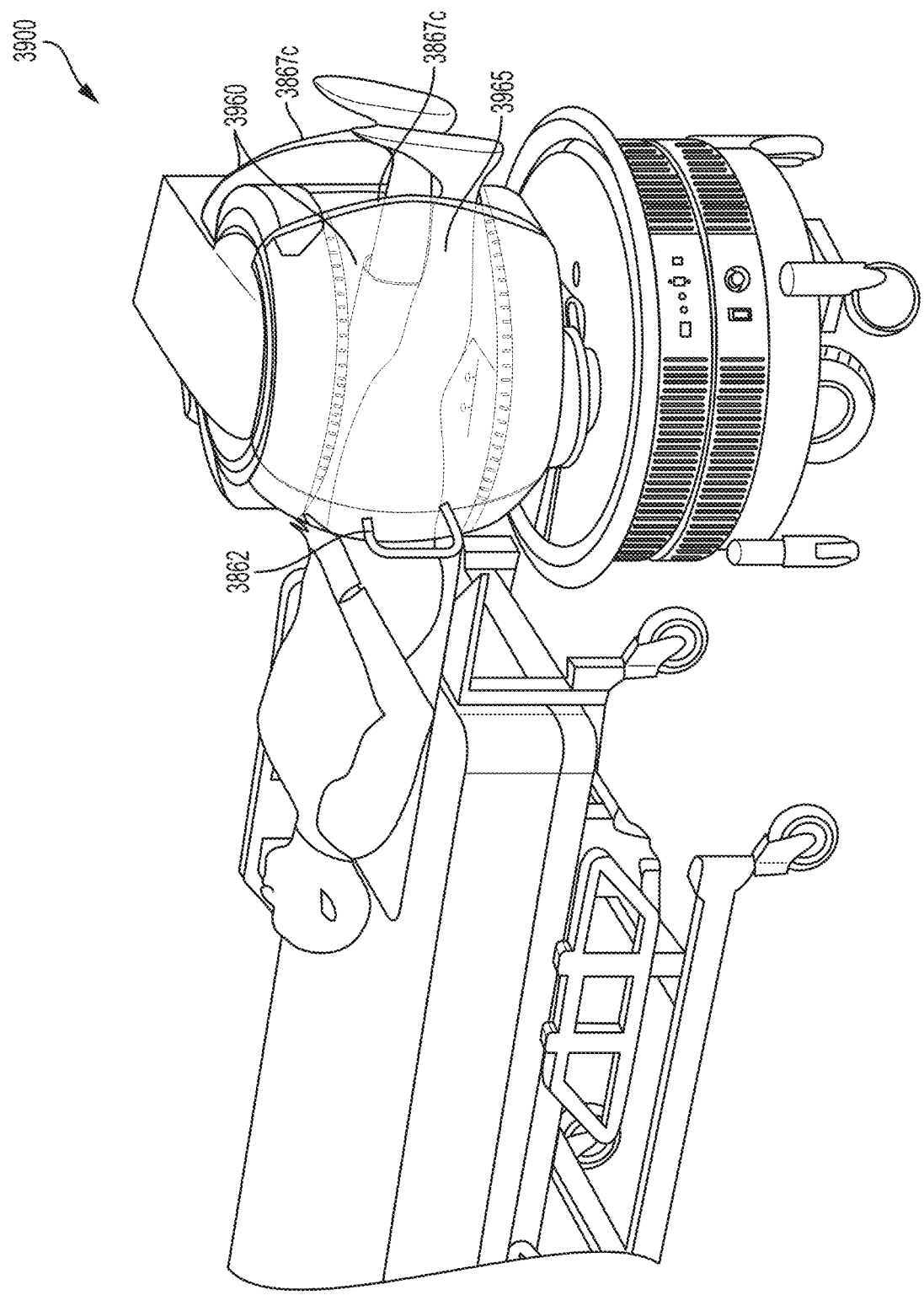
FIG. 3F illustrates a portable MRI system performing a scan of the knee, in accordance with some embodiments of the technology described herein.

In some embodiments, a noise reduction system comprising one or more noise reduction and/or compensation techniques may be performed to suppress at least some of the electromagnetic noise that is not blocked or sufficiently attenuated by shielding 3865. In particular, the inventors have developed noise reduction systems configured to suppress, avoid and/or reject electromagnetic noise in the operating environment in which the MRI system is located. According to some embodiments, these noise suppression techniques work in conjunction with the moveable shields to facilitate operation in the various shielding configurations in which the slides may be arranged. For example, when slides 3960 are arranged as illustrated in FIG. 3F, increased levels of electromagnetic noise will likely enter the imaging region via the openings. As a result, the noise suppression component will detect increased electromagnetic noise levels and adapt the noise suppression and/or avoidance response accordingly. Due to the dynamic nature of the noise suppression and/or avoidance techniques described herein, the noise reduction system is configured to be responsive to changing noise conditions, including those resulting from different arrangements of the moveable shields. Thus, a noise reduction system in accordance with some embodiments may be configured to operate in concert with the moveable shields to suppress electromagnetic noise in the operating environment of the MRI system in any of the shielding configurations that may be utilized, including configurations that are substantially without shielding (e.g., configurations without moveable shields).

To ensure that the moveable shields provide shielding regardless of the arrangements in which the slides are placed, electrical gaskets may be arranged to provide continuous shielding along the periphery of the moveable shield. For example, as shown in FIG. 3D, electrical gaskets 3867a and 3867b may be provided at the interface between slides 3860 and magnet housing to maintain to provide continuous shielding along this interface. According to some embodiments, the electrical gaskets are beryllium fingers or beryllium-copper fingers, or the like (e.g., aluminum gaskets), that maintain electrical connection between shields 3865 and ground during and after slides 3860 are moved to desired positions about the imaging region. According to some embodiments, electrical gaskets 3867c are provided at the interface between slides 3860, as illustrated in FIG. 3F so that continuous shielding is provided between slides in arrangements in which the slides are brought together. Accordingly, moveable slides 3860 can provide configurable shielding for the portable MRI system.

To facilitate transportation, a motorized component 3880 is provide to allow portable MRI system to be driven from location to location, for example, using a control such as a joystick or other control mechanism provided on or remote from the MRI system. In this manner, portable MRI system 3800 can be transported to the patient and maneuvered to the bedside to perform imaging, as illustrated in FIGS. 3E and 3F. As discussed above, FIG. 3E illustrates a portable MRI system 3900 that has been transported to a patient's bedside to perform a brain scan. FIG. 3F illustrates portable MRI system 3900 that has been transported to a patient's bedside to perform a scan of the patient's knee.

The portable MRI systems described herein may be operated from a portable electronic device, such as a notepad, tablet, smartphone, etc. For example, tablet computer 3875 may be used to operate portable MRI system to run desired imaging protocols and to view the resulting images. Tablet computer 3875 may be connected to a secure cloud to transfer images for data sharing, telemedicine, and/or deep learning on the data sets. Any of the techniques of utilizing network connectivity described in U.S. application Ser. No. 14/846,158, titled "Automatic Configuration of a Low Field Magnetic Resonance Imaging System," filed Sep. 4, 2015, which is herein incorporated by reference in its entirety, may be utilized in connection with the portable MRI systems described herein.

Figure 3G:
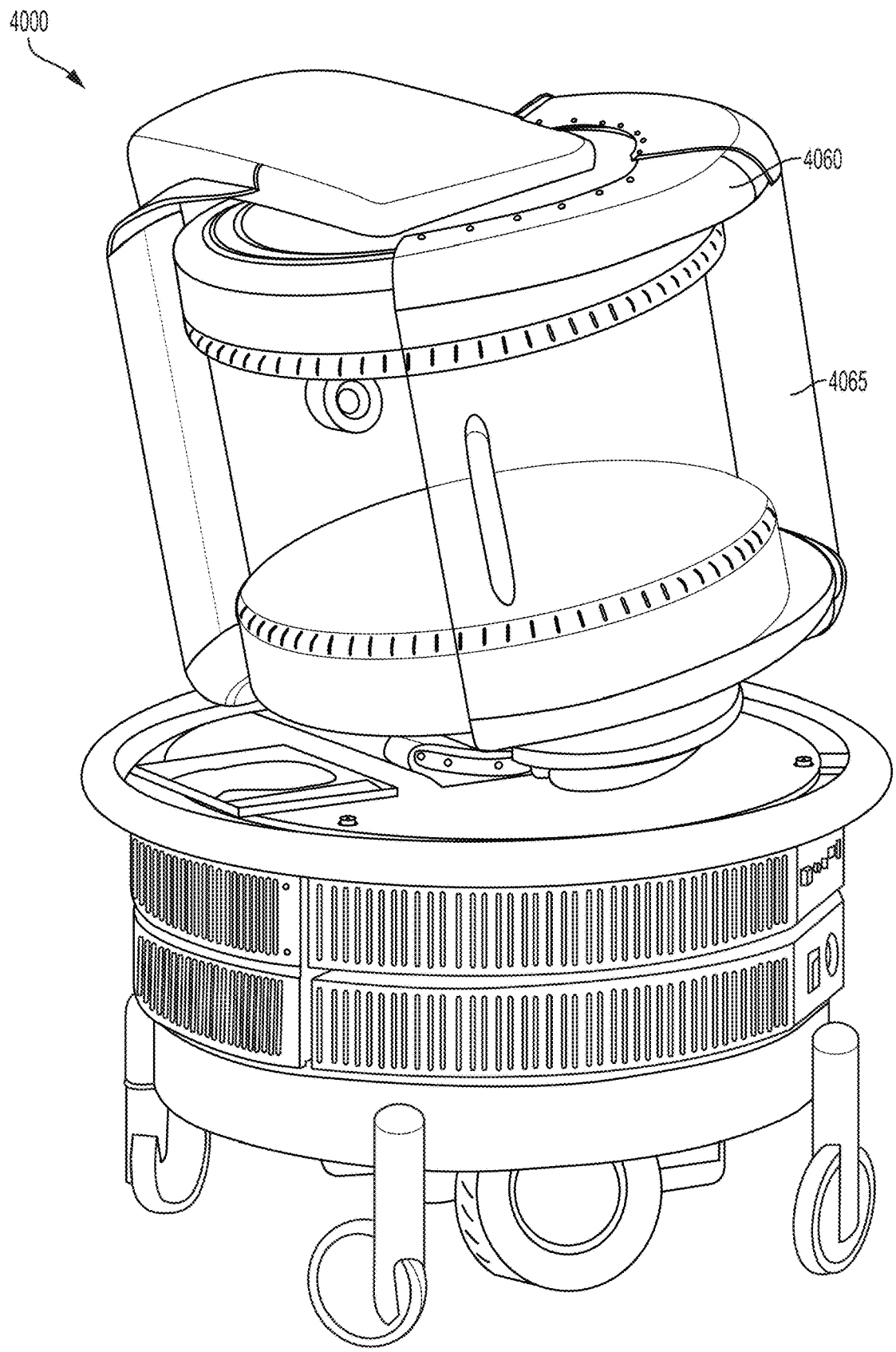
FIG. 3G illustrates another example of a portable MRI system, in accordance with some embodiments of the technology described herein.

FIG. 3G illustrates another example of a portable MRI system, in accordance with some embodiments of the technology described herein. Portable MRI system 4000 may be similar in many respects to portable MRI systems illustrated in FIGS. 3C-3F. However, slides 4060 are constructed differently, as is shielding 4065, resulting in electromagnetic shields that are easier and less expensive to manufacture. As discussed above, a noise reduction system may be used to allow operation of a portable MRI system in unshielded rooms and with varying degrees of shielding about the imaging region on the system itself, including no, or substantially no, device-level electromagnetic shields for the imaging region.

It should be appreciated that the electromagnetic shields illustrated in FIGS. 3C-3G are exemplary and providing shielding for an MRI system is not limited to the example electromagnetic shielding described herein. Electromagnetic shielding can be implemented in any suitable way using any suitable materials. For example, electromagnetic shielding may be formed using conductive meshes, fabrics, etc. that can provide a moveable "curtain" to shield the imaging region. Electromagnetic shielding may be formed using one or more conductive straps (e.g., one or more strips of conducting material) coupled to the MRI system as either a fixed, moveable or configurable component to shield the imaging region from electromagnetic interference, some examples of which are described in further detail below. Electromagnetic shielding may be provided by embedding materials in doors, slides, or any moveable or fixed portion of the housing. Electromagnetic shields may be deployed as fixed or moveable components, as the aspects are not limited in this respect.

Figure 4:
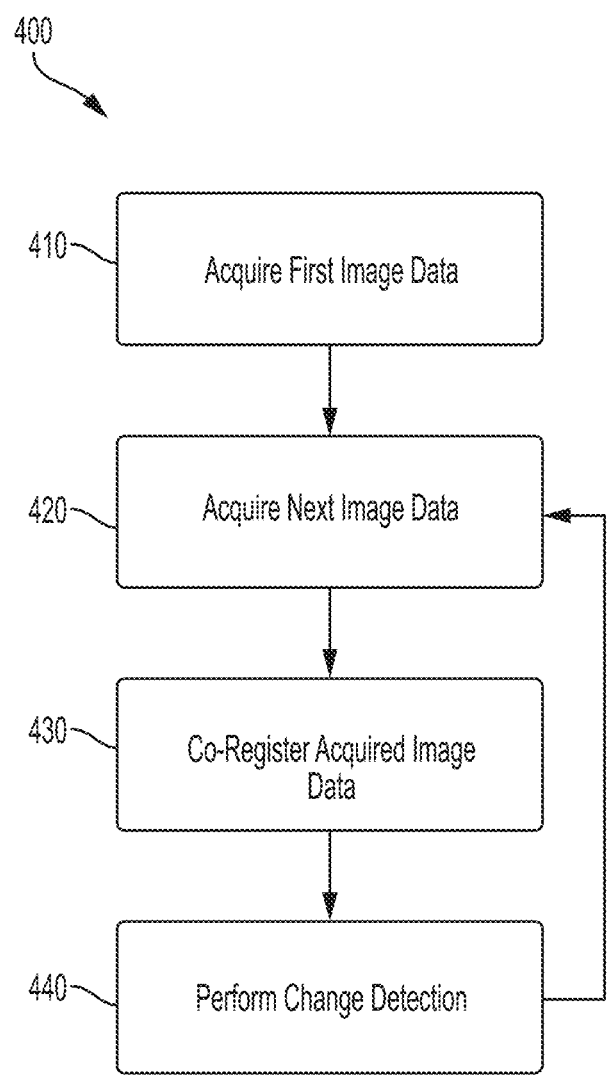
FIG. 4 illustrates a method of performing change detection, in accordance with some embodiments of the technology described herein.

FIG. 4 illustrates a method of monitoring a patient using low-field MRI to detect changes therein, in accordance with some embodiments. In act 410, first MR image data is acquired by a low-field MRI device of a target portion of anatomy (e.g., a portion of the brain, a portion of a knee, etc.) of a patient positioned within the low-field MRI device. Positioning a patient within the low-field device refers to placing the patient relative to the magnetic components of the low-field MRI device such that a portion of the patient's anatomy is located within the field of view of the low-field MRI device so that MR image data can be acquired. The term MR image data is used herein to refer to MR data generically including, but not limited to, MR data prior to image reconstruction (e.g., k-space MR data) and MR data that has been processed in some way (e.g., post-image reconstruction MR data such as a three dimensional (3D) volumetric image). Because both registration and change detection techniques described herein can be performed in any domain (or a combination of domains), the term MR image data is used to refer to acquired MR data agnostic to domain and/or whether image reconstruction (or any other processing) has been performed. As an example application, MR image data of a patient's brain may be acquired to monitor temporal changes within the brain (e.g., changes regarding an aneurysm or bleeding within the brain, changes in a tumor or other tissue anomaly, changes in chemical composition, etc.).

In act 420, subsequent (next) MR image data is acquired of the same or substantially the same portion of the anatomy included in the first MR image data. The next MR image data may be acquired immediately following acquisition of the first MR image data, or may be obtained after a desired period of delay (e.g., after 1, 2, 3, 4, 5, 10, 15, 20 minutes, etc.). As a result, the next MR image data captures the portion of the anatomy after some finite amount of time has elapsed. The inventors have appreciated that low-field MRI facilitates relatively fast image acquisition, allowing a temporal sequence of MR image data to be acquired in relatively quick succession, thus capturing changes that may be of interest to the physician. The accessibility, availability and/or relative low cost of the low-field MRI system enables MR data to be acquired over extended periods of time at any time interval needed to monitor and/or otherwise observe and evaluate the patient.

As with the first MR image data, the next MR image data may be of any form (e.g., a 3D volumetric image, a 2D image, k-space MR data, etc.). According to some embodiments, the next MR image data (or any subsequent next MR image data acquired) is obtained using the same acquisition parameters used to acquire the first MR image data. For example, the same pulse sequence, field of view, SNR, and resolution may be used to acquire MR signals from the same portion of the patient. In this manner, the MR image data may be compared to evaluate changes that have occurred within the anatomy being imaged. For example, as described below, MR image data may be used to determine whether there is a change in the degree of midline shift in a patient. As another example, as described below, MR image data may be used to determine whether there is a change in a size of an abnormality (e.g., a hemorrhage, a lesion, an edema, a stroke core, a stroke penumbra, and/or swelling) in a patient. In other embodiments, one or more acquisition parameters may be altered to change the acquisition strategy for acquiring next MR image data, as discussed in further detail below in connection with FIG. 5.

The first, next and any subsequent MR image data acquired are referred to as respective "frames" of MR image data. A sequence of frames may be acquired and the individual frames may be registered in a sequence of frames acquired over time. Thus, a frame corresponds to acquired MR image data representative of the particular time at which the MR image data was acquired. Frames need not include the same amount of MR image data or correspond to the same field of view, but frames generally need sufficient overlap so that adequate feature descriptors can be detected (e.g., sufficient subject matter in common between frames).

In act 430, the first and next MR image data are co-registered or aligned with one another. Any suitable technique may be used to co-register the first and next MR image data, or any pair of acquired MR image data for which change detection processing is desired. In the simplest case, registration may be performed by assuming that the patient is still so that the MR image data is aligned without transforming or deforming the MR image data. However, such a simplified technique does not account for movement of the patient, changes resulting from breathing, etc., which may need to be compensated for in other ways to avoid attributing observed differences between images resulting from these factors to biological processes. More sophisticated registration techniques used to align the MR image data to account for movement of the patient, breathing, etc., include, but are not limited to, the use of deformation models and/or correlation techniques adapted to MR image data acquired at different points in time.

According to some embodiments, co-registering acquired MR image data involves determining a transformation that best aligns the MR image data (e.g., in a least squares sense). The transformation between MR image data acquired at different points in time may include translation, rotation, scale or any suitable linear or non-linear deformation, as the aspects are not limited in this respect. The transformation may be determined at any desired scale. For example, a transformation may be determined for a number of identified sub-regions (e.g., volumes including a number of voxels) of the MR image data, or may be determined for each voxel in the MR image data. The transformation may be determined in any manner, for example, using a deformation model that deforms a mesh or coordinate frame of first MR image data to the coordinate frame of next MR image data and vice versa. Any suitable registration technique may be used, as the aspects are not limited in this respect. An illustrative process for co-registering MR image data acquired at different points in time in accordance with some embodiment, is discussed in further detail below in connection with FIG. 6.

In act 440, one or more changes are detected in the co-registered MR image data. For example, once the MR image data has been co-registered, differences between the MR image data can be attributed to changes in the patient's anatomy being imaged (e.g., morphological changes to the anatomy or other changes to the biology or physiology of the imaged anatomy), such as a change in the size of an aneurysm, increased or decreased bleeding, progression or regression of a tumor or other tissue anomaly, changes in chemical composition, or other biological or physiological changes of interest. Change detection can be performed in any suitable way. For example, once the MR image data has been co-registered, change detection may be performed in k-space using amplitude and phase information (coherent change detection), or change detection can be performed in the image domain using intensity information (non-coherent change detection). Generally speaking, coherent change detection may be more sensitive, revealing changes on the sub-voxel level. However, even though non-coherent change detection may be generally less sensitive, change detection in the image domain may be more robust to co-registration errors.

In some embodiments, change detection may be performed by deriving features from each MR frame in a sequence of MR frames and comparing the features to one another. For example, in some embodiments, image processing techniques (e.g., including the deep learning techniques described herein) may be applied to each MR frame in a sequence of two or more MR frames, obtained by imaging a patient's brain, to identify a respective sequence of two or more midline shift measurements. In turn, the sequence of midline shift measurements may be used to determine whether there is a change in the degree of midline shift for the patient being monitored. As another example, in some embodiments, image processing techniques (e.g., the deep learning techniques described herein), may be applied to each MR frame in a sequence of two or more MR frames, obtained by imaging a patient's brain, to identify a respective sequence of two or more measurements of a size of an abnormality in the patient's brain (e.g., a hemorrhage, a lesion, an edema, a stroke core, a stroke penumbra, and/or swelling). In turn, the sequence of size measurements may be used to determine whether there is a change in the size of the abnormality in the brain of a patient being monitored.

In some embodiments, multi-resolution techniques may be used to perform change detection. For example, the first MR image data may correspond to a baseline high-resolution image, and subsequently-acquired MR image data may correspond to low-resolution images that may be correlated with the high-resolution baseline image. Acquiring low-resolution images may speed up the frame rate of the change detection process enabling the acquisition of more data in a shorter period of time. Any suitable techniques or criteria may be used to determine which data to acquire for a low-resolution image. The particular data to acquire for a low-resolution image may be determined using, for example, wavelets, selective k-space sampling, polyphase filtering, key-frame based techniques, etc. Sparse sampling of k-space over short time intervals (e.g., time-varying selective sampling of k-space), as an example, results in better time resolution.

The selection of particular data to acquire may also be determined by detecting changes between MR image data frames. For example, when a change is detected, a 1D or 2D volume selection having a field of view that includes the location of the detected change may be selected for acquisition to interrogate a particular part of the anatomy demonstrating change over time.

Using coherent change detection, differences in phase and amplitude in each "frame" of acquired MR data are evaluated. For example, co-registered frames of MR image data may be subtracted to obtain difference information indicative of changes occurring in the MR data. According to some embodiments, a finite impulse response (FIR) filter is applied to each "voxel" in the frame, which can be used as a reference. Filtering can also be used to provide a "look-ahead filter" that considers a number of frames over which to perform change detection. For example, a current, previous and next frame may be evaluated using a sliding window to analyze changes over a desired number of frames.

The inventors have recognized that acquiring a full 3D volume of MR data may take a substantial amount of time. In some embodiments, change detection is used to selectively determine particular data (e.g., particular lines in k-space) to acquire, such that MR data used for image reconstruction may be acquired in a shorter timeframe than would be required to acquire a full 3D volume. For example, using the sliding window approach described above, an initial 3D volume may first be acquired. Then, at subsequent points in time, rather than reacquiring the full 3D volume, a subset of the lines in k-space selected based on parts of the image that are changing may be acquired and the previous 3D volume may be updated with the newly acquired data.

In some embodiments, a particular feature or area of interest may be identified a priori, and the acquisition sequence may be tailored to acquire lines of k-space that will emphasize the identified feature or area of interest. For example, the acquisition sequence may focus on acquiring just the edges of k-space or any other suitable part of k-space. In some embodiments, the identified area of interest may be a portion of the anatomy. For example, to analyze a post-surgical bleed, it may not be necessary to acquire data on the entire anatomy. Rather, select portions of k-space that correspond to the anatomy of interest for monitoring may be sampled multiple times in a relatively brief period of time to enable a physician to closely monitor changes in the anatomy of interest over the shorter timescale providing for a high temporal correlation between the acquisitions.

Using non-coherent change detection, the intensity of voxels in 3D images reconstructed from acquired MR data may be compared to evaluate changes as they occur over time. Detected changes, either evaluated coherently (e.g., in k-space) or non-coherently (e.g., in 3D images) may be conveyed in any number of ways. For example, changes in the MR image data may be emphasized on displayed images to provide a visual indication to a physician of changes occurring over time. For example, voxels undergoing change can be rendered in color that in turn may be coded according to the extent of the change that occurred. In this manner, a physician can quickly see the "hot spots" that are undergoing significant change. Alternatively, or in addition to, change detection can be performed by analyzing regions over which changes are occurring. For example, connected component analysis may be used to locate contiguous regions where voxel changes have occurred. That is, regions of connected voxels that have undergone change may be emphasized or displayed differently (e.g., using color, shading, etc.) to indicate that changes are occurring in the corresponding regions. Changes detected in acquired MR image data may be conveyed in other ways, as the aspects are not limited in this respect.

Shape and volume analysis may also be performed to assess whether a given feature of the anatomy of interest is changing (e.g., growing or shrinking, progressing or regressing, or to otherwise characterize change in the features). For example, image processing techniques can be used to segment MR image data into regions and to assess one or more properties of the segment such as shape, volume, etc. Changes to the one or more segments properties may be conveyed to a physician via a display or otherwise. For example, the size of a tumor may be monitored across a sequence of images to evaluate whether the tumor is increasing or decreasing in size. As another example, a brain bleed may be monitored over time wherein the important change to evaluate is the volume of the bleed. Thus, acquired MR image data may be processed to segment features of interest (e.g., tumor, bleed, hemorrhage, etc.) and compute the volume of the corresponding feature.

It should be appreciated that segmented volumes can be analyzed in other ways to characterize metrics of interest for the segmented volume. For example, 2D and/or 3D shape descriptors may be applied to the segmented features to characterize any number of aspects or properties of the segmented feature including, but not limited to, volume, surface area, symmetry, "texture," etc. In this way, change detection may be performed on features of interest captured in the acquired MR data to evaluate how the features are changing over time. Changes detected in segmented features can be utilized not only to understand how the feature is evolving in time, but characteristics of the particular features can be compared to stored information to assist in differentiating healthy from unhealthy, normal from anomalous and/or to assess the danger of a particular condition. The information obtained from the MR data may also be stored along with existing information to grow the repository of information that can be used for subsequent data analysis.

According to some embodiments, techniques may be used to remove changes in the data caused by regular or periodic movement, such as breathing or heart beat etc. By determining which parts of the image are changing and which are not, it is possible to focus acquisition on only the parts of the image that are changing and not acquire data for the parts of the image that are not changing. By acquiring a smaller set of data only related to the parts of the image that are changing, the acquisition time is compressed. Additionally, some changes in the image are caused by periodic events such as breathing and heartbeats. In some embodiments, periodic events are modeled based on their periodicity to enable a change detection process to ignore the periodic movements caused by the period events when determining which parts of the image are changing and should be the focus of acquisition.

According to some embodiments, change detection may be performed by detecting the rate of change of MR image data over a sequence of acquired MR image data. As used herein, a rate of change refers to any functional form of time. Detecting the rate of change may provide richer data regarding the subject matter being imaged, such as indicating the severity of a bleed, size of a hemorrhage, increase in midline shift, the aggressiveness of a lesion, etc. As one example, when a contrast agent is administered, there is a natural and expected way in which the contrast agent is taken up by the body. The uptake of contrast agent is detected as a signal increase that will register as a change having a particular functional form. The manner in which the signal changes as the contrast agent washes out and/or is metabolized will also give rise to a detectable change in signal that will have a functional form over time. The functional form of changes over time can provide information about the type, aggressiveness or other characteristics of a lesion or other abnormality that can provide clinically useful and/or critical data. As another example, a stroke victim may be monitored after a stroke has occurred, changes in the time course of the stroke lesion that differs from expected might be used to alert personnel to unusual changes, provide a measure of drug efficacy, or provide other information relevant to the condition of the patient. In general, detecting rate of change can facilitate higher order analysis of the subject matter being imaged.

Techniques are available that facilitate faster acquisition of MR data, enabling quicker image acquisition for low-field MRI. For example, compressed sensing techniques, sparse imaging array techniques and MR fingerprinting are some examples of techniques that can expedite MR image acquisition. Additionally, in some embodiments, Doppler techniques may be used to analyze multiple frames of images over a short period of time to estimate velocities that may be used to filter out parts of the image that are not changing.

Upon completion of detecting changes in acquired MR image data, act 420 may be repeated to obtain further MR image data, either immediately or after waiting for a predetermined amount of time before acquiring subsequent MR image data. Subsequently acquired MR image data may be compared with any MR image data previously acquired to detect changes that have occurred over any desired interval of time (e.g., by repeating act 430 and 440). In this manner, sequences of MR image data can be obtained and changes detected and conveyed to facilitate understanding of the temporal changes taking place in the portion of the anatomy of the patient being monitored, observed and/or evaluated. It should be appreciated that any acquired MR image data can be registered and analyzed for change. For example, successive MR image data may be compared so that, for example, changes on a relatively small time scale can be detected. The detected change may be conveyed to a physician so that the anatomy of interest can be continuously, regularly and/or periodically monitored.

In addition, acquired MR image data may be stored so that a physician can request change detection be performed at desired points of interest. For example, a physician may be interested to see changes that have taken place within the last hour and may specify that change detection be performed between MR image data acquired an hour ago and present time MR image data. The physician may specify an interval of time, may specify multiple times of interest, or may select thumbnails of timestamped images to indicate which MR image data the physician would like change detection performed. Thus, the techniques described herein may be used to monitor ongoing changes and/or to evaluate changes that have occurred over any interval of time during which MR image data has been acquired. The above described change detection techniques may be used to enable monitoring, evaluation and observation of a patient over a period of time, thus enabling MRI to be utilized as a monitoring tool in ways that conventional MRI and other modalities cannot be used.

In some embodiments, acquired MR image data may be used to evaluate change with respect to a stored high-field MRI scan. In this way, a patient may be imaged using a high-field MRI scan initially, but subsequent monitoring (which would not be feasible using high-field MRI) would be performed using a low-field MRI system, examples of which are provided herein. The change detection techniques described herein can be applied not only to detecting changes between sets MR image data acquired by a low-field MRI system, but also to detecting changes between MR image data acquired by a high-field MRI system (e.g., initially) and MR image data acquired by a low-field MRI system (e.g., subsequently), regardless of the order in which the high-field MR image data and the low-field MR image data was obtained.

Figure 5:
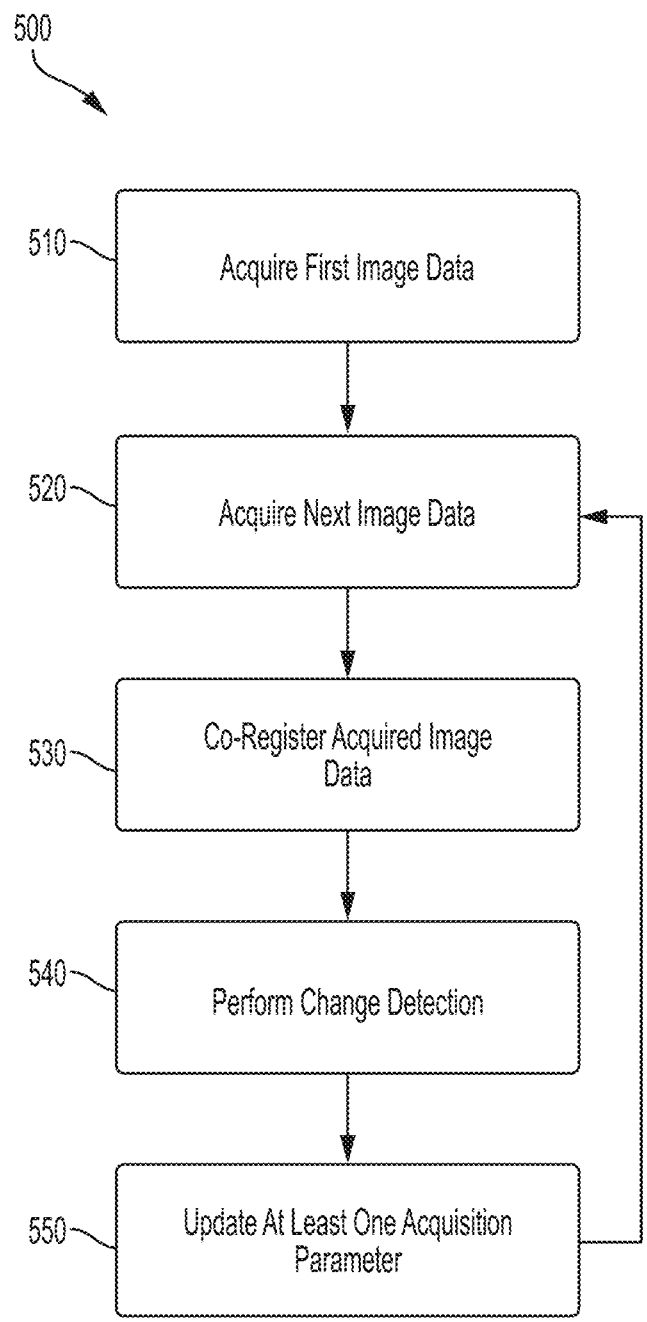
FIG. 5 illustrates a method of modifying acquisition parameters based on change detection information, in accordance with some embodiments of the technology described herein.

FIG. 5 illustrates a method of changing an acquisition strategy based, at least in part, on observations made regarding change detection. The inventors have developed a multi-acquisition console that allows acquisition parameters to be modified on the fly to dynamically update an acquisition strategy implemented by the low-field MRI system. For example, commands to the low-field MRI system can be streamed from the console to achieve dynamic updates to the acquisition process. The inventors have appreciated that the ability to dynamically update acquisition parameters and/or change the acquisition strategy can be exploited to achieve a new paradigm for MRI, enabling the MRI system to be used for monitoring a patient and adapting the acquisition strategy based on observations of the acquired MR image data (e.g., based on change detection information).

In method 500 illustrated in FIG. 5, acts 510-540 may be similar to acts 410-440 of method 400 illustrated in FIG. 4 to obtain change detection information in regard to MR image data obtained by a low-field MRI system. In act 550, at least one acquisition parameter may be updated, changed or other modified based on the results of change detection. Acquisition parameters that may be varied are not limited in any respect, and may include any one or combination of field of view, signal-to-noise ratio (SNR), resolution, pulse sequence type, etc. Some examples of acquisition parameters that may be changed are described in further detail below.

According to some embodiments, change detection information may be used to update the acquisition parameters to, for example, increase SNR of MR data obtained from a particular region. For example, based on characteristics of co-registration (e.g., properties of the transformation, deformation models, etc.) and/or changes observed in particular regions, it may be desirable to increase the SNR in those regions to, for example, better evaluate the subject matter present, to improve further change detection, or otherwise obtaining more information regarding the portion of the anatomy being monitored and/or observed. Similarly, acquisition parameters may be altered to obtain higher resolution MR data for particular regions of the portion of anatomy being monitored/observed. Change detection may reveal that a patient has moved or subject matter of interest is no longer optimally in the field of view. This information may be utilized to dynamically change the field of view of subsequent image acquisition.

According to some embodiments, the type of pulse sequence that is applied may be changed based on what is observed in change detection data obtained from acquired MR image data. Different pulse sequences may be better at capturing particular types of information and these differences can be exploited to allow for appropriate exploration based on observed change detection data. Due, at least in part, to the dynamic capability of the system developed by the inventors, different pulse sequences can be interleaved, alternated or otherwise utilized to acquire MR data that captures information of interest. For example, a fast spin echo sequence may have been used to acquire a number of frames of MR image data and the results of change detection may suggest the benefit of changing to a different pulse sequence, for example, a bSSFP sequence to observe a particular change (e.g., to obtain different MR data, to allow for higher SNR or resolution in a particular region, etc.). In this manner, changes that may not be observable using one type of sequence may be seen by changing the type of pulse sequence being used.

As another example, pulse sequences may be chosen for the type of contrast provided (e.g., T1, T2, etc.) or the type of information that is captured, and the appropriate pulse sequence can be utilized to obtain MR data, which can be changed dynamically during the monitoring process. The choice of pulse sequence or combination of pulse sequences used can be guided by the change detection information that is obtained. For example, MR data may be captured using a given pulse sequence and, based on obtained change detection information (e.g., based on information obtained by performing act 540), the pulse sequence may be changed to explore a region using magnetic resonance spectroscopy (MRS). In this manner, exploration of the chemical composition of a portion of anatomy being monitored may be initiated as a result of changes observed in the MR data.

It should be appreciated that the acquisition parameters may be varied dynamically at any time during acquisition. That is, a full acquisition need not complete before altering the acquisition strategy. As a result, updating acquisition parameter(s) may be performed based on partial acquisition and/or partial image reconstruction to facilitate an acquisition strategy that is fully dynamic. The ability to dynamically update any one or combination of acquisition parameters allows MRI to be utilized as a monitoring and exploration tool, whereas conventional MRI systems cannot be used in this way.

Some applications, such as diffusion weighted imaging (DWI), require substantial amounts of power due to the higher gradient fields needed for such applications. In some embodiments, power savings may be achieved by interleaving acquisitions for a DWI (or other) sequence with acquisitions that require less power. By allowing for the dynamic update of acquisition parameters during an acquisition, any combination and interleaving of acquisition sequences to achieve a desired goal (e.g., low power consumption, reduced heating, reducing stress on the gradient coils, etc.) may be realized.

In some embodiments, biological or physiological events that unfold over a relatively short timeframe may be studied using the change detection techniques described herein. For example, for arterial spin labeling, a full data set may be initially obtained, and subsequent acquisitions may sparsely sample the data. Perfusion of the blood over time may be monitored change detection, where the changes in the image correspond to the inflowing blood to a particular region of the imaged anatomy.

As discussed, above, co-registration of MR image data acquired at different points in time enables the identification of changes in MR data by reducing the effect of patient movement on the change detection process. The co-registration may be accomplished with a model for the effects of deformation. The deformation mesh captures changes in shape and distribution over time, which may occur from subtle movements of the patient or from biological morphology. To maintain registration across frames as the imaged volume moves or deforms, the k-space acquisition strategy may be updated based on new constraints of the deformed volume. For example, acquisition parameters affecting field of view, SNR, resolution, etc., may be updated based on new constraints of the deformed volume.

Figure 6:
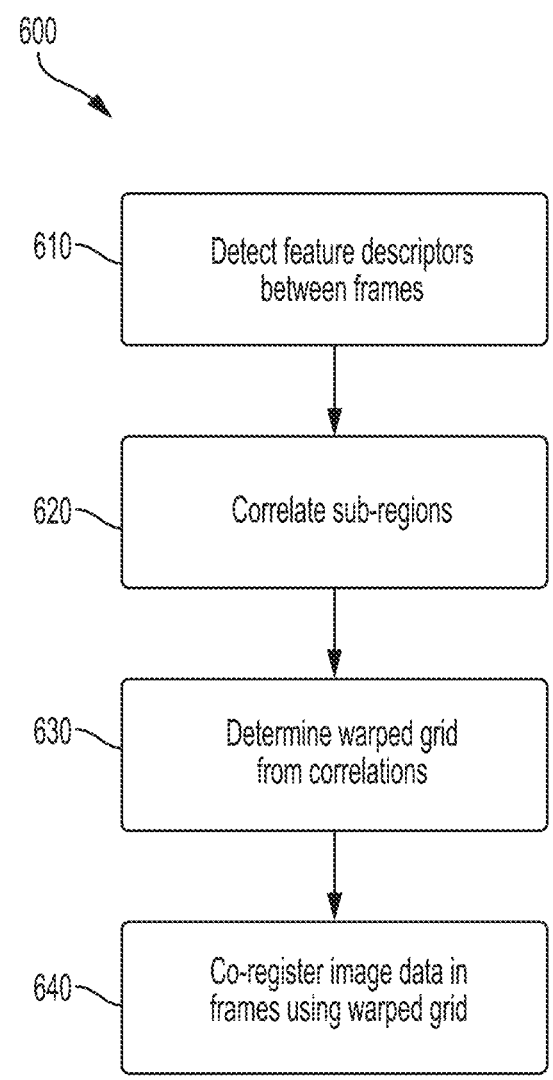
FIG. 6 illustrates a method of co-registering MR image data, in accordance with some embodiments of the technology described herein.

FIG. 6 illustrates a technique 600 for co-registering frames of MR image data, in accordance with some embodiments. For example, registration technique 600 may be used to align a pair of frames acquired at two separate times. In act 610, one or more feature descriptors appearing or common to the frames being co-registered are detected. Feature descriptors may be any feature present in the MR image between frames that can be reliably detected. Features may include local characteristics such as edges, corners, ridges, etc. and/or may include region characteristics such as curves, contours, shape, intensity distributions and/or patterns, etc. Any feature or characteristic that can be reliably detected between frames may be used as a feature descriptor, as the aspects are not limited in this respect. Any suitable technique may be used to determine the feature descriptors including, but not limited to, SIFT, SURF, U-SURF, CenSurE, BRIEF, ORB, and corner detector techniques such as FAST, Harris, Hessian, and Shi-Tomasi.

After the feature descriptors between frames have been determined, the process proceeds to act 620, where associated sub-regions across the frames are correlated. The correlation calculations between sub-regions may be performed in any number of dimensions (e.g., 1D, 2D, 3D), as aspects are not limited in this respect. After the correlations between sub-regions are determined, the process proceeds to act 630, where the warped or deformed model from frame to frame is determined based on the correlations between the sub-regions in the different frames. Once the deformation of the model is determined between frames, the process proceeds to act 640, wherein the model deformation is used to co-register the data across the multiple frames.

Once the data is co-registered, change detection metrics including, but not limited to those discussed above, such as coherent changes, non-coherent changes, and others including position changes, velocity, acceleration or time derivative vectors may be determined using the co-registered data. Other metrics including segmentation and geometric shape descriptors such as surface area, volume, crinkliness, spherical harmonic basis coefficients, etc. may also be determined based on the co-registered data and optionally the metrics may be used to update acquisition parameters for future acquisitions on the fly as discussed above.

As described above, the inventors have developed techniques for using low-field MRI for monitoring a patient to determine whether there is a change in a degree of midline shift in the patient's brain. Midline shift refers to an amount of displacement of the brain's midline from its normal symmetric position due to trauma (e.g., stroke, hemorrhage, or other injury) and is an important indicator for clinicians of the severity of the brain trauma. The midline shift may be characterized as a shift of the brain past its midline, usually in the direction away from the affected side (e.g., a side with an injury).

In some embodiments, the midline shift may be measured as the distance between a midline structure of the brain (e.g., a point on the septum pellucidum) and a line designated as the midline. The midline may be coplanar with the falx cerebri (also known as the cerebral falx), which a crescent-shaped fold of the meningeal layer of dura mater that descends vertically in the longitudinal fissure between the cerebral hemispheres of the human brain. The midline may be represented as a line connecting the anterior and posterior attachments of the falx cerebri to the inner table of the skull.

Figure 7A:
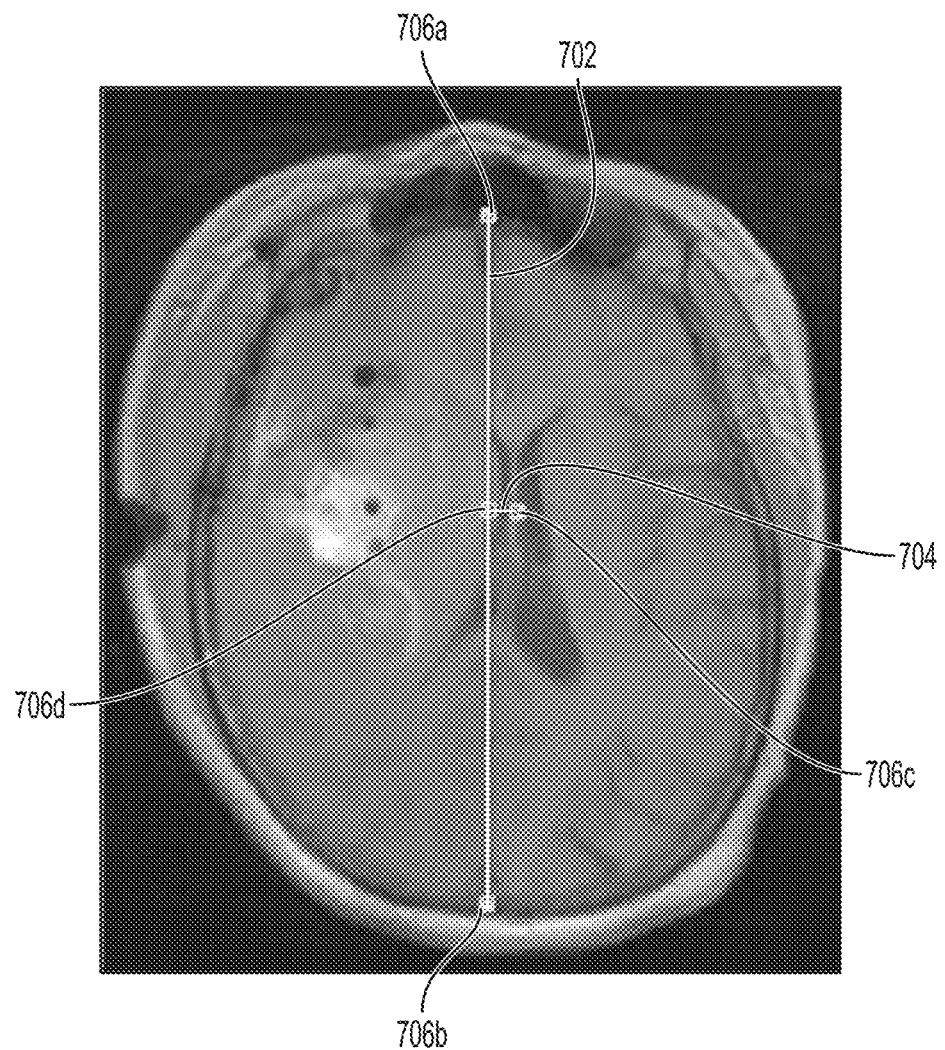
FIG. 7A illustrates a midline shift measurement, in accordance with some embodiments of the technology described herein.

As one example, illustrated in FIG. 7A, the midline 702 is a line connecting the anterior and posterior attachment points 706a and 706b of the falx cerebri. In this example, the midline shift may be measured as the distance between the measurement point 706c in the septum pellucidum and the midline 702. That distance is the length of the line 704 defined by endpoints 706c and 706d, and which is orthogonal to midline 702.

Figure 7B:
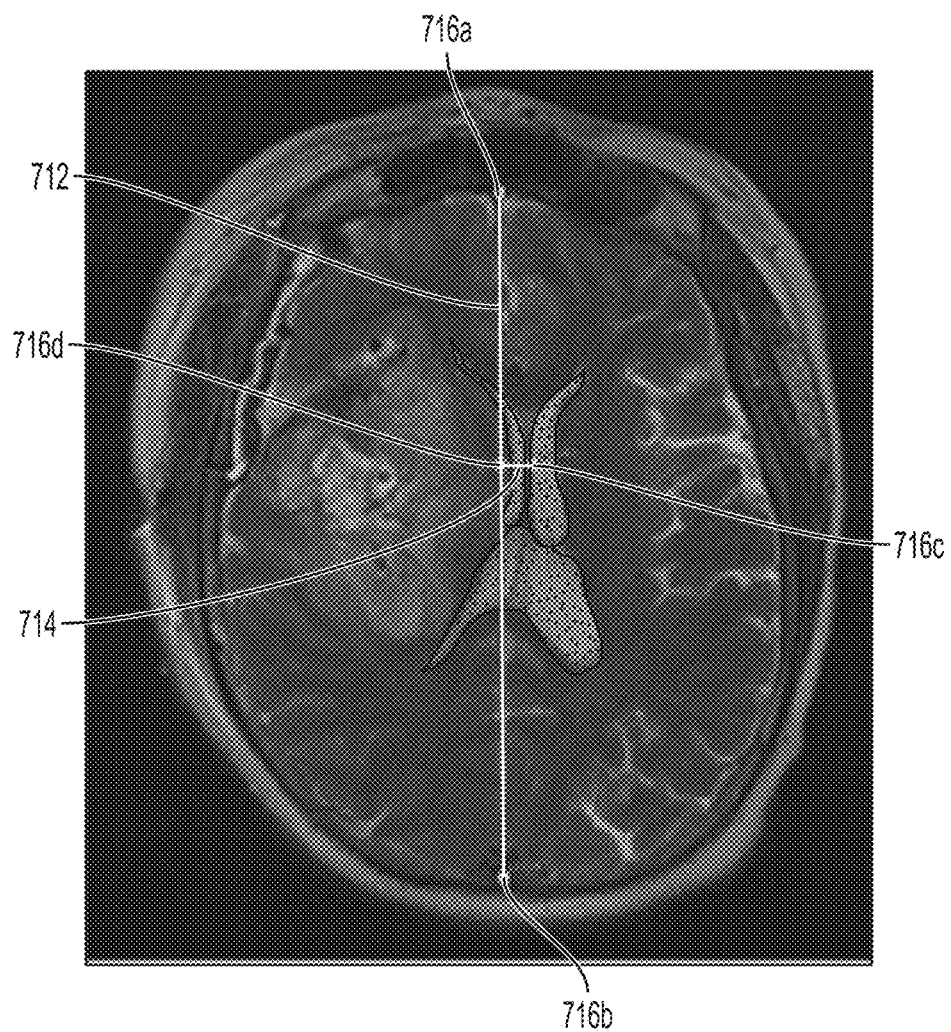
FIG. 7B illustrates another midline shift measurement, in accordance with some embodiments of the technology described herein.

As another example, illustrated in FIG. 7B, the midline 712 is a line connecting the anterior and posterior attachment points 716a and 716b of the falx cerebri. In this example, the midline shift may be measured as the distance between the measurement point 716c in the septum pellucidum and the midline 712. That distance is the length of the line 714 defined by endpoints 716c and 716d, and which is orthogonal to midline 712.

Figure 8:
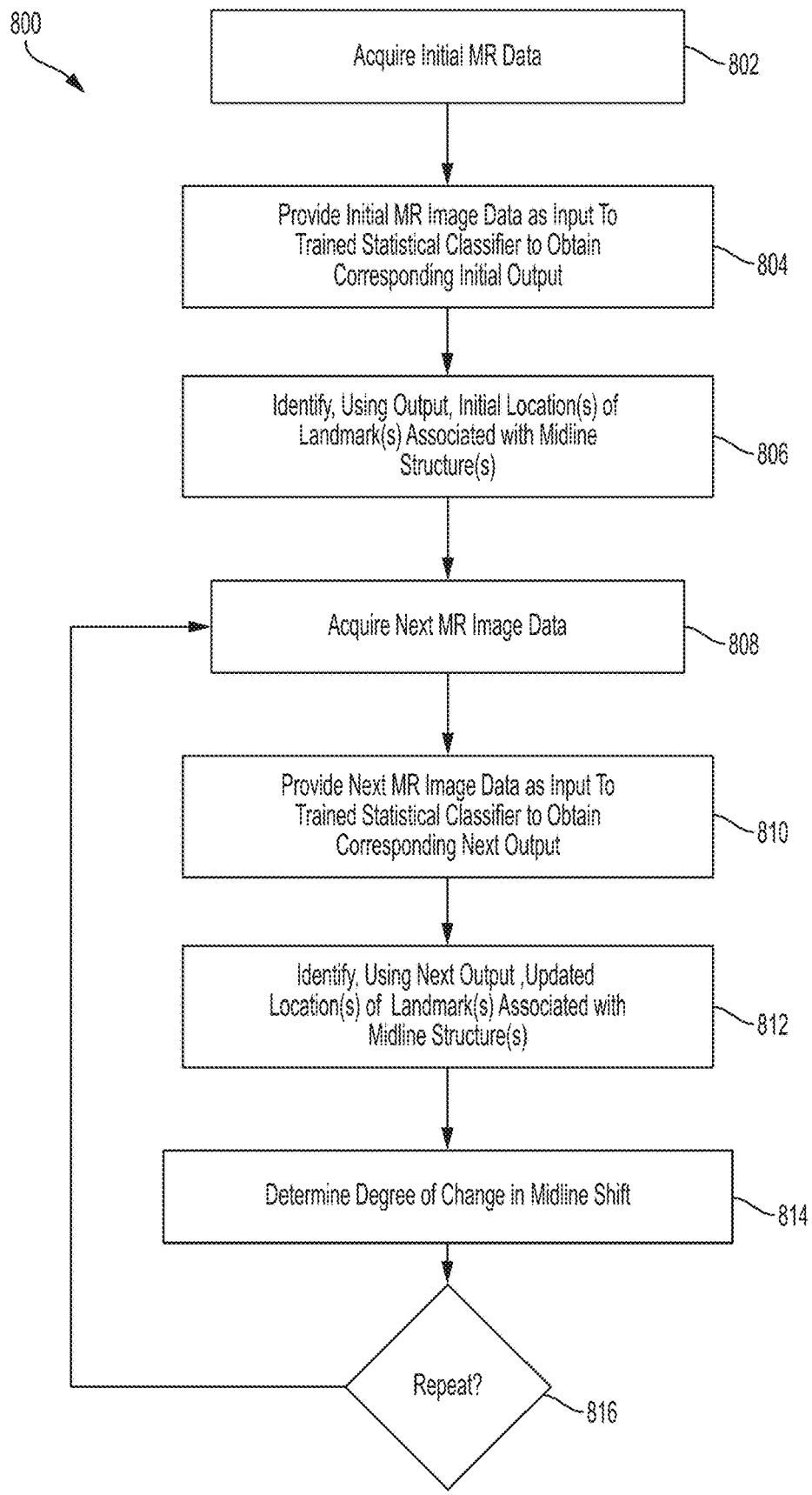
FIG. 8 illustrates a method for determining a degree of change in the midline shift of a patient, in accordance with some embodiments of the technology described herein.

FIG. 8 is a flowchart of an illustrative process 800 for determining a degree of change in the midline shift of a patient, in accordance with some embodiments of the technology described herein. In some embodiments, the entirety of process 800 may be performed while the patient is within a low-field MRI device, which may be of any suitable type described herein including, for example, any of the low-field MRI devices illustrated in FIGS. 3A-3G).

Process 800 begins at act 802, where the low-field MRI device acquires initial magnetic resonance data of a target portion of the patient's brain. As described herein, the term MR image data is used herein to refer to MR data generically including, but not limited to, MR data prior to image reconstruction (e.g., k-space MR data) and MR data that has been processed in some way (e.g., post-image reconstruction MR data such as a three dimensional (3D) volumetric image). In some embodiments, the initial MR data may include one or more two-dimensional images of respective brain slices (e.g., two, three, four, five, etc. neighboring slices). When multiple slices are included, the slices may be neighboring. For example, the initial MR data may include one or more 2D images of one or more respective slices in which the two lateral ventricles are prominent.

Next, at act 804, the initial MR image data is provided as input to a trained statistical classifier in order to obtain corresponding initial output. In some embodiments, prior to being provided to the trained statistical classifier, the initial MR image data may be pre-processed, for example, by resampling, interpolation, affine transformation, and/or using any other suitable pre-processing techniques, as aspects of the technology described herein are not limited in this respect.

In some embodiments, the output of the trained statistical classifier may indicate one or more initial locations, in the initial MR data, of one or more landmarks associated with at least one midline structure of the patient's brain. This location or locations may be identified from output of the trained statistical classifier at act 806 of process 800. The output may specify the location(s) directly or indirectly. In the latter case, the location(s) may be derived from information included in the output of the trained statistical classifier.

For example, in some embodiments, the output of the trained statistical classifier may indicate the locations of the anterior and posterior falx cerebri attachment points and the location of a measurement point in the septum pellucidum. When the initial MR data includes a 2D image of a corresponding slice, the output of the trained statistical classifier may indicate the locations of the landmarks (e.g., falx cerebri attachment points and measurement point in the septum pellucidum) within the 2D image. As described above, the locations of the falx cerebri attachment points and the measurement point in the septum pellucidum may be used to make a midline shift measurement.

Figure 10:
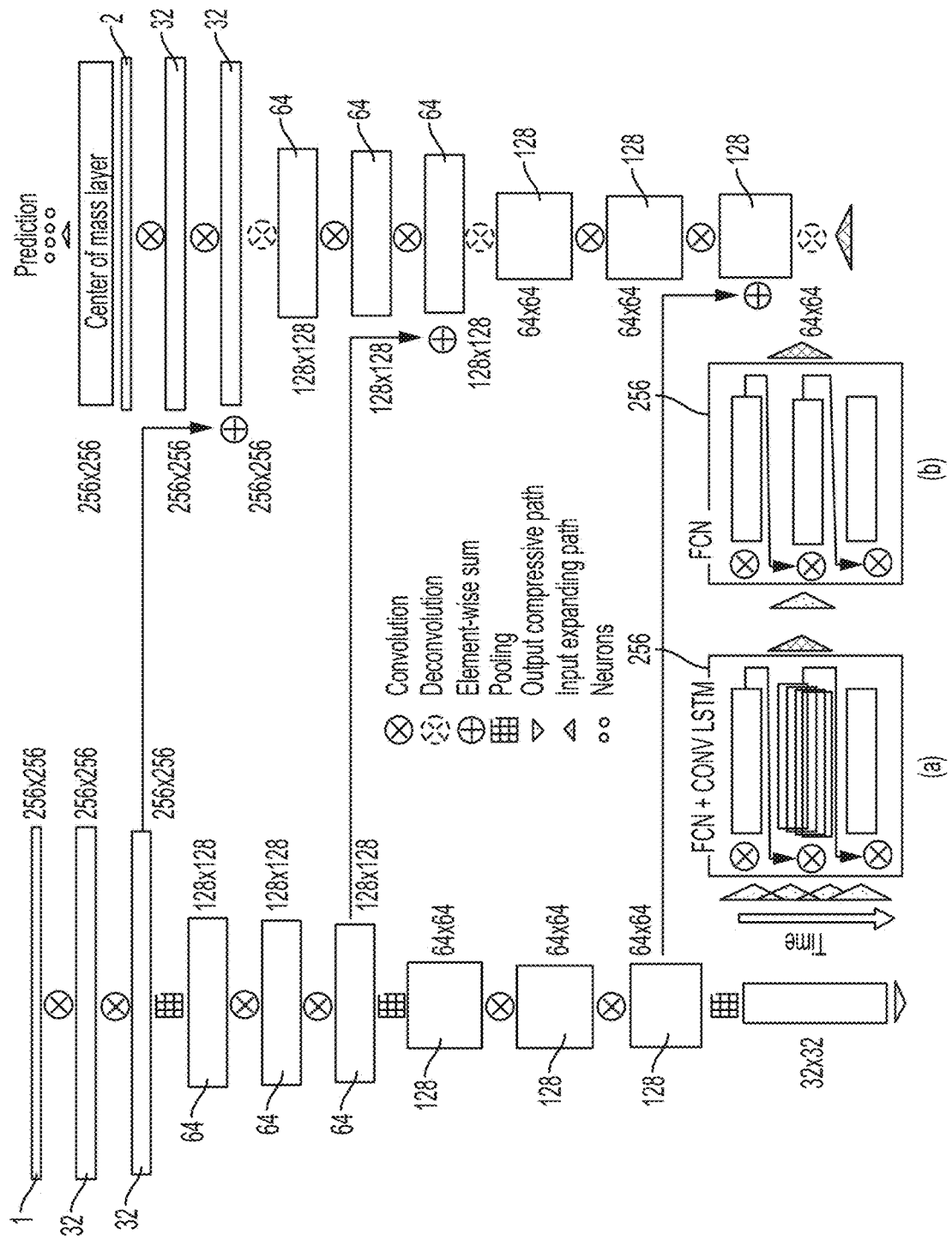
FIG. 10 illustrates fully convolutional neural network architectures for making midline shift measurements, in accordance with some embodiments of the technology described herein.

In some embodiments the trained statistical classifier may be a neural network statistical classifier. For example, the training statistical classifier may include a convolutional neural network (e.g., as illustrated in FIGS. 9A and 9B), a convolutional neural network and a recurrent neural network, such as a long short-term memory network, (e.g., as illustrated in FIGS. 9A and 9C), a fully convolutional neural network (e.g., as illustrated in FIG. 10), and/or any other suitable type of neural network. The trained statistical classifier may be implemented in software, in hardware, or using any suitable combination of software and hardware. In some embodiments, one or more machine learning software libraries may be used to implement the trained statistical classifier including, but not limited to, Theano, Torch, Caffe, Keras, and TensorFlow. These libraries may be used for training a statistical classifier (e.g., a neural network) and/or using a trained statistical classifier. Aspects of training the trained statistical classifier used at acts 804 and 806 are described in more detail below. It should also be appreciated that the trained statistical classifier is not limited to being a neural network and may be any other suitable type of statistical classifier (e.g., a support vector machine, a graphical model, a Bayesian classifier, a decision tree classifier, etc.), as aspects of the technology described herein are not limited in this respect.

As discussed above, in some embodiments, the trained statistical classifier may be a convolutional neural network. FIGS. 9A and 9B show an illustrative example of such a convolutional neural network. As shown in FIG. 9A, an input image (a 256×256 image in this example) is provided as input to the convolutional neural network, which processes the input image through an alternating series of convolutional and pooling layers. In this example, the convolutional neural network processes the input image using two convolutional layers to obtain 32 256×256 feature maps. Next, after an application of a pooling layer (e.g., a max pooling layer), two more convolutional layers are applied to obtain 64 128×128 feature maps. Next, after an application of another pooling layer (e.g., max pooling), two more convolutional layers are applied to obtain 128 64×64 feature maps. Next, after application of another pooling layer and another convolutional layer, the resulting 256 32×32 feature maps are provided as input to the portion of the neural network shown in FIG. 9B. In this portion, after an additional convolutions, the feature maps are processed through at least one fully connected layer to generate predictions. The predictions may, in some embodiments, indicate locations of falx cerebri attachment points (e.g., posterior and anterior attachment points, and a measurement point on the septum pellucidum).

FIGS. 9A and 9C show another illustrative example of a neural network that may be used as the trained statistical classifier, in some embodiments. The neural network of FIGS. 9A and 9C has a convolutional neural network portion (shown in FIG. 9A, which was described above) and a recurrent neural network portion (shown in FIG. 9C), which may be used to model temporal constraints among input images provided as inputs to the neural network over time. The recurrent neural network portion may be implemented as a long short-term memory (LSTM) neural network. Such a neural network architecture may be used to process a series of images obtained by a low-field MRI apparatus during performance of a monitoring task. A series of images obtained by the low-field MRI apparatus may be provided as inputs to the CNN-LSTM neural network, within which, features derived from at least one earlier-obtained image may be combined with features obtained from a later-obtained image to generate predictions.

In some embodiments, the neural networks illustrated in FIGS. 9A-9C may use a kernel size of 3 with a stride of 1 for convolutional layers, a kernel size of "2" for pooling layers, and a variance scaling initializer.

In some embodiments, the neural networks illustrated in FIGS. 9A-C may be used to process a single image (e.g., a single slice) at a time. In other embodiments, the neural networks illustrated in FIGS. 9A-9C may be used to process multiple slices (e.g., multiple neighboring slices) at the same time. In this way, the features used for prediction point locations (e.g., locations of the falx cerebri attachment points and a measurement point on the septum pellucidum) may be computed using information from a single slice or from multiple neighboring slices.

In some embodiments, when multiple slices are being processed by the neural network, the convolutions may be two-dimensional (2D) or three-dimensional (3D) convolutions. In some embodiments, the processing may be slice based so that features are calculated for each slice using information from the slice and one or more of its neighboring slices (only from the slice itself or from the slice itself and one or more of its neighbors). In other embodiments, the processing may be a fully-3D processing pipeline such that features for multiple slices are computed concurrently using data present in all of the slices.

In some embodiments, rather than using a convolutional neural network architecture with one or more fully connected output layers, as shown in FIGS. 9A-9C, a fully-convolutional neural network architecture may be employed. In such an architecture, the output is a single-channel output having the same dimensionality as the input. In this approach, a map of point locations (e.g., falx cerebri attachment points) is created by introducing Gaussian kernel intensity profiles at point locations, with the neural network trained to regress these profiles using mean-squared error loss.

FIG. 10 illustrates two different fully convolutional neural network architectures, which may be used in some embodiments. The first architecture, with processing involving processing path (a), includes three portions: (1) an output compressive portion comprising a series of alternating convolutional and pooling layers; (2) a long short-term memory portion (indicated by path (a)); and (3) an input expanding portion comprising a series of alternating convolutional and deconvolutional layers. This type of architecture may be used to model temporal constraints, as can the neural network architecture of FIGS. 9A and 9c. The second architecture, with processing involving processing path (b), includes three portions: (1) an output compressive portion comprising a series of alternating convolutional and pooling layers; (2) a convolutional network portion (indicated by path (b)); and (3) an input expanding portion comprising a series of alternating convolutional and deconvolutional layers and a center-of-mass layer. The center of mass layer computes the estimate as a center of mass computed from the regressed location estimates at each location.

In some embodiments, the neural networks illustrated in FIG. 10 may use a kernel size of 3 for convolutional layers with stride of 1, a kernel size of "2" for the pooling layers, a kernel of size 6 with stride 2 for deconvolutional layers, and a variance scaling initializer. In some embodiments, when multiple slices are being processed by one of the neural networks shown in FIG. 10, the convolutions may be two-dimensional (2D) or three-dimensional (3D) convolutions. In some embodiments, the processing may be slice based so that features are calculated for each slice using information from the slice and one or more of its neighboring slices. In other embodiments, the processing may be a fully 3D processing pipeline such that features for multiple slices are computed concurrently using data present in all of the slices.

It should be appreciated that the neural network architectures illustrated in FIGS. 9A-9C and FIG. 10 are illustrative and that variations of these architectures are possible. For example, one or more other neural network layers (e.g., a convolutional layer, a deconvolutional layer, a rectified linear unit layer, an upsampling layer, a concatenate layer, a pad layer, etc.) may be introduced to any of the neural network architectures of FIGS. 9A-9C and 10 as an additional one or more layers and/or instead of one or more layers part of the illustrated architectures. As another example, the dimensionality of one or more layers may be varied and/or the kernel size for one or more convolutional, pooling, and/or deconvolutional layers may be varied.

Next, process 800 proceeds to act 808, where the next MR image data is acquired. The next MR image data is acquired after the initial MR data acquired. Thus, although, in some embodiments, acts 804 and 806 may be performed after act 808 is performed, act 808 is generally performed after act 802. The next MR image data may be acquired immediately following acquisition of the initial MR image data, or may be obtained after a desired period of delay (e.g., within 1, 2, 3, 4, 5, 10, 15, 20 minutes, within one hour, within two hours, etc.). As with the initial MR image data, the next MR image data may be of any form (e.g., a 3D volumetric image, a 2D image, k-space MR data, etc.). In some embodiments, the initial MR data and the next MR image data are of the same type. For example, each of the initial and next MR data may include one or more two-dimensional images of one or more respective (e.g., neighboring) brain slices. For example, the initial MR data may include multiple images of neighboring slices obtained at a first time and the next MR data may include multiple images of the same neighboring slices obtained at a second time later than the first time.

Next, process 800 proceeds to act 810 where the next MR image data is provided as input to the trained statistical classifier to obtain the corresponding next output. In some embodiments, prior to being provided to the trained statistical classifier, the next MR image data may be pre-processed, for example, by resampling, interpolation, affine transformation, and/or using any other suitable pre-processing techniques, as aspects of the technology described herein are not limited in this respect. The next MR image data may be preprocessed in the same way as the initial MR data was preprocessed.

In some embodiments, the next output of the trained statistical classifier may indicate one or more updated locations, in the next MR data, of one or more landmarks associated with at least one midline structure of the patient's brain. This location or locations may be identified from output of the trained statistical classifier at act 812 of process 800. The output may specify the location(s) directly or indirectly. In the latter case, the location(s) may be derived from information included in the output of the trained statistical classifier.

For example, in some embodiments, the output of the trained statistical classifier obtained at act 812 may indicate the updated locations of the anterior and posterior falx cerebri attachment points and the updated location of a measurement point in the septum pellucidum. When the next MR data includes a 2D image of a corresponding slice, the corresponding output of the trained statistical classifier may indicate the updated locations of the landmarks (e.g., falx cerebri attachment points and measurement point in the septum pellucidum) within the 2D image. As described above, the updated locations of the falx cerebri attachment points and the measurement point in the septum pellucidum may be used to make a new/updated midline shift measurement.

Next, process 800 proceeds to act 814, where the degree of change in the midline shift is determined using the initial and updated locations of landmarks associated with midline structures that were obtained at acts 806 and 812, respectively. For example, in some embodiments, the initial locations of the falx cerebri attachment points and the measurement point in the septum pellucidum may be used to determine (e.g., calculate) an initial midline shift amount. The updated locations of the falx cerebri attachment points and the measurement point in the septum pellucidum may be used to determine an updated midline shift amount. The initial and updated midline shift amounts may be used to determine (e.g., by evaluating their difference) the degree of change in midline shift of the patient over the time period between the acquisition of initial and next MR data.

Next, process 800 proceeds to decision block 816, where it is determined whether to perform a new determination of the degree of change in the midline shift. This determination may be performed in any suitable way (e.g., by determining whether a threshold number of iterations have been performed, based on a schedule, based on manual input provided by a clinician, etc.), as aspects of the technology described herein are not limited in this respect. When it is determined that a new determination of the degree of change in the midline shift is to be performed, then process 800 returns to block 808 and acts 808-814 are repeated again (with newly obtained MR data being compared to the most recently previously obtained MR data). On the other hand, when it is determined that a new determination of the degree of change in the midline shift is not to be performed, process 800 completes.

It should be appreciated that process 800 is illustrative and that there are variations. For example, in some embodiments, the trained statistical classifier may be trained, as a multi-task model, such that its output may be used not only to identify one or more locations associated with at least one midline structure of the patient's brain, but also to segment the ventricles. As described herein, the measurement point to compare on to the midline lies on the septum pellucidum and it is therefore beneficial to use lateral ventricle labels to train a multi-task model, as such a model will identify the location of the septum pellucidum more accurately. The symmetry or asymmetry of the segmented lateral ventricles may help to identify the location of the septum pellucidum more accurately. Such a model may be trained if the training data includes lateral ventricle labels in addition to labels of the measurement point on the septum pellucidum and the falx cerebri attachment points.

The trained statistical classifier may be trained in any suitable way. In embodiments, where the trained statistical classifier is a neural network, the neural network may be trained any suitable neural network training technique including, but not limited to, gradient descent, stochastic gradient descent, backpropagation, and/or any other suitable iterative optimization technique. In embodiments where the neural network comprises a recurrent neural network, the training technique may employ stochastic gradient descent and backpropagation through time.

In some embodiments, the trained statistical classifier may be trained using training data comprising labeled scans of patients. For example, the classifier may be trained using training data comprising labeled scans of patients exhibiting midline shift (e.g., stroke patients and/or cancer patients). The scans may be annotated manually by one or more clinical experts. In some embodiments, the annotations may include indications of the locations of the falx cerebri attachment points and measurement points on the septum pellucidum. In some embodiments, the annotations may include a line representing the midline (instead of or in addition to indications of the locations of the falx cerebri location points). If there is no midline shift in a particular scan, no indication of the midline (a line or attachment points) may be provided.

The inventors have appreciated that there is an inherent ambiguity of the location of the measurement point. Specifically, slight shifts of the measurement point along the septum pellucidum may be tolerated, but shifts of the measurement point perpendicular to the pellucidum are not allowed. Accordingly, in some embodiments, the training data may be augmented by generating additional allowed locations for the location of the measurement point along the septum pellucidum.

As described above, the inventors have also developed low-field MRI techniques for determining whether there is a change in the size of an abnormality (e.g., a hemorrhage, a lesion, an edema, a stroke core, a stroke penumbra, and/or swelling) in a patient's brain. Indeed, MRI is an important and accurate modality for detecting acute hemorrhage in patients presenting with acute focal stroke symptoms, and is more accurate that CT scans for the detection of chronic intracerebral hemorrhages. Some studies have identified that MRI imaging is better than CT imaging for detection of acute ischemia and can accurately detect acute and chronic hemorrhage. As a result, MRI may be a preferred imaging modality for accurate diagnosis of patients suspected of having acute stroke and for monitoring abnormalities associated with a stroke.

Accordingly, in some embodiments, low-field MRI monitoring techniques may be combined with machine learning techniques to continuously monitor the size of the abnormality and detect changes in its size over time. In such embodiments, low-field MRI monitoring allows for obtaining a sequence of images of a patient's brain and the machine learning techniques described herein (e.g., deep learning techniques such as convolutional neural networks) may be used to determine, from the sequence of images, a corresponding sequence of sizes of the abnormality. For example, the deep learning techniques developed by the inventors may be used to segment (e.g., identify the outlines of) hemorrhages in MRI images, identify points that specify major axes of a 2D or 3D bounding region (e.g., box), identify a maximum diameter of the hemorrhage and a maximum orthogonal diameter of the hemorrhage that is orthogonal to the maximum diameter, and/or perform any other processing in furtherance of identifying the size of the hemorrhage.

In some embodiments, the volume of an abnormality may be identified using the so-called "ABC/2" formula for spherical or ellipsoidal abnormalities. The value A represents the length of a maximum diameter of the abnormality (e.g. length of diameter 1102 shown in FIG. 11A), the value B represents the length of a maximum orthogonal diameter of the abnormality that is orthogonal to the maximum diameter (e.g., length of diameter 1104 shown in FIG. 11A), and the value C is the total number of slices with the abnormality seen in the vertical plane multiplied by slice thickness. The values A, B, and C may then be multiplied and the product may be divided by 2 in order to estimate the volume of the abnormality. It should be appreciated that the length of the maximum diameter "A" and the length of the maximum orthogonal diameter "B" may be used to estimate the size (e.g., volume) of an abnormality in any other suitable way, as aspects of the technology described herein are not limited in this respect.

Accordingly, in some embodiments, the machine learning techniques described herein may be applied to processing MRI images to identify, within the MRI images, a first maximum diameter of an abnormality and a second maximum diameter. The first and second maximum diameters in turn may be used to estimate the size of the abnormality using the ABC/2 technique or in any other suitable way. For example, as shown in FIG. 11B, the machine learning techniques described herein are used to identify the first diameter 1106 of an abnormality and the second diameter 1108 of the abnormality orthogonal to the first diameter. The lengths of diameters 1106 and 1108 may be used to estimate the size of the abnormality shown in FIG. 11B (a right intraparenchymal basal ganglia hemorrhage).

Figure 11D:
Figure 11C:
Figure 11E:
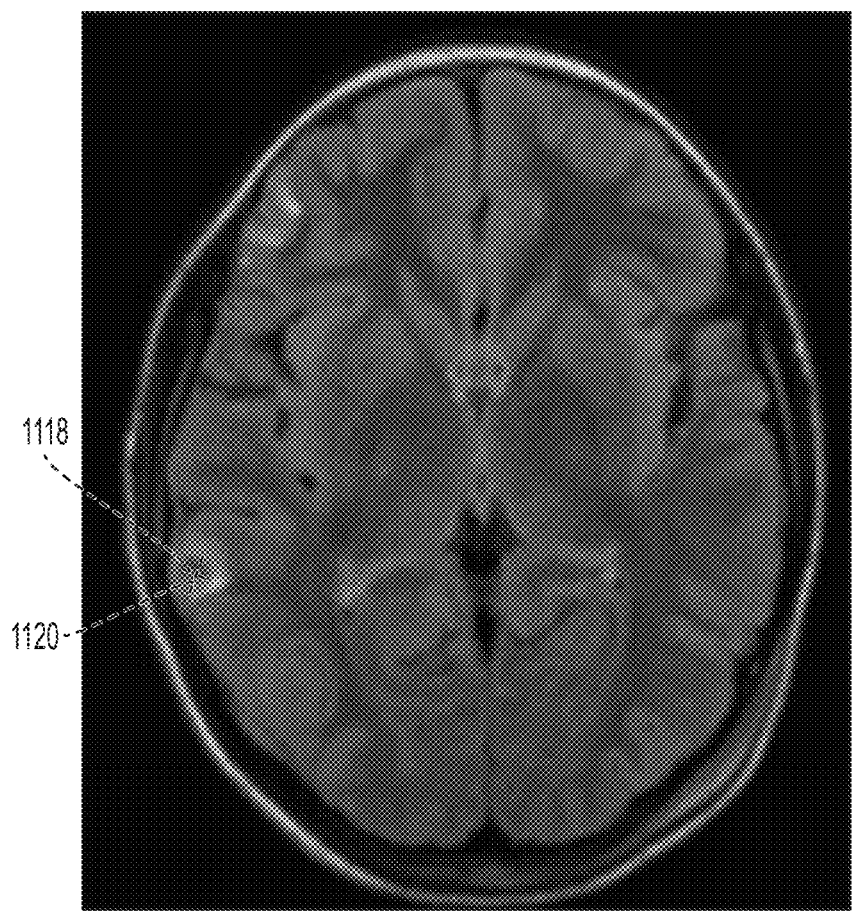
Figure 11F:
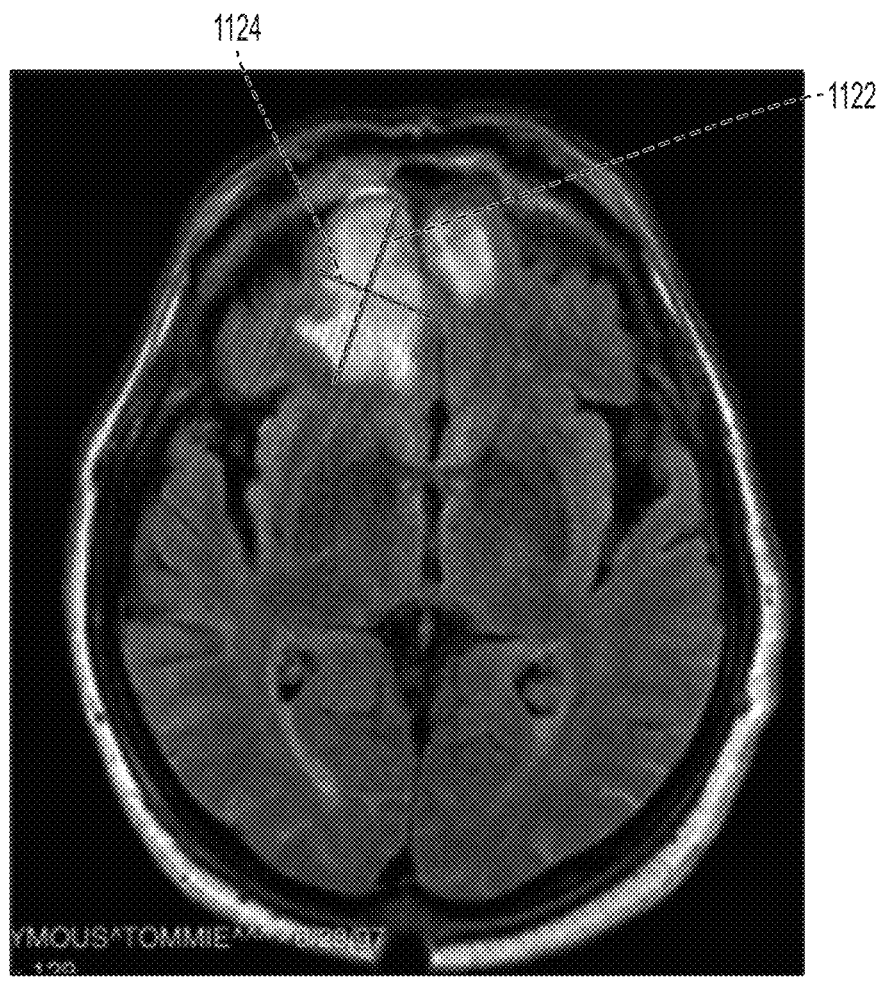

As another example, shown in FIG. 11C, the machine learning techniques described herein are used to identify the first diameter 1110 of the hematoma and the second diameter 1112 of the hematoma orthogonal to the first diameter. The lengths of diameters 1110 and 1112 may be used to estimate the size of the hematoma shown in FIG. 11C (a right parietotemporal intraparenchymal hematoma). As another example, shown in FIG. 11D, the machine learning techniques described herein are used to identify the first diameter 1114 of the hemorrhage and the second diameter 1116 of the hematoma orthogonal to the first diameter. The lengths of diameters 1114 and 1116 may be used to estimate the size of the hematoma shown in FIG. 11D (a right parietotemporal intraparenchymal hematoma). As another example, shown in FIG. 11E, the machine learning techniques described herein are used to identify the first diameter 1118 of the hemorrhage and the second diameter 1118 of the hemorrhage orthogonal to the first diameter. The lengths of diameters 1118 and 1120 may be used to estimate the size of the hemorrhage shown in FIG. 11E (intraparenchymal hemorrhage in the right parietal lobe with mild surrounding edema). As another example, shown in FIG. 11F, the machine learning techniques described herein are used to identify the first diameter 1122 of the hemorrhage and the second diameter 1124 of the hemorrhage orthogonal to the first diameter. The lengths of diameters 1122 and 1124 may be used to estimate the size of the hemorrhage shown in FIG. 11F (hemorrhagic contusions in the frontal lobe).

In some embodiments, changes in the size of an abnormality may be monitored. The size of the abnormality (e.g., a hemorrhage, a lesion, an edema, a stroke core, a stroke penumbra, and/or swelling) may be monitored by identifying the size of the abnormality in a series of images taken at different times. For example, as shown in FIG. 12A, the size of the hemorrhage in a first MRI image obtained at a first time may be determined based on the lengths of the diameters 1202 and 1204, which are identified using the machine learning techniques described herein (e.g., using a neural network having an architecture illustrated in FIG. 14 or FIG. 15). As shown in FIG. 12B, the size of the hemorrhage in a second MRI image obtained at a second time (occurring at least a threshold amount of time after the first time) may be determined based on the lengths of the diameters 1206 and 1208, which are also identified using the machine learning techniques described herein. Comparing the lengths of the diameters (and/or the hemorrhage sizes derived therefrom), as shown in FIG. 12C, allows one to determine whether the size of the hemorrhage changed (e.g., did it get smaller or larger?) and, if so, the amount by which the size changed.

Figure 13:
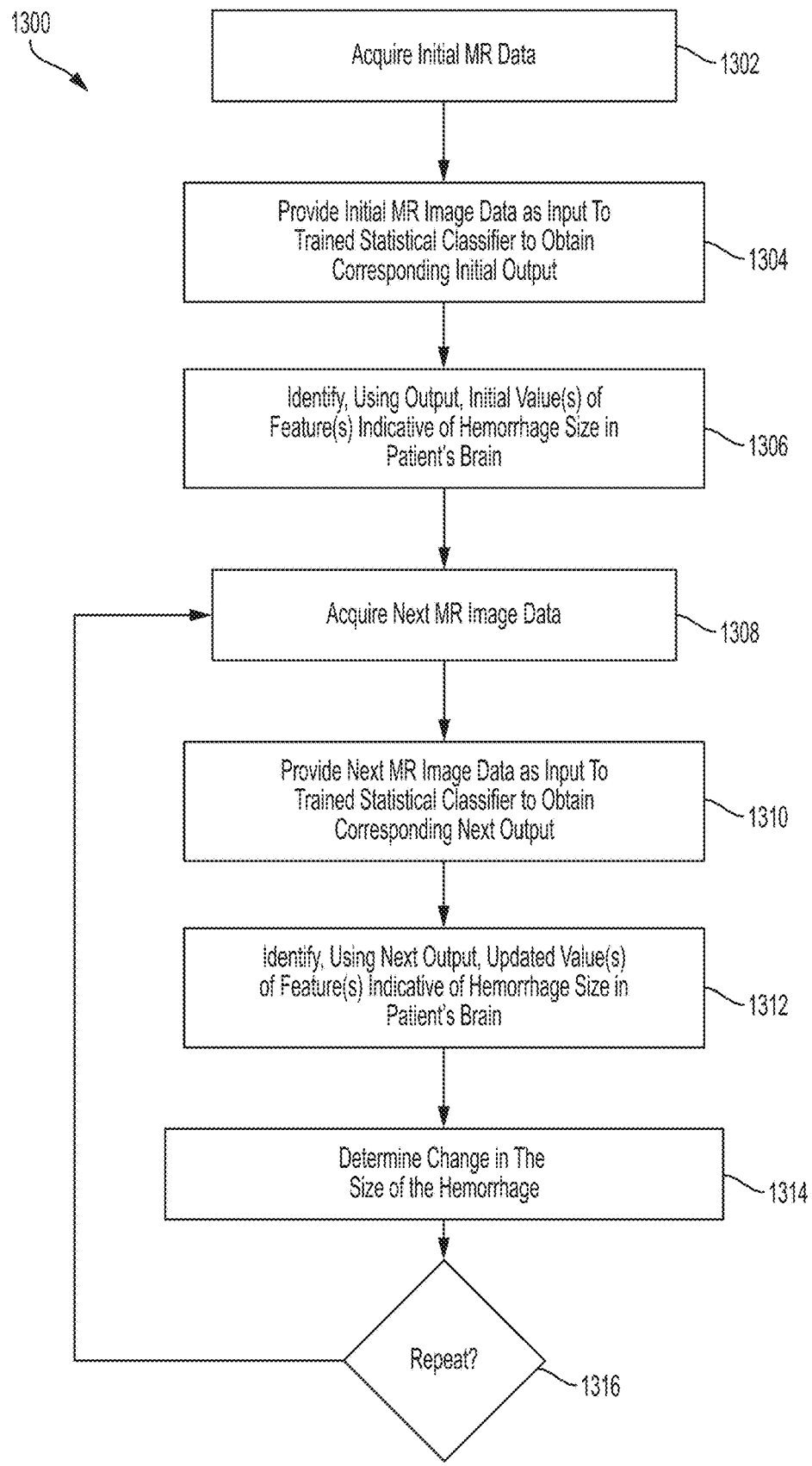
FIG. 13 illustrates a method for determining a degree of change in the size of an abnormality (e.g., hemorrhage) in the brain of a patient, in accordance with some embodiments of the technology described herein.

FIG. 13 is a flowchart of an illustrative process 1300 for determining a degree of change in the size of an abnormality (e.g., a hemorrhage, a lesion, an edema, a stroke core, a stroke penumbra, and/or swelling) in a patient's brain , in accordance with some embodiments of the technology described herein. In some embodiments, the entirety of process 1300 may be performed while the patient is within a low-field MRI device, which may be of any suitable type described herein including, for example, any of the low-field MRI devices illustrated in FIGS. 3A-3G). Although, for clarity, process 1300 is described with respect to detecting a change in the size of a hemorrhage, it should be appreciated that process 1300 may be applied to detecting changes in the size of any suitable type of abnormality (e.g., a hemorrhage, a lesion, an edema, a stroke core, a stroke penumbra, and/or swelling), as aspects of the technology described herein are not limited in this respect. Similarly, the neural network architectures described in FIGS. 14 and 15 may be applied to detecting changes in the size of any suitable type of abnormality, they are not limited to being used solely for detecting changes in size of a hemorrhage.

Process 1300 begins at act 1302, where the low-field MRI device acquires initial magnetic resonance data of a target portion of the patient's brain. As described herein, the term MR image data is used herein to refer to MR data generically including, but not limited to, MR data prior to image reconstruction (e.g., k-space MR data) and MR data that has been processed in some way (e.g., post-image reconstruction MR data such as a three dimensional (3D) volumetric image). In some embodiments, the initial MR data may include one or more two-dimensional images of respective brain slices (e.g., two, three, four, five, etc. neighboring slices). When multiple slices are included, the slices may be neighboring.

Next, at act 1304, the initial MR image data is provided as input to a trained statistical classifier in order to obtain corresponding initial output. In some embodiments, prior to being provided to the trained statistical classifier, the initial MR image data may be pre-processed, for example, by resampling, interpolation, affine transformation, and/or using any other suitable pre-processing techniques, as aspects of the technology described herein are not limited in this respect.

In some embodiments, the output of the trained statistical classifier may be used to identify, at act 1306, initial value(s) of feature(s) indicative of the size of a hemorrhage in the patient's brain. In some embodiments, the features may be a first maximum diameter of the hemorrhage in a first direction and a second maximum diameter of the hemorrhage in a second direction, which is orthogonal to the first direction. The values may indicate the initial lengths of the diameters and/or the initial endpoints of the diameters (from which the initial lengths may be derived). In some embodiments, the features may be corners of a bounding box bounding the perimeter of the hemorrhage and the initial values may be the locations of the corners. In some embodiments, the features may specify the boundary of the hemorrhage and the initial values may be the locations of one or more points along the segmented boundary. The output of the trained statistical classifier may specify the initial value(s) directly or indirectly. In the latter case, the value(s) may be derived from information included in the output of the trained statistical classifier.

In some embodiments, initial value(s) of the feature(s) obtained at act 1306 may be used to obtain an initial estimate of the size of the hemorrhage. For example, when the initial values may be used to determine initial lengths of maximum orthogonal diameters of the hemorrhage, the initial lengths may be used to estimate the initial volume of the hemorrhage (e.g., according to above-described ABC/2 method). As another example, when the initial values specify the boundary of a hemorrhage, the boundary information may be used to estimate the initial area of the hemorrhage in the slice (e.g., using a polygonal approximation or in any other suitable way).

Figure 14:
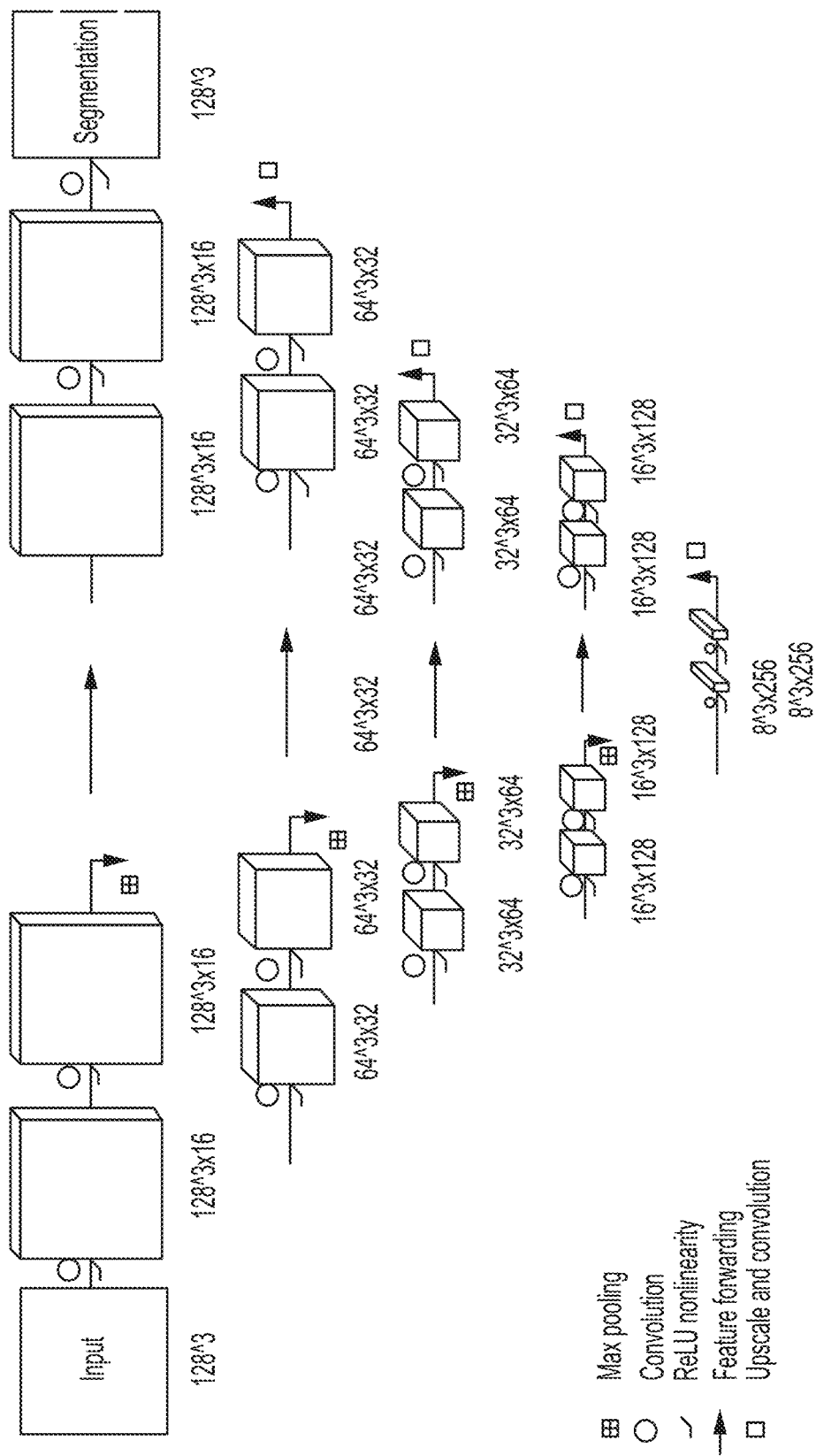
FIG. 14 illustrates a fully convolutional neural network architecture for making measurements that may be used to determine the size of an abnormality (e.g., hemorrhage) in a patient's brain, in accordance with some embodiments of the technology described herein.

In some embodiments the trained statistical classifier may be a neural network statistical classifier. For example, the training statistical classifier may include a fully convolutional neural network (e.g., as illustrated in FIGS. 10 and 14) or a convolutional neural network (e.g., as illustrated in FIGS. 9A-9C and 15), and/or any other suitable type of neural network. The trained statistical classifier may be implemented in software, in hardware, or using any suitable combination of software and hardware. In some embodiments, one or more machine learning software libraries may be used to implement the trained statistical classifier including, but not limited to, Theano, Torch, Caffe, Keras, and TensorFlow. These libraries may be used for training a statistical classifier (e.g., a neural network) and/or using a trained statistical classifier. The trained statistical classifier may be trained using any suitable training technique including any of the neural network training techniques (e.g., gradient descent) described above. It should also be appreciated that the trained statistical classifier is not limited to being a neural network and may be any other suitable type of statistical classifier (e.g., a support vector machine, a graphical model, a Bayesian classifier, a decision tree classifier, etc.), as aspects of the technology described herein are not limited in this respect.

In some embodiments, the trained statistical classifier may be one of the neural networks described above with reference to FIGS. 9A-9C or FIG. 10. Such a trained statistical classifier may identify point locations in MRI image data. For example, such a trained statistical classifier may be used to identify locations of endpoints of first and second orthogonal diameters of a hemorrhage. As another example, such a trained statistical classifier may be used to identify locations of corners of a bounding box of a hemorrhage.

In other embodiments, the trained statistical classifier may be a fully convolutional neural network having an architecture as illustrated in FIG. 14. Such a trained statistical classifier may be used to identify the boundary of the hemorrhage. Training such a neural network may involve zero-padding training images, using convolutional kernels of size 3 and stride 1, using a max pooling kernel with of size 2, and deconvolution (upscale and convolution) kernels with size 6 and size 2. The output of the neural network may identify the boundary of the hemorrhage.

Figure 15:
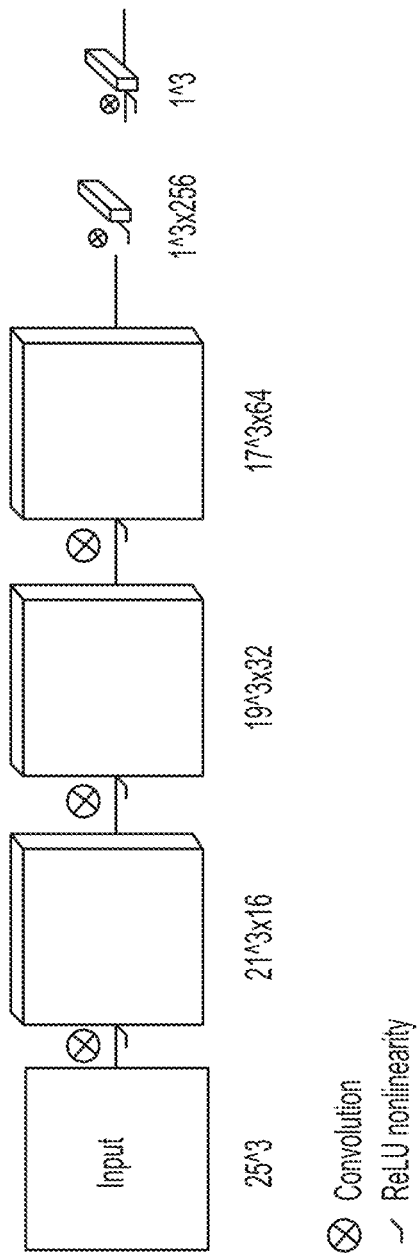
FIG. 15 illustrates a convolutional neural network architecture for making measurements that may be used to determine the size of an abnormality (e.g., a hemorrhage) in a patient's brain, in accordance with some embodiments of the technology described herein.

In yet other embodiments, the trained statistical classifier may be a convolutional neural network having an architecture as illustrated in FIG. 15. Such a trained statistical classifier may be used to identify the boundary of the hemorrhage by classifying individual voxels, which approach has the advantage of higher invariance to the location of the lesion. The neural network uses convolutional kernels with size 5 and stride 1 at the first layer and kernels with size 3 in the subsequent layers. This building block can be repeated for different sizes of the input neighborhood (25 as shown, 20, 15, or larger, 30, 35). Larger neighborhoods use larger initial kernel size (e.g., 7). The feature maps are merged in the last feature layer and combined to yield a single prediction.

It should be appreciated that the neural network architectures illustrated in FIGS. 14 and 15 are illustrative and that variations of these architectures are possible. For example, one or more other neural network layers (e.g., a convolutional layer, a deconvolutional layer, a rectified linear unit layer, an upsampling layer, a concatenate layer, a pad layer, etc.) may be introduced to any of the neural network architectures of FIGS. 14 and 15 as an additional one or more layers and/or instead of one or more layers part of the illustrated architectures. As another example, the dimensionality of one or more layers may be varied and/or the kernel size for one or more convolutional, pooling, and/or deconvolutional layers may be varied.

In some embodiments, when multiple slices are being processed by the neural network, the convolutions may be two-dimensional (2D) or three-dimensional (3D) convolutions. In some embodiments, the processing may be slice based so that features are calculated for each slice using information from the slice and one or more of its neighboring slices (the slice itself or the slice itself and one or more of its neighboring slices). In other embodiments, the processing may be a fully-3D processing pipeline such that features for multiple slices are computed concurrently using data present in all of the slices.

Next, process 1300 proceeds to act 1308, where the next MR image data is acquired. The next MR image data is acquired after the initial MR data acquired. Thus, although, in some embodiments, acts 1304 and 1306 may be performed after act 1308 is performed, act 1308 is generally performed after act 1302. The next MR image data may be acquired immediately following acquisition of the initial MR image data, or may be obtained after a desired period of delay (e.g., within 1, 2, 3, 4, 5, 10, 15, 20 minutes, within one hour, within two hours, etc.). As with the initial MR image data, the next MR image data may be of any form (e.g., a 3D volumetric image, a 2D image, k-space MR data, etc.). In some embodiments, the initial MR data and the next MR image data are of the same type. For example, each of the initial and next MR data may include one or more two-dimensional images of one or more respective (e.g., neighboring) brain slices. For example, the initial MR data may include multiple images of neighboring slices obtained at a first time and the next MR data may include multiple images of the same neighboring slices obtained at a second time later than the first time.

Next, process 1300 proceeds to act 1310 where the next MR image data is provided as input to the trained statistical classifier to obtain the corresponding next output. In some embodiments, prior to being provided to the trained statistical classifier, the next MR image data may be pre-processed, for example, by resampling, interpolation, affine transformation, and/or using any other suitable pre-processing techniques, as aspects of the technology described herein are not limited in this respect. The next MR image data may be preprocessed in the same way as the initial MR data was preprocessed.

In some embodiments, the output of the trained statistical classifier may be used to identify, at act 1312, updated value(s) of feature(s) indicative of the size of a hemorrhage in the patient's brain. In some embodiments, the features may be a first maximum diameter of the hemorrhage in a first direction and a maximum diameter of the hemorrhage in a second direction, which is orthogonal to the first direction. The updated values may indicate the updated lengths of the diameters and/or the endpoints of the diameters (from which the lengths may be derived). In some embodiments, the features may be corners of a bounding box bounding the perimeter of the hemorrhage and the updated values may be the updated locations of the corners. In some embodiments, the features may specify the boundary of the hemorrhage and the updated values may be the updated locations of one or more points along the segmented boundary. The output of the trained statistical classifier may specify the updated value(s) directly or indirectly. In the latter case, the value(s) may be derived from information included in the output of the trained statistical classifier.

In some embodiments, updated value(s) of the feature(s) obtained at act 1306 may be used to obtain an updated estimate of the size of the hemorrhage. For example, when the updated values may be used to determine updated lengths of maximum orthogonal diameters of the hemorrhage, the updated lengths may be used to estimate the volume of the hemorrhage (e.g., according to above-described ABC/2 method). As another example, when the updated values specify the boundary of a hemorrhage, the boundary information may be used to estimate the updated area of the hemorrhage in the slice.

Next, process 1300 proceeds to act 1314, where it is determined whether the size of the hemorrhage has changed and, if so, by how much. The determination may be made using the initial and updated value(s) obtained at acts 1306 and 1312, respectively. For example, in some embodiments, the initial value(s) obtained at act 1306 may be used to obtain an initial estimate of size (e.g., volume, area, etc.) for the hemorrhage and the updated value(s) obtained at act 1312 may be used to obtained an updated estimate of the size. In turn, the initial and updated size estimates may be used to determine whether the size of the hemorrhage changed (e.g., by evaluating their difference) and, if so, by how much.

Next, process 1300 proceeds to decision block 1316, where it is determined whether to continue monitoring the size of the hemorrhage for any changes. This determination may be performed in any suitable way (e.g., by determining whether a threshold number of iterations have been performed, based on a schedule, based on manual input provided by a clinician, etc.), as aspects of the technology described herein are not limited in this respect. When it is determined that monitoring is to continue, process 1300 returns to block 1308 and acts 1308-1314 are repeated again (with newly obtained MR data being compared to the most recently previously obtained MR data). On the other hand, when it is determined that monitoring need not continue, process 1300 completes.

Figure 16:
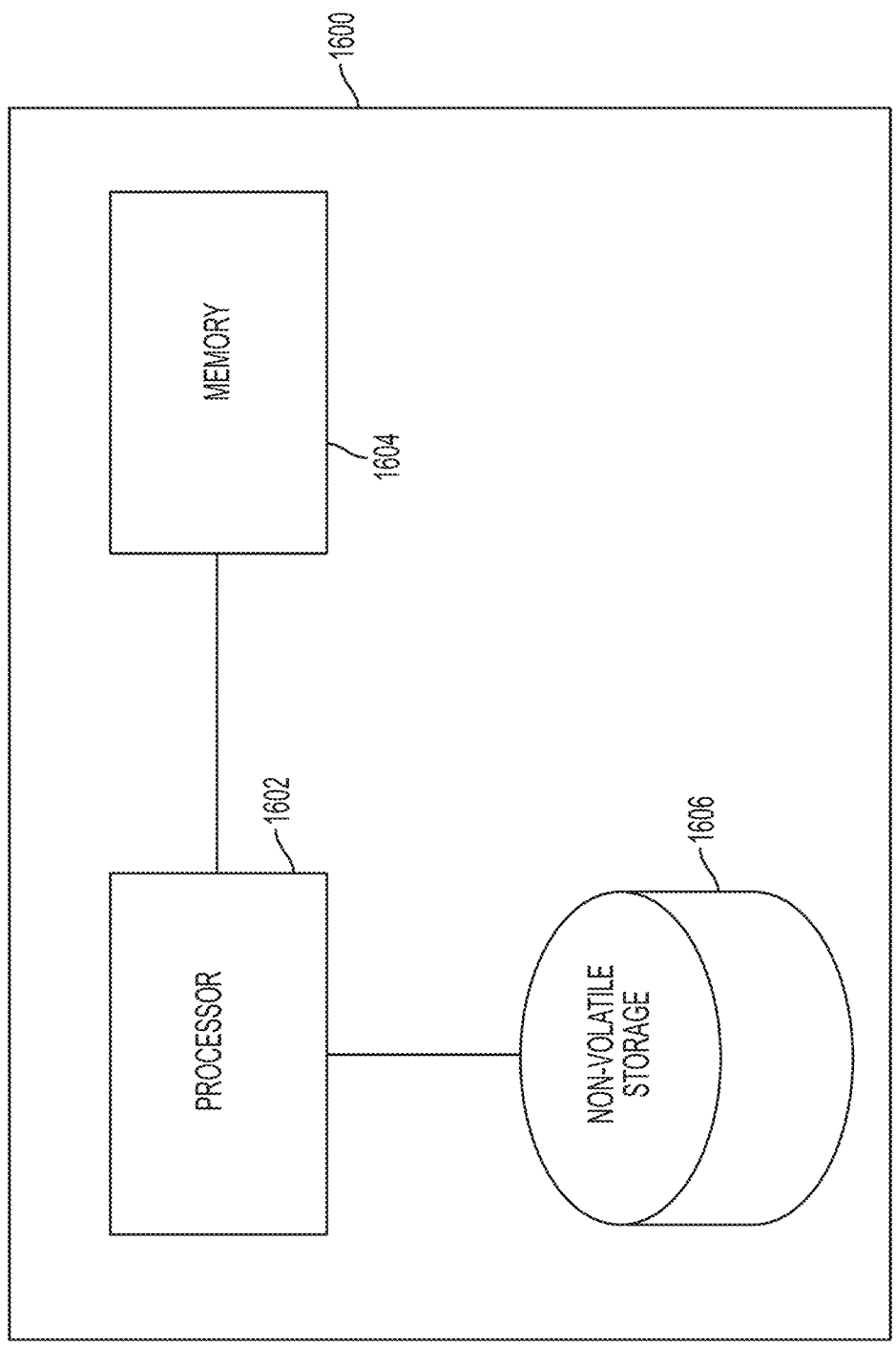
FIG. 16 is a diagram of an illustrative computer system on which embodiments described herein may be implemented.

FIG. 16 is a diagram of an illustrative computer system on which embodiments described herein may be implemented. An illustrative implementation of a computer system 1600 that may be used in connection with any of the embodiments of the disclosure provided herein is shown in FIG. 16. For example, the processes described with reference to FIGS. 8 and 13 may be implemented on and/or using computer system 1600. The computer system 1600 may include one or more processors 1610 and one or more articles of manufacture that comprise non-transitory computer-readable storage media (e.g., memory 1620 and one or more non-volatile storage media 1630). The processor 1610 may control writing data to and reading data from the memory 1620 and the non-volatile storage device 1630 in any suitable manner, as the aspects of the disclosure provided herein are not limited in this respect. To perform any of the functionality described herein, the processor 1610 may execute one or more processor-executable instructions stored in one or more non-transitory computer-readable storage media (e.g., the memory 1620), which may serve as non-transitory computer-readable storage media storing processor-executable instructions for execution by the processor 1610.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method of determining change in size of an abnormality in a brain of a patient using a low-field magnetic resonance imaging (MRI) device, the method comprising:
   acquiring first magnetic resonance (MR) image data of a patient's brain;
   providing the first MR image data as input to a trained statistical classifier to obtain corresponding first output;
   identifying, using the first output, at least one initial value of at least one feature indicative of a size of an abnormality in the patient's brain;
   acquiring second MR image data of the patient's brain subsequent to acquiring the first MR image data;
   providing the second MR image data as input to the trained statistical classifier to obtain corresponding second output;
   identifying, using the second output, at least one updated value of the at least one feature indicative of the size of the abnormality in the patient's brain; and
   determining the change in the size of the abnormality in the patient's brain using the first output and the second output;
   wherein determining the change in the size of the abnormality is performed using the at least one initial value of the at least one feature and the at least one updated value of the at least one feature.

2. The method of claim 1, wherein identifying, using the first output, the at least one initial value of the at least one feature indicative of the size of the abnormality in the patient's brain comprises identifying one or more first values indicative of a first diameter of the abnormality.

3. The method of claim 2, wherein the identifying further comprises identifying one or more second values indicative of a second diameter of the abnormality orthogonal to the first diameter.

4. The method of claim 1, wherein determining the change in the size of the abnormality using the at least one initial value of the at least one feature and the at least one updated value of the at least one feature comprises:
   determining an initial size of the abnormality using the at least one initial value of the at least one feature;
   determining an updated size of the abnormality using the at least one updated value of the at least one feature; and
   determining the change in the size of the abnormality using the determined initial and updated sizes of the abnormality.

5. The method of claim 1, wherein identifying, using the first output, the at least one initial value of the at least one feature indicative of the size of the abnormality in the patient's brain comprises identifying a region in the MR image data including the abnormality.

6. The method of claim 1, wherein the trained statistical classifier comprises a multi-layer neural network having at least one convolutional layer.

7. The method of claim 1, wherein the second MR image data is obtained within one hour of the first MR image data.

8. The method of claim 1, wherein the abnormality comprises a hemorrhage.

9. The method of claim 1, wherein the abnormality comprises a lesion, an edema, a stroke core, a stroke penumbra, and/or swelling.

10. A low-field magnetic resonance imaging (MRI) device configured to determine change in size of an abnormality in a brain of a patient, the low-field MRI device comprising:
    a plurality of magnetic components, including:
        at least one B0 magnet;
        at least one gradient coil; and
        at least one radio frequency coil; and
    at least one controller configured to operate the plurality of magnetic components to acquire first magnetic resonance (MR) image data of the patient's brain, and acquire second MR image data of the patient's brain subsequent to acquiring the first MR image data, wherein the at least one controller further configured to perform:
        providing the first and second MR image data as input to a trained statistical classifier to obtain corresponding first output and second output; and
        identifying, using the first output, at least one initial value of at least one feature indicative of a size of an abnormality in the patient's brain;
        identifying, using the second output, at least one updated value of the at least one feature indicative of the size of the abnormality in the patient's brain;
        determining the change in the size of the abnormality using the first output and second output, wherein determining the change in the size of the abnormality is performed using the at least one initial value of the at least one feature and the at least one updated value of the at least one feature.

11. The low-field MRI device of claim 10, wherein the abnormality comprises a hemorrhage, a lesion, an edema, a stroke core, a stroke penumbra, and/or swelling.

12. At least one non-transitory computer-readable storage medium storing processor-executable instructions that, when executed by at least one computer hardware processor, cause the at least one computer hardware processor, to perform method of determining change in size of an abnormality in a brain of a patient, the method comprising:
    acquiring first magnetic resonance (MR) image data of the patient's brain;
    providing the first MR image data as input to a trained statistical classifier to obtain corresponding first output;
    identifying, using the first output, at least one initial value of at least one feature indicative of a size of an abnormality in the patient's brain;
    acquiring second MR image data of the patient's brain subsequent to acquiring the first MR image data;
    providing the second MR image data as input to the trained statistical classifier to obtain corresponding second output;
    identifying, using the second output, at least one updated value of the at least one feature indicative of the size of the abnormality in the patient's brain; and
    determining the change in the size of the abnormality using the first output and the second output;
    wherein determining the change in the size of the abnormality is performed using the at least one initial value of the at least one feature and the at least one updated value of the at least one feature.

13. The at least one non-transitory computer-readable storage medium of claim 12, wherein identifying, using the first output, the at least one initial value of the at least one feature indicative of the size of the abnormality in the patient's brain comprises identifying one or more first values indicative of a first diameter of the abnormality and one or more second values indicative of a second diameter of the abnormality orthogonal to the first diameter.

14. The at least one non-transitory computer-readable storage medium of claim 12, wherein determining the change in the size of the abnormality using the at least one initial value of the at least one feature and the at least one updated value of the at least one feature comprises:
    determining an initial size of the abnormality using the at least one initial value of the at least one feature;
    determining an updated size of the abnormality using the at least one updated value of the at least one feature; and
    determining the change in the size of the abnormality using the determined initial and updated sizes of the abnormality.

15. A system, comprising:
    at least one computer hardware processor; and
    at least one non-transitory computer-readable storage medium storing processor-executable instructions that, when executed by the at least one computer hardware processor, cause the at least one computer hardware processor, to perform method of determining change in size of an abnormality in a brain of a patient, the method comprising:
        acquiring first magnetic resonance (MR) image data of the patient's brain;
        providing the first MR image data as input to a trained statistical classifier to obtain corresponding first output;

identifying, using the first output, at least one initial value of at least one feature indicative of a size of an abnormality in the patient's brain;

acquiring second MR image data of the patient's brain subsequent to acquiring the first MR image data;

providing the second MR image data as input to the trained statistical classifier to obtain corresponding second output;

identifying, using the second output, at least one updated value of the at least one feature indicative of the size of the abnormality in the patient's brain; and determining the change in the size of the abnormality using the first output and the second output;

wherein determining the change in the size of the abnormality is performed using the at least one initial value of the at least one feature and the at least one updated value of the at least one feature.

16. The system of claim 15, wherein identifying, using the first output, the at least one initial value of the at least one feature indicative of the size of the abnormality in the patient's brain comprises identifying one or more first values indicative of a first diameter of the abnormality and one or more second values indicative of a second diameter of the abnormality orthogonal to the first diameter.

17. The system of claim 15, wherein determining the change in the size of the abnormality using the at least one initial value of the at least one feature and the at least one updated value of the at least one feature comprises:

determining an initial size of the abnormality using the at least one initial value of the at least one feature;

determining an updated size of the abnormality using the at least one updated value of the at least one feature; and determining the change in the size of the abnormality using the determined initial and updated sizes of the abnormality.

* * * * *